United States Patent [19]

Dunlap et al.

[11] Patent Number: 5,650,422
[45] Date of Patent: Jul. 22, 1997

[54] SACCHARIN DERIVATIVES USEFUL AS PROTEOLYTIC ENZYME INHIBITORS AND COMPOSITIONS AND METHOD OF USE THEREOF

[75] Inventors: Richard Paul Dunlap, Penfield; Neil Warren Boaz, Village of Waterloo; Albert Joseph Mura, Rochester, all of N.Y.; Dennis John Hlasta, Lower Salford Township, Montgomery County, Pa.; Ranjit Chimanlal Desai, Towamencin Township, Montgomery County, Pa.; Chakrapani Subramanyam, Towamencin Township, Montgomery County, Pa.; Lee Hamilton Latimer, Town of Brighton, N.Y.; Eric Piatt Lodge, Upper Pottsgrove Township, Montgomery County, Pa.

[73] Assignee: Sanofi, Paris Cedex, France

[21] Appl. No.: 270,964

[22] Filed: Jul. 5, 1994

Related U.S. Application Data

[62] Division of Ser. No. 67,637, May 24, 1993, Pat. No. 5,371,074, which is a division of Ser. No. 793,033, Nov. 15, 1991, Pat. No. 5,236,917, which is a continuation-in-part of Ser. No. 514,920, Apr. 26, 1990, abandoned, which is a continuation-in-part of Ser. No. 347,126, May 4, 1989, abandoned, and Ser. No. 347,125, May 4, 1989, abandoned.

[51] Int. Cl.$^6$ .................. A61K 31/535; A61K 31/425; C07D 417/12; C07D 417/06
[52] U.S. Cl. .................. 514/373; 548/210; 544/135; 546/198; 546/271.1; 514/321; 514/338; 514/233.8
[58] Field of Search .................. 548/210; 514/373, 514/321, 338, 233.8; 544/135; 546/198, 271.1

[56] References Cited

U.S. PATENT DOCUMENTS

| | | |
|---|---|---|
| 3,002,884 | 10/1961 | Lo . |
| 3,284,450 | 11/1966 | Kraaijeveld et al. .......... 260/243 |
| 3,314,960 | 4/1967 | Freed et al. . |
| 4,195,023 | 3/1980 | Mulvey et al. .......... 548/209 |
| 4,263,393 | 4/1981 | Chen . |
| 4,276,298 | 6/1981 | Jones et al. . |
| 4,350,752 | 9/1982 | Reczek et al. . |
| 4,363,865 | 12/1982 | Reczek et al. . |
| 4,410,618 | 10/1983 | Vanmeter et al. . |
| 4,547,371 | 10/1985 | Doherty et al. .......... 514/200 |
| 4,623,645 | 11/1986 | Doherty et al. .......... 514/200 |
| 4,659,855 | 4/1987 | Powers .......... 558/23 |

FOREIGN PATENT DOCUMENTS

| | | |
|---|---|---|
| 1451417 | 9/1966 | France . |
| 7200419 | 12/1966 | Japan . |
| WO9013549 | 11/1990 | WIPO . |

OTHER PUBLICATIONS

Amal et al., Chemical Abstract 68:2688h (1967).
Yoon et al., Chemical Abstract 107:77681h (1986).
Svoboda et al., Chemical Abstracts 110:38982z (1983).
Bors et al., Chemical Abstracts 80:37097q (1971).
Cha, Biochem. Pharmacol., 24,2177–2185 (1975).
Powers, et al. Biochem., 24, 2048–2058 (1985).
Svoboda et al., Coll. Czech. Chem. Commun., 51, 1133–1139 (1986).
Teshima et al., J. Biol. Chem. 257(9), 5085–5091 (1982).

*Primary Examiner*—Johann Richter
*Assistant Examiner*—Laura R. Cross
*Attorney, Agent, or Firm*—Paul E. Dupont; William J. Davis

[57] ABSTRACT

Novel 2-substituted saccharins which inhibit the enzymatic activity of proteolytic enzymes, are useful in the treatment of degenerative diseases and have the formula

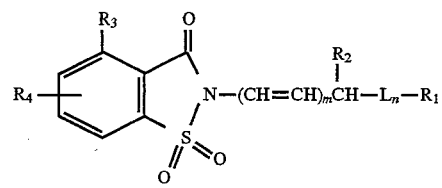

wherein:

L is —O—, —S—, —SO— or —$SO_2$—;

m and n are each independently 0 or 1;

$R_1$ is halo, lower-alkanoyl, 1-oxophenalenyl, phenyl or substituted phenyl, heterocyclyl or substitued heterocyclyl or, when L is —O— and n is 1, cycloheptatrienon-2-yl or, when L is —S— and n is 1, cyano or lower-alkoxythiocarbonyl or, when L is —$SO_2$— and n is 1, lower-alkyl or trifluoromethyl;

$R_2$ is hydrogen, lower-alkoxycarbonyl, phenyl or phenylthio; and $R_3$ and $R_4$ are each hydrogen or various substituents and processes for preparation and pharmaceutical compositions and method of use thereof are disclosed.

8 Claims, No Drawings

SACCHARIN DERIVATIVES USEFUL AS PROTEOLYTIC ENZYME INHIBITORS AND COMPOSITIONS AND METHOD OF USE THEREOF

CROSS REFERENCE TO RELATED APPLICATIONS

This application is a Division of our prior application Ser. No. 08/067,637, filed May 24, 1993, now U.S. Pat. No. 5,371,074, which is a Division of our prior application Ser. No. 07/793,033, filed Nov. 15, 1991, now U.S. Pat. No. 5,236,917 which in turn is a continuation-in-part of our prior application Ser. No. 07/514,920 filed Apr. 26, 1990, now abandoned, which is a continuation-in-part of application Ser. No. 07/347,126 filed May 4, 1989, now abandoned, and a continuation-in-part of application Ser. No. 07/347,125, filed May 4, 1989, now abandoned.

BACKGROUND OF THE INVENTION

1. Field of the Invention

This invention relates to novel 2-substituted saccharin derivatives, which inhibit the enzymatic activity of proteolytic enzymes, to compositions containing the same, to the method of use thereof in the treatment of degenerative diseases and to processes for their preparation.

2. Information Disclosure Statement

An additional information disclosure statement appears below at pages 130–133.

The inhibition of proteolytic enzymes by nontoxic reagents is useful in the treatment of degenerative disorders, such as emphysema, rheumatoid arthritis and pancreatitis, in which proteolysis is a substantive element.

Protease inhibitors are widely utilized in biomedical research. Serine proteases are the most widely distributed class of proteolytic enzymes. Some serine proteases are characterized as chymotrypsin-like or elastase-like based upon their substrate specificity.

Chymotrypsin and chymotrypsin-like enzymes normally cleave peptide bonds in proteins at a site at which the amino acid residue on the carbonyl side is typically Trp, Tyr, Phe, Met, Leu or another amino acid residue which contains aromatic or large alkyl side chains.

Elastase and elastase-like enzymes normally cleave peptide bonds at a site at which the amino acid residue on the carbonyl side of the bond is typically Ala, Val, Ser, Leu or other similar, smaller amino acids.

Both chymotrypsin-like and elastase-like enzymes are found in leukocytes, mast cells and pancreatic juice in higher organisms, and are secreted by many types of bacteria, yeast and parasites.

Several classes of compounds are known to be serine protease inhibitors. For example Powers U.S. Pat. No. 4,659,855 discloses arylsulfonyl fluoride derivatives useful as elastase inhibitors. Doherty et al. U.S. Pat. Nos. 4,547,371 and 4,623,645 disclose cephalosporin sulfones and sulfoxides, respectively, which are stated to be potent elastase inhibitors useful in the treatment of inflammatory conditions, especially arthritis and emphysema.

Teshima et al., J. Biol. Chem., 257(9), 5085–5091 (1982) report the results of studies on serine proteases (human leukocyte elastase, porcine pancreatic elastase, cathepsin G and bovine chymotrypsin Aa) with 4-nitrophenyl-esters and thioesters of N-trifluoroacetylanthranilates, 2-substituted-4H-3,1-benzoxazin-4-ones, 2-substituted-4-quinazolinones and 2-substituted-4-chloroquinazolines.

Cha, Biochem. Pharmacol., 24, 2177–2185 (1975) discusses kinetic approaches to the study of the binding of inhibitors to macromolecules, such as enzymes, and methods for determination of such parameters as the inhibition constants, reaction rates and bound and unbound enzyme concentrations.

Certain 2-substituted saccharin derivatives are known to have protease-type enzyme inhibitory activity. For example Mulvey U.S. Pat. No. 4,195,023 discloses $R_1$-2-$R_2$CO-1,2-benzisothiazol-3-ones, where $R_1$ is halogen, alkoxy, alkylamino, dialkylamino, alkoxycarbonyl, amino, nitro or hydrogen in the benzenoid ring thereof and $R_2$ is hydrogen, alkyl, alkenyl, alkynyl, cycloalkyl, halophenyl, heteroaryl or substituted heteroaryl, and $R_1$-2-A-CO-saccharins, where $R_1$ has the same meanings as the benzenoid ring substituents in the 1,2-benzisothiazol-3-ones and A is alkyl, alkenyl, alkynyl, cycloalkyl, fluorophenyl, heteroaryl or substituted-heteroaryl. The compounds are said to have elastase inhibitory activity and to be useful in the treatment of emphysema.

Jones et al., U.S. Pat. No. 4,276,298 discloses 2-R-1,2-benzisothiazolinone-1,1-dioxides, where R is phenyl substituted by fluoro, dinitro, trifluoromethyl, cyano, alkoxycarbonyl, alkylcarbonyl, carboxyl, carbamoyl, alkylacylamino, alkylsulfonyl, N,N-dialkylsulfamoyl, trifluoromethoxy, trifluoromethylthio, trifluoromethylsulfonyl and trifluoromethylsulfinyl, or pyridyl substituted the same as R when R is phenyl except that pyridyl may also be mono-nitro substituted. The compounds are said to have protease enzyme inhibitory activity, especially elastase inhibitory activity, and to be useful in the treatment of emphysema, rheumatoid arthritis "and other inflammatory diseases".

Powers, Blochem., 24, 2048–2058 (1985) discloses studies of the inhibitions of four chymotrypsin-like enzymes, cathepsin G, rat mast cell proteases I and II, human skin chymase and chymotrypsin $A_\alpha$, by N-furoylsaccharin and N-(2,4-dicyanophenyl) saccharin.

Svoboda et al., Coll. Czech. Chem. Commun., 51, 1133–1139 (1986) disclose the preparation of 4-hydroxy-2H-1,2-benzothiazine-3-carboxylates by intramolecular Dieckmann condensation of 2H-1,2-benzisothiazol-3-one-2-acetate-1,1-dioxide esters.

Chen, U.S. Pat. No. 4,263,393, Reczek et al. U.S. Pat. Nos. 4,350,752 and 4,363,865 and Vanmeter et al. U.S. Pat. No. 4,410,618 relate to photographic reagents (Reczek U.S. Pat. No. 4,350,752 and Vanmeter et al.), photographic dyes (Reczek U.S. Pat. No. 4,363,865) and "photographic elements and film units" (Chen) and disclose various 2-substituted-saccharins useful for such applications, for example 2-aroylmethylsaccharins by Chen, "photographic reagents" bound through a heteroatom to an "imidomethyl blocking" group (Reczek U.S. Pat. No. 4,350,752), "carrier-diffusible photographic dyes" bound to the nitrogen atom of an imide through a 1,1-alkylene group (Reczek U.S. Pat. No. 4,363,865) and N-acylmethylimides which are described as "blocked photographic reagents" and which have a "residue of an organic photographic reagent containing a hetero atom through which it is bound to the blocking group" (Vanmeter). Reczek U.S. Pat. No. 4,350,752 specifically discloses as "Compound 28" the species 2-(1-phenyl-1H-tetrazol-5-ylthiomethyl) saccharin, and Vanmeter specifically discloses a number of 2-(1-R'-1H-tetrazol-5-ylthiomethyl)-saccharins substituted on the methylene function by an aroyl or t-butylcarbonyl group.

Freed U.S. Pat. No. 3,314,960 discloses 2-(1,1,3-trioxo-1,2-benzisothiazol-2-yl)glutarimides which are stated to be useful as sedatives.

Japanese Patent Publication 72/00419 discloses a number of 2-RZ-methylsaccharins, stated to have strong activity against rice blast, rice sheath blight, rice helminthosporium leaf spot and rice bacterial leaf blight disease, wherein RZ is lower-alkoxy, butoxyethoxy, ethylthioethoxy, di-lower-alkylaminoethoxy, ethylthio, 2-chloroethoxy, 1-(2-propenyloxy), 1-(2-propynyloxy), 2-saccharinylmethoxy, phenoxy (or phenoxy substituted by chlorine, methyl, nitro or methylthio), phenylthio, chlorophenylthio, benzylthio (or chlorobenzylthio), acetoxy, dichloroacetoxy, benzoyloxy (or benzoyloxy substituted by chlorine or nitro), acetylthio, dichloroacetyloxy, chlorobenzoylthio, methyl or ethylcarbamyloxy, dimethylcarbamyloxy, phenylcarbamyloxy, ethylcarbamylthio, phenylcarbamylthio, dimethylthioylcarbamothioyl, ethylthiothioylthio, ethoxycarbonylthio, ethoxythioylthio and ethylthiocarbonylthio.

2-Chloromethylsaccharin is disclosed in French Patent 1,451,417 as an intermediate for the preparation of N-methylsaccharin d,1-trans-chrysanthemate, useful as an insecticide, and Lo U.S. Pat. No. 3,002,884 discloses 2-chloro, 2-bromo and 2-iodomethylsaccharins, useful as fungicidal agents.

SUMMARY

In a composition of matter aspect, this invention relates to 2-substituted saccharin derivatives which have protease enzyme inhibitory activity and which are useful in the treatment of degenerative diseases.

In a composition aspect, the invention relates to compositions for the treatment of degenerative diseases which comprise a pharmaceutical carrier and an effective proteolytic enzyme inhibiting amount of a 2-substituted saccharin derivative.

In a method aspect, the invention relates to a method of use of the said 2-substituted saccharins in the treatment of degenerative diseases which comprises administering to a patient in need of such treatment a medicament containing an effective proteolytic enzyme inhibiting amount of a said 2-substituted saccharin.

In a process aspect, the invention relates to a process for the preparation of said 2-saccharin derivatives which comprises reacting a 2-halomethylsaccharin either with an alkali metal salt of a $L_nR_1$ moiety or with a $L_nR_1$ moiety in the presence of an acid-acceptor.

In further process aspects, the invention relates to a process for the preparation of said 2-saccharin derivatives which comprises reacting an alkali metal or thallous salt of a 2-unsubstituted saccharin either with a halo-$CHR_2$—$L_nR_1$ moiety to obtain the desired product or with a 3-chloro-3-(phenylthio)propyl-$L_nR_1$ species followed by oxidation of the product with a per acid to obtain a 2-[1-(phenylsulfinyl)propyl-$L_nR_1$]saccharin and heating the latter to obtain a 2-[1-(2-propenyl)-$L_nR_1$]saccharin.

In a further process aspect, the invention relates to a process for the preparation of 4-primary-lower-alkyl-$R_4$-2-unsubstituted-saccharins, useful as intermediates for the preparation of the corresponding 2-saccharin derivatives, which comprises reacting a 4-methyl-$R_4$-2-unsubstituted-saccharin with two molar equivalents of a lower-alkyl lithium in an inert organic solvent and reacting the lithium salt thus produced with one molar equivalent of a lower-alkyl halide.

In a further process aspect, the invention relates to a process for the preparation of 4-primary- or secondary-lower-alkyl-$R_4$-2-unsubstituted-saccharins, useful as intermediates for the preparation of the corresponding 2-saccharin derivatives, which comprises reacting a 2-primary-lower-alkyl-N,N-di-lower-alkylbenzamide with a lower-alkyl lithium in an inert organic solvent; reacting the resulting lithium salt with a lower-alkyl halide; reacting the resulting 2-primary or secondary-lower-alkyl-$R_4$-N,N-di-lower-alkyl-benzamide with a lower-alkyl lithium; reacting the resulting lithium salt with sulfur dioxide followed by hydroxylaminesulfonic acid in the presence of base; and heating the product in an acid medium.

DETAILED DESCRIPTION OF THE PREFERRED EMBODIMENTS

More specifically this invention relates to 2-substituted saccharin derivatives having the formula:

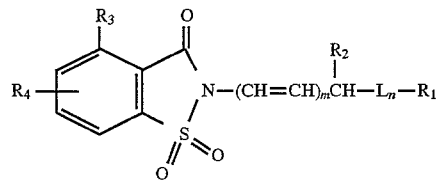

wherein:

L is —O—, —S—, —SO— or —$SO_2$—;

m and n are each independently 0 or 1;

$R_1$ is halogen, lower-alkanoyl, 1-oxo-phenalenyl, phenyl (or phenyl substituted by halogen, lower-alkyl, lower-alkoxy, nitro, amino, lower-alkylamino or di-lower-alkylamino) or heterocyclyl selected from 1H-(5-tetrazolyl), 5-oxo-1-tetrazolyl, 5-thioxo-1-tetrazolyl (when $R_2$ as defined hereinbelow is other than phenylthio), pyrimidinyl, 2-benzox-azolyl, 2-benzothiazolyl, 2-phthalimidyl, 2-(1,3,4-thiadiazolyl), 5-(1,2,4-thiadiazolyl), 5-thioxo-3-(1,2,4-thiadiazolyl), 4-(5-oxo-1,3,4-thiadiazolyl), 4-(5-thioxo-1,3,4-thiadiazolyl), 3-(1,2,4-triazolyl), 4-(1,2,4-triazolyl), (1,2,3-triazolyl), 2-imidazolyl or 3-(1,2,4-triazolo[4,3-a]-pyridinyl), or such heterocyclyl groups substituted on any available nitrogen atom by lower-alkyl, hydroxy-lower-alkyl, cycloalkyl, 2-, 3- or 4-pyrtdinyl, carboxy-lower-alkyl, lower-alkoxycarbonyl-lower-alkyl, aminocarbonyl-lower-alkyl, lower-alkylaminocarbonyl-lower-alkyl, di-lower-alkylaminocarbonyl-lower-alkyl, amino-lower-alkyl, lower-alkylamino-lower-alkyl, di-lower-alkylamino-lower-alkyl, 4-morpholinyl-lower-alkyl, 1-piperidinyl-lower-alkyl, 1-pyrrolidinyl-lower-alkyl or phenyl (or phenyl substituted by amino, lower-alkylamino, di-lower-alkylamino, lower-alkanamido, N-lower-alkyl-lower-alkanamido, carboxy-lower-alkanamido, carboxy, lower-alkoxycarbonyl, lower-alkoxy or halogen), or such heterocyclyl groups substituted on any available carbon atom by nitro, lower-alkyl, amino, lower-alkylamino, di-lower-alkylamino, cycloalkylamino, mercapto, lower-alkylthio, amino-lower-alkylthio, lower-alkylamino-lower-alkylthio, di-lower -alkylamino-lower-alkylthio, 4-morpholinyl-lower-alkylthio, 1-piperidinyl-lower-alkylthio, 1-pyrrolidinyl-lower-alkylthio, lower-alkoxycarbonyl or phenyl (or phenyl substituted by amino, lower-alkylamino, di-lower-alkylamino, lower-alkanamido, N-lower-alkyl-lower-alkanamido, lower-alkyl, lower-alkoxy or halogen);

$R_2$ is hydrogen, lower-alkoxycarbonyl, phenyl or phenylthio;

$R_3$ is hydrogen, halogen, primary or secondary lower-alkyl, lower-alkoxy, lower-alkoxycarbonyl, phenyl, fluoro-lower-alkyl, lower-alkenyl or cyano;

$R_4$ is hydrogen or from one to two substituents selected from halogen, cyano, nitro, amino, lower-alkanamido, phenyl-lower-alkanamido, diphenyl-lower-alkanamido, lower-alkylsulfonylamino, polyfluoro-lower-alkylsulfonylamino, aminosulfonyl, lower-alkyl, polyhalo-lower-alkyl, cycloalkyl, polyhalo-lower-alkoxy, hydroxy, lower-alkoxy, carboxy, hydroxymethyl, formyl, aminomethyl, lower-alkylsulfonyl, polyhalo-lower-alkylsulfonyl, lower-alkylsulfonyl-aminosulfonyl and lower-alkoxypoly-lower-alkyleneoxy; and wherein the —$CHR_2$— group is always appended either to a hetero atom of the L moiety as defined above or it is appended to a hetero atom of the $R_1$ moiety, with the provisos that (i) when m and n are 0 and $R_2$, $R_3$ and $R_4$ are all hydrogen, $R_1$ cannot be halogen; (ii) when m is 0, n is 1, L is —S— and $R_2$, $R_3$ and $R_4$ are each hydrogen, $R_1$ cannot be 1-phenyl-1H-(5-tetrazolyl); (iii) when m is 0, n is 1, L is —O— or —S—, and $R_2$, $R_3$ and $R_4$ are all hydrogen, $R_1$ cannot be lower-alkanoyl; (iv) when m is 0, n is 1, L is —O—, —S— or —SO—, and $R_2$, $R_3$ and $R_4$ are all hydrogen, or when m is 0, n is 1, L is —S—, $R_2$ and $R_4$ are hydrogen and $R_3$ is halogen, or when m is 0, n is 1, L is —SO— or —$SO_2$—, $R_2$ is lower-alkoxycarbonyl and $R_3$ and $R_4$ are both hydrogen, $R_1$ cannot be phenyl or substituted phenyl.

Preferred compounds of Formula I above are those wherein:

L is —O—, —S—, —SO— or —$SO_2$—;

m and n are each independently 0 or 1;

$R_1$ is halogen, lower-alkanoyl, 1-oxo-6- or 7-phenalenyl, phenyl (or phenyl substituted by halogen or nitro) or heterocyclyl selected from 1H- (5-tetrazolyl), 5-oxo-1-tetrazolyl, 5-thioxo-1-tetrazolyl (when $R_2$ as defined hereinbelow is other than phenylthio), pyrimidinyl, 2-benzoxazolyl, 2-benzothiazolyl, 2-phthalimidyl, 2-(1,3,4-thiadiazolyl), 5-(1,2,4-thiadiazolyl), 4-(5-oxo-1,3,4-thiadiazolyl), 4-(5-thioxo-1,3,4-thiadiazolyl), 3-(1,2,4-triazolyl), 4-(1,2,3-triazolyl), 2-imidazolyl or 3-(1,2,4-triazolo[4,3-a]-pyridinly), or such heterocyclyl groups substituted on any available nitrogen atom by lower-alkyl, hydroxy-lower-alkyl, cycloalkyl, 3- or 4-pyridinyl, carboxy-lower-alkyl, lower-alkoxycarbonyl-lower-alkyl, di-lower-alkylaminocarbonyl-lower-alkyl, 4-morpholinyl-lower-alkyl or phenyl (or phenyl substituted by amino, lower-alkanamido, carbòxy-lower-alkanamido, carboxy or lower-alkoxycarbonyl, or such heterocyclyl groups substituted on any available carbon atom by nitro, lower-alkyl, amino, cycloalkylamino, mercapto, lower-alkylthio, di-lower-alkylamino-lower-alkylthio, 4-morpholinyl-lower-alkylthio, 1-piperidinyl-lower-alkylthio, lower-alkoxycarbonyl or phenyl (or phenyl substituted by lower-alkanamido);

$R_2$ is hydrogen, carbo-lower-alkoxy, phenyl or phenylthio;

$R_3$ is hydrogen, halogen, primary or secondary-lower-alkyl, lower-alkoxy, lower-alkoxycarbonyl, phenyl, fluoro-lower-alkyl, lower-alkenyl or cyano; and $R_4$ is hydrogen, halogen, nitro, diphenyl-lower-alkanamido, lower-alkyl, hydroxy, lower-alkoxy or lower-alkoxyethoxyethoxy.

Other preferred compounds are those of formula I above wherein:

L is —S—, —SO— or —$SO_2$—;

m and n are each independently 0 or 1;

$R_1$ is 1-oxo-6- or 7-phenalenyl or heterocyclyl selected from 1H-(5-tetrazolyl), 5-oxo-1-tetrazolyl, 5-thioxo-1-tetrazolyl (when $R_2$ as defined hereinbelow is other than phenylthio), pyrimidinyl, 2-benzoxazolyl, 2-benzothiazolyl, 2-phthalimidyl, 2-(1,3,4-thiadiazolyl), 5-(1,2,4-thiadiazolyl), 4-(5-oxo-1,3,4-thiadiazolyl), 4-(5-thioxo-1,3,4-thiadiazolyl), 3-(1,2,4-triazolyl), 4-(1,2,3-triazolyl), 2-imidazolyl or 3-(1,2,4-triazolo[4,3-a]-pyridinyl) or such heterocyclyl groups substituted on any available nitrogen atom by lower-alkyl, hydroxy-lower-alkyl, cycloalkyl, 3- or 4-pyridinyl, carboxy-lower-alkyl, lower-alkoxycarbonyl-lower-alkyl, di-lower-alkylaminocarbonyl-lower-alkyl, 4-morpholinyl-lower-alkyl or phenyl (or phenyl substituted by amino, lower-alkanamido, carboxy-lower-alkanamido, carboxy or lower-alkoxycarbonyl), or such heterocyclyl groups substituted on any available carbon atom by nitro, lower-alkyl, amino, cycloalkylamino, mercapto, lower-alkylthio, di-lower-alkylamino-lower-alkylthio, 4-morpholinyl-lower-alkylthio, 1-piperidinyl-lower-alkylthio, lower-alkoxycarbonyl or phenyl (or phenyl substituted by lower-alkanamido);

$R_2$ is hydrogen, lower-alkoxycarbonyl, phenyl or phenylthio;

$R_3$ is hydrogen, halogen, primary or secondary-lower-alkyl, lower-alkoxy, lower-alkoxycarbonyl or phenyl; and $R_4$ is hydrogen, halogen, nitro, diphenyl-lower-alkanamido, lower-alkyl, hydroxy, lower-alkoxy or lower-alkoxyethoxyethoxy.

Particularly preferred compounds are those of formula I wherein: m is 0 or 1; n is 1; L is —S—; $R_2$ is hydrogen; $R_3$ is halogen, primary or secondary-lower-alkyl, lower-alkoxy, lower-alkoxycarbonyl or phenyl; and $R_1$ is 1H-(5-tetrazolyl), 5-oxo-1-tetrazolyl, 5-thioxo-1-tetrazolyl or 2-(1,3,4,-thiadiazolyl) or such groups substituted on a ring carbon or nitrogen atom thereof by substituents as defined above.

It should be understood that the compounds having the general structural formula I are usually named in the chemical literature as 1,2-benzisothiazol-(2H) -3-one-1,1-dioxides. However for the sake of brevity, such compounds are frequently named as saccharin derivatives, and that nomenclature will be used hereinafter in describing the compounds of the invention and their biological properties.

As used herein the terms lower-alkyl, lower-alkoxy and lower-alkane mean monovalent aliphatic radicals, including branched chain radicals, of from one to ten carbon atoms. Thus the lower-alkyl (or lower-alkane) moiety of such groups include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1,1,3,3-tetramethylpentyl, 1,1-dimethyloctyl and the like. Lower-alkanoyl has from two to ten carbon atoms and is branched or unbranched.

As used herein the term halogen (or halo) means fluorine, chlorine, bromine or iodine.

As used herein the term cycloalkyl means carbocyclic rings having from three to six ring carbon atoms, including cyclopropyl, cyclobutyl, cyclopentyl and cyclohexyl which may be substituted on any ring carbon atom thereof by one or more lower-alkyl groups.

As used herein the term lower-alkenyl means monovalent, unsaturated radicals, including branched chain radicals, of from three to ten carbon atoms and thus includes 1-(2-propenyl), 1-(2-butenyl), 1-(1-methyl-2-propenyl), 1-(4-methyl-2-pentenyl), 4,4,6-trimethyl-2-heptenyl and the like.

The compounds of the present invention inhibit the activity of serine proteases, specifically human leukocyte elastase and the chymotrypsin-like enzymes, and are thus useful in the treatment of degenerative disease conditions such as emphysema, rheumatoid arthritis and pancreatitis. In the process of binding to, and inhibiting, the activity of a proteolytic enzyme, it is believed that the compounds of the invention are cleaved at the bond between the methylene ($CHR_2$) and the $L_nR_1$ functions, and that the $L_nR_1$ group is split off as an anion which can thus be described as a "leaving group". This cleavage is believed to be facilitated by the presence of an "electron withdrawing group", such as cyano, halogen, nitro, carboxy, lower-alkoxycarbonyl, acyl or phenylthio, in the $R_1$ functionality to thereby increase its electro-negativity, which can be expressed in terms of the pKa values of the acid form of the "leaving group" which ideally should be less than about 7. A particularly preferred group of such compounds are those of formula I where $R_3$ is other than hydrogen.

The compounds of formula I where m is 0, $R_2$ is hydrogen and L is —O— or —S— are prepared by reaction of a 2-halomethylsaccharin derivative of formula I where $R_1$ is halogen, $R_2$ is hydrogen, m and n are 0 and $R_3$ and $R_4$ have the meanings given above, with an appropriate $L_nR_1$ moiety. The reaction can either be carried out in the presence of an acid-acceptor, such as an alkali metal carbonate, a tri-lower-alkylamine, an alkali metal or thallous-lower-alkoxide or an alkali metal hydride, or alternatively an alkali metal salt of the $L_nR_1$ moiety can be used. The reaction is carried out in an organic solvent inert under the conditions of the reaction, for example acetone, methyl ethyl ketone (MEK), tetrahydrofuran (THF), diethyl ether, dimethylformamide (DMF), methylene dichloride (MDC) or lower-alkanols, at a temperature in the range from ambient up to the boiling point of the solvent used. The corresponding compounds where L is —SO— or —$SO_2$— are prepared by oxidation of the corresponding compounds of formula I where L is —S— with one or two molar equivalents, as appropriate, of a peracid, such as 3-chloroperbenzoic acid.

Alternatively, the compounds of formula I where m is 0 can be prepared by reaction of an alkali metal or thallous saccharin salt (prepared by reaction of an appropriate 4-$R_3$-$R_4$-2-unsubstituted saccharin with an alkali metal alkoxide or a thallous lower-alkoxide) with a halo-$CHR_2$-$L_nR_1$ moiety, where $R_1$, $R_2$, $R_3$, $R_4$, L and n have the meanings given above with respect to formula I. A thallium salt can be used when $R_2$ has all the meanings given above, but an alkali metal salt can be used only when $R_2$ is hydrogen. The reaction is carried out in an inert organic solvent, for example a lower-alkanol or DMF, at temperatures in the range from 20° C. to the boiling point of the solvent used.

The compounds of formula I where m is 1 and $R_2$ is hydrogen are prepared by reaction of a 3-(phenylthio) propyl-$L_nR_1$ compound, prepared by reaction of a $L_nR_1$-propyl halide with sodium thiophenoxide in methyl ethyl ketone (MEK), followed by reaction of the product with N-chlorosuccinimide to give a 3-chloro-3-(phenylthio) propyl-$L_nR_1$ species. Reaction of the latter with a thallium salt of an appropriate 4-$R_3$-$R_4$-saccharin, using the same conditions described above for the preparation of the compounds of formula I from a saccharin salt and a halo-$CHR_2$-$L_nR_1$ moiety, affords a 2-[1-(phenylthio)propyl-$L_nR_1$] saccharin. Oxidation of the latter to the corresponding 2-[1-(phenylsulfinyl)propyl-$L_nR_1$]-saccharin followed by heating the product in an alkylene glycol ether, for example ethylene glycol dimethyl ether, affords the compounds of formula I where m is 1 and $R_2$ is hydrogen.

The compounds of formula I, where $R_1$ is lower-alkanoyl, $R_2$ is hydrogen, L is —O—, m is 0, n is 1, and $R_3$ and $R_4$ have the meanings given above, are prepared by treating the corresponding 2-hydroxymethylsaccharin with an appropriate acid anhydride in the presence of a catalytic amount of a mineral acid or a strong organic acid, for example sulfuric acid or p-toluenesulfonic acid.

The 2-halomethylsaccharins of formula I where $R_1$ is halogen, $R_2$ is hydrogen, m and n are 0, and $R_3$ and $R_4$ have the meanings given above with respect to formula I, and the corresponding 4-$R_3$-$R_4$-2-unsubstituted saccharins required for the preparation of the compounds of formula I where $R_1$, L, m and n have the other meanings given above, are prepared by the methods described by D'Alelio et al., J. Macromol. Sci-Chem., A3(5), 941 (1969) and Saari et al., J. Het. Chem., 23, 1253 (1986). In the method described by Saari, a methyl ester of an appropriate anthranilic acid is prepared by conventional means from the substituted anthranilic acid and the ester diazotized. The diazonium salt is then reacted with sulfur dioxide and cupric chloride to produce a sulfonyl chloride which is then reacted with concentrated ammonium hydroxide to produce the substituted saccharin derivatives of formula II. The latter, on reaction with formaldehyde in a lower-alkanol solvent affords the 2-hydroxymethylsaccharins of formula III, which, on reaction with a thionyl halide or a phosphorus tri-halide, afford the corresponding 2-halomethylsaccharin derivatives. The approach is illustrated as follows:

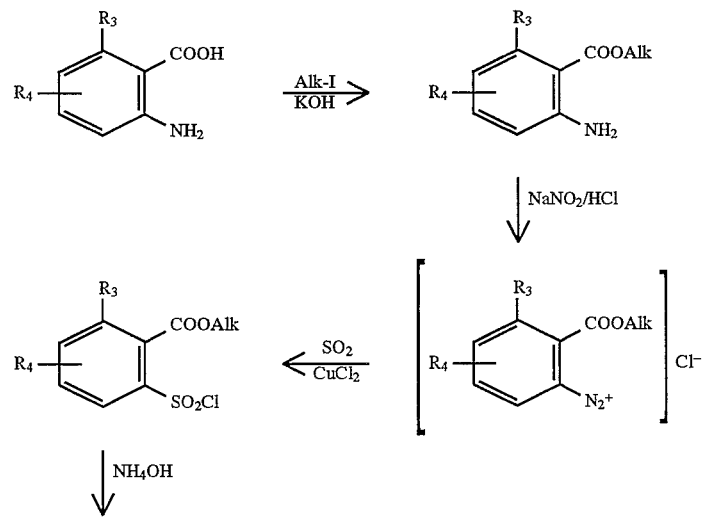

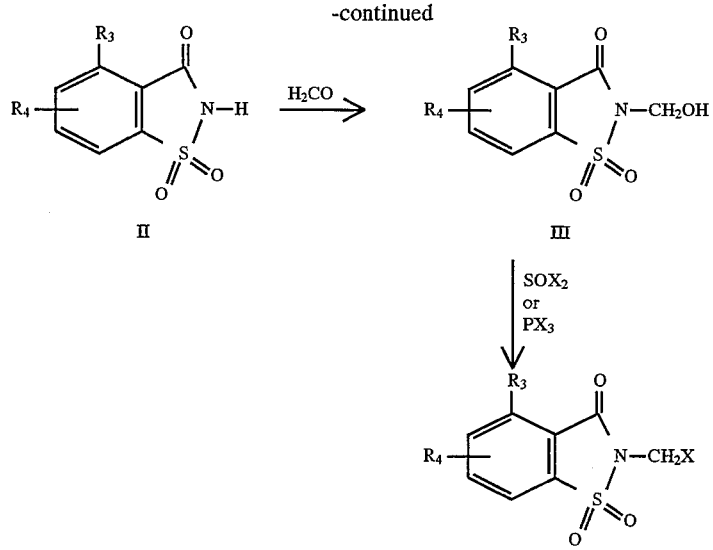

where $R_3$ and $R_4$ have the meanings given above and X is halogen.

The halomethylsacchartns of formula I, where $R_1$ is halogen, $R_2$ is hydrogen, m and n are 0, and $R_3$ and $R_4$ have the meanings given above with respect to formula I, can also be prepared by reaction of a corresponding 2-phenylthiomethylsaccharin with a sulfuryl halide in an inert organic solvent, for example MDC, ethylene dichloride (EDC) or carbon tetrachloride, at a temperature from around 0° C. to around 30° C.

The compounds of formula II where $R_3$ is either primary or secondary lower-alkyl, and which are useful as intermediates for the preparation of the compounds of formula I as described above, are prepared by one of two methods. The compounds of formula II where $R_3$ is primary lower-alkyl are prepared by reacting a 4-methyl-R4-2-unsubstituted-saccharin with two molar equivalents of a lower-alkyl lithium in an inert organic solvent, for example THF, and reacting the resulting lithium salt with one molar equivalent of a lower-alkyl halide, both reactions being carried out at a temperature in the range from about −50° C. to −80° C.

The compounds of formula II where $R_3$ is either primary or secondary lower-alkyl are prepared by reaction of a 2-primary-lower-alkyl-$R_4$-N,N-di-lower-alkylbenzamide with one molar equivalent of a lower-alkyl lithium in the presence of a tetra-lower-alkylethylenediamine in an inert organic solvent, for example THF and reaction of the resulting lithium salt with one molar equivalent of a lower-alkyl halide at a temperature in the range from about −50° C. to −80° C. The resulting 2-primary- or secondary-lower-alkyl-$R_4$-N,N-di-lower-alkyl-benzamide is then reacted with one molar equivalent of a lower-alkyl lithium in the presence of a tetra-lower-alkyl-ethylenediamine in an inert organic solvent, for example THF, and the resulting lithium salt reacted with sulfur dioxide at a temperature in the range from −50° C. to −80° C. followed by reaction of the product with hydroxylaminesulfonic acid in the presence of base. The resulting 2-lower-alkyl-$R_4$-6-amino-sulfonyl-N,N-di-lower-alkylbenzamide is thereafter heated in an acid medium to effect cyclization of the latter to the desired 4-primary or secondary lower-alkyl-$R_4$-2-unsubstituted-saccharin of formula II. It is preferred to carry out the cyclization in refluxing glacial acetic acid. When the 2-lower-alkyl group in the 2-lower-alkyl-$R_4$-N,N-di-lower-alkyl-benzamide starting material is methyl, alkylation affords species where the 2-lower-alkyl group is either straight or branched depending upon whether a straight or branched chain lower-alkyl halide is used for the alkylation. On the other hand, when the 2-lower-alkyl group in the starting material contains more than one carbon atom, alkylation takes place on the carbon atom adjacent the benzene ring and affords products having a sec.-lower-alkyl group at the 2-position.

Access to certain of the required intermediates of formula II in some cases requires building up the two rings making up the saccharin nucleus. Thus to prepare compounds where $R_3$ is lower-alkoxy and $R_4$ is 7-hydroxy, 3,3-dithiobis-propionic acid is converted to the bis acid chloride by reaction of the acid with thionyl chloride, and the acid chloride is then reacted with two molar equivalents of benzylamine to produce the bis n-benzylamide. The latter, on reaction with sulfuryl chloride in an organic solvent, such as MDC, EDC or carbon tetrachloride, affords 5-chloro-2-benzyl-2H-isothiazol-3-one, which is oxidized with one molar equivalent of a per acid, such as perbenzoic acid or 3-chloroperbenzoic acid, to 5-chloro-2-benzyl-2H-isothiazol-3-one-1-oxide. The latter, on heating under pressure with a 2-lower-alkoxyfuran in an organic solvent, such as benzene, toluene or xylene, affords a 4-lower-alkoxy-7-hydroxy-2-benzyl-1,2-benzisothiazol-2H-3-one-1-oxide. The 7-hydroxy group can, if desired, then be reacted with a lower-alkyl halide or a lower-alkoxypoly-lower-alkoxy-lower-alkyl halide to give the corresponding 4,7-di-lower-alkoxy or 4-lower-alkoxy-7-lower-alkoxypoly-lower-alkyleneoxy-2-benzyl-1,2-benzisothiazol-2H-3-one-1-oxide. Further oxidation of the product with one molar equivalent of a per acid as described before followed by catalytic debenzylation affords the corresponding 4-lower-alkoxy-7-$R_4$-2-unsubstituted saccharins.

Other simple chemical transformations which are conventional and well known to those skilled in the art of chemistry can be used for effecting changes in functional groups in the compounds of the invention. For example, catalytic reduction of nitro groups to produce the corresponding amino substituted compounds, acylation of amino-substituted species to prepare the corresponding amides or oxidation of sulfides or sulfoxides to prepare the corresponding, respective sulfoxides or sulfones as desired can be carried out.

In standard biological test procedures, the compounds of formula I have been found to possess human leukocyte elastase (HLE) and chymotrypsin inhibitory activities, and are thus useful in the treatment of degenerative diseases, such as emphysema, rheumatoid arthritis or pancreatitis.

The compounds of formula I having basic functions can be converted to the acid-addition salt form by interaction of the base with an acid. In like manner, the free base can be regenerated from the acid-addition salt form in conventional manner, that is by treating the salts with cold, weak aqueous bases, for example alkali metal carbonates and alkali metal bicarbonates. The bases thus regenerated can be interacted with the same or a different acid to give back the same or a different acid-addition salt. Thus the bases and all of their acid-addition salts are readily interconvertible.

Likewise certain compounds of formula I having acid, i.e. carboxylic acid, functions can be converted to salt forms thereof by reaction of the acid with a base, such as alkali metal or ammonium hydroxides or with organic bases such as alkyl, dialkyl or trialkylamines, and the acids can be regenerated from the salts by treatment of the salts with aqueous acids.

It will thus be appreciated that formula I not only represents the structural configuration of the bases and acids of formula I but is also representative of the structural entities which are common to all of the compounds of formula I whether in the form of the free base, the free acids or in the form of the salts of the bases and acids. It has been found that, by virtue of these common structural entities the compounds of formula I and their salts have inherent pharmacological activity of a type to be more fully described hereinbelow. This inherent pharmacological activity can be enjoyed in useful form for pharmaceutical purposes by employing the free bases or free acids themselves or the salts formed from pharmaceutically acceptable acids and bases, that is acids or bases whose anions or cations are innocuous to the animal organism in effective doses of the salts so that beneficial properties inherent in the common structural entity represented by the free bases and free acids are not vitiated by side effects ascribable to the anions or cations.

In utilizing this pharmacological activity of the salts, it is preferred, of course, to use pharmaceutically acceptable salts. Although water insolubility, high toxicity or lack of crystalline character may make some particular salt species unsuitable or less desirable for use as such in a given pharmaceutical application, the water-insoluble or toxic salts can be converted to the corresponding pharmaceutically acceptable bases by decomposition of the salts with aqueous base or aqueous acid as explained above, or alternatively they can be converted to any desired pharmaceutically acceptable salt by double decomposition reactions involving the anion or cation, for example by ion-exchange procedures.

Moreover, apart from their usefulness in pharmaceutical applications, the salts are useful as characterizing or identifying derivatives of the free bases or free acids or in isolation or purification procedures. Like all of the salts, such characterizing or purification salt derivatives can, if desired, be used to regenerate the pharmaceutically acceptable free bases or free acids by reaction of the salts with aqueous base or aqueous acid, or alternatively they can be converted to a pharmaceutically acceptable salt by, for example, ion-exchange procedures.

The novel feature of the compounds then resides in the concept of the bases and the cationic and anionic forms of the 4-$R_3$-$R_4$-2-substituted saccharins of formula I and not in any particular acid or base moiety or acid anion or base cation associated with the salt forms of the compounds; rather, the acid or base moieties or the anions or cations which can be associated with the salt forms are in themselves neither novel nor critical and therefore can be any acid anion or base cation capable of salt formation with the bases or acids.

The compounds of formula I of the invention can be prepared for pharmaceutical use by incorporating them in unit dosage form as tablets or capsules for oral administration either alone or in combination with suitable adjuvants such as calcium carbonate, starch, lactose, talc, magnesium stearate, gum acacia and the like. Still further, the compounds can be formulated for oral, parenteral or aerosol inhalation administration either in aqueous solutions of water soluble salts of the compounds or in aqueous alcohol, glycol or oil solutions or oil-water emulsions in the same manner as conventional medicinal substances are prepared.

The percentages of active component in such compositions may be varied so that a suitable dosage is obtained. The dosage administered to a particular patient is variable, depending upon the clinician's judgment using as criteria: the route of administration, the duration of treatment, the size and physical condition of the patient, the potency of the active component and the patient's response thereto. An effective dosage amount of the active component can thus only be determined by the clinician after a consideration of all criteria and using his best judgment on the patient's behalf.

The molecular structures of the compounds of the invention were assigned on the basis of study of their infra-red and NMR spectra. The structures were confirmed by the correspondence between calculated and found values for elementary analyses for the elements.

The following examples will further illustrate the invention without, however, limiting it thereto. All melting points are uncorrected.

EXAMPLE 1

Powdered potassium hydroxide (7.4 g; 132 mmol; 2 equiv.) was admixed with dimethyl sulfoxide (DMSO) (100 ml), and the mixture was stirred for 5 minutes. 6-Methylanthranilic acid (10.0 g; 66 mmol) was then added to the mixture and iodomethane (4.52 ml; 73 mmol; 1.1 equiv.) added dropwise. The reaction mixture was stirred for 30 minutes at room temperature, then diluted with ether (250 ml), washed with water (3×100 ml), dried (MgSO$_4$) and concentrated. The crude product was filtered through a pad of. flash grade (32–63 ) silica gel and eluted with 1:9 ether:hexane to afford 4.23 g (39%) of methyl 6-methylanthranilate as an oil. $^1$H nmr (300 MHz, CDCl$_3$): 7.078 (1H, t, J=7.67 Hz); 6.529 (2H, d, J=7.79 Hz); 5.111 (2H, br s); 3.887 (3H, s); 2.424 (3H, s). IR (neat film, cm$^1$): 3480 (m), 3380 (m), 2950 (w), 1690 (s); 1605 (s).

The methyl 6-methylanthranilate prepared in (a) (4.23 g; 25.6 mmol) was dissolved in acetic acid (25 ml) and the solution cooled to 0° C. Concentrated hydrochloric acid (45 ml) was added to produce a tan slurry. A solution of sodium nitrite (1.89 g; 27.4 mmol; 1.07 equiv.) in water (8 ml) was added dropwise with stirring, the resulting orange solution was stirred at 0° C. for 1 hour and then added in 6 portions to a mixture of cupric chloride dihydrate (2.18 g; 12.8 mmol; 0.5 equiv.) and sulfur dioxide (6.3 g; excess) in acetic acid (33 ml) and water (6 ml) at 0° C. The dark green solution was stirred at room temperature overnight, poured into ice-water (300 ml), and the solid which separated was collected and dried by suction to provide 1.11 g of the sulfonyl chloride which was immediately added to ice cold ammonium hydroxide (100 ml) and stirred at room temperature overnight. The solution was acidified to pH 1 with concentrated HCl and the resulting precipitate was collected and air-dried to provide 729 mg (12%) of 4-methylsaccharin, mp 224°–226° C. $^1$H nmr (300 MHz, $CD_3CN$): 9.5 (1H, br s); 7.782 (2H, d, J=4.35 Hz); 7.644 (1H, t, J-4.20 Hz); 2.683 (3H, s). IR (KBr, $cm^1$): 3400 (w); 3100 (s); 3000 (s); 1720 (s); 1580 (m). FDMS: m/e 197 ($M^+$).

4-Methylsaccharin prepared in (b) (500 mg; 2.54 mmol) was dissolved in 2.53 ml of warm ethanol (steam bath). Once a homogeneous solution was achieved, formalin (37% in methanol; 1.76 ml excess) was added dropwise. The solution was allowed to cool to room temperature and then chilled to 0° C. for 4 days. The resulting solid was collected and air-dried to afford 476 mg (82%) of 2-hydroxymethyl-4-methylsaccharin, mp 196°–198° C. $^1$H nmr (300 MHz, $CDCl_3$): 7.767 (1H, t, J=6.75 Hz); 7.732 (1H, d, J=7.72 Hz); 7.600 (1H, d, J=6.64 Hz); 5.361 (2H, d, J-8.00 Hz); 3.296 (1H, t, J=8.16 Hz); 2.793 (3H, s). IR (KBr, $cm^1$): 3505 (s); 3070 (w); 1735 (s); 1580 (m).

2-Hydroxymethyl-4-methylsaccharin produced in (c) (76 mg; 0.33 ml) was admixed with acetic anhydride (1 ml; excess), and 2 drops of concentrated sulfuric acid were added. The reaction mixture was stirred for 2 hours at room temperature, at which time a non-polar spot was observed by thin-layer chromatographic (tlc) analysis. The reaction mixture was diluted with MDC (50 ml) and washed with saturated sodium bicarbonate (2×15 ml). After drying ($Na_2SO_4$), the solvent was removed to afford 64 mg (72%) of 2-acetoxymethyl-4-methylsaccharin, mp 198°–205° C. (decomp.) $^1$H nmr (300 MHz, $CDCl_3$): 7.8 (2H, m); 7.64 (1H, d, J=6.18 Hz); 5.84 (2H, s); 2.82 (3H, s); 2.15 (3H, s). IR (KBr, $cm^1$): 2920 (w); 1745 (s); 1735 (s); 1630 (w). FDMS: m/e 269 ($M^+$).

EXAMPLE 2

Using the procedure described above in Example 1, 6-chloroanthranilic acid (5.00 g; 29.2 mmol) and iodomethane (2.75 ml; 44 mmol; 1.5 equiv.) were reacted in the presence of powdered potassium hydroxide (4.08 g; 72.7 mmol; 2.5 eguiv.) to give 4.22 g (78%) of methyl 6-chloroanthranilate as an oil. $^1_H$ nmr (300 MHz, $CDCl_3$): 7.077 (1H, t, J=8.06 Hz); 6.744 (1H, d, J=6.7 Hz); 6.575 (1H, d, J=8.25 Hz); 4.871 (1H, br s); 3.929 (3H, s). IR (neat film, $cm^1$): 3480 (m); 3380 (m); 2950 (w); 1705 (s); 1610 (s).

4-Chlorosaccharin was prepared by the same method as used for preparing 4-methylsaccharin using methyl 6-chloro-anthranilate (4.22 g; 22.7 mmol) in acetic acid (22 ml) and conc. HCl (40 ml) and sodium nitrite (1.68 g; 24.3 mmol) in water (7 ml) to prepare the diazonium salt which was added to cupric chloride dihydrate (1.93 g; 11.4 mmol; 0.5 equiv.) and sulfur dioxide (6.5 g; excess) in acetic acid (30 ml)/water (5 ml). The resulting sulfonyl chloride was treated with ammonium hydroxide (150 ml) as previously described to afford 3.07 g (62%) of 4-chlorosaccharin as a pale yellow solid, mp 245°–246° C. $^1$H nmr (300 MHz, $CD_3CN$): 7.918 (1H, dd, J=7.39, 1.91 Hz); 7.865 (1H, t, J-7.52 Hz); 7.829 (1H, br d, J=7.30 Hz). IR (KBr, $CM^1$): 3570 (s); 3520 (s); 2950 (s,b); 1735 (s); 1630 (m). FDMS: m/e 217 ($M^+$).

2-Hydroxymethyl-4-chlorosaccharin was prepared in the same manner as 2-hydroxymethyl-4-methylsaccharin, in Example 1, from 4-chlorosaccharin (1.00 g; 4.60 mmol) and formalin (37%; 3.22 ml; excess). All attempts to crystallize the viscous oily product resulted in decomposition to the starting material, and the product was thus used in the next step without characterization.

2-Acetoxymethyl-4-chlorosaccharin was prepared in the same manner as used for 2-acetoxymethyl-4-methylsaccharin, in Example 1, from the crude 2-hydroxymethyl-4-chlorosacharin (0.34 g; 1.4 mmol) and acetic anhydride (2.5 ml) with 2 drops of sulfuric acid. In this case, after isolation, the product was purified by filtration through a pad of silica gel and elution with 1:1 ether:hexane to afford 2-acetoxymethyl-4-chlorosaccharin (35 mg, 95% yield) as a white solid, mp 138°–142° C. $^1$H nmr (300 MHz, $CDCl_3$): 7.921 (1H, dd, J=6.54, 2.63 Hz); 7.874 (1H, t, J=7.98 Hz); 7.842 (1H, dd, J=6.70, 2.20 Hz); 5.869 (2H, s); 2.172 (3H, s). IR (KBr, $CM^1$): 1745 (s); 1735 (m, shoulder); 1575 (w). Comb. anal.:

Theor C, 41,46; H, 2.78; N, 4.83;

Found C, 41.17; H, 2.81; N, 4.75.

EXAMPLE 3

Crude 2-hydroxymethyl-4-chlorosaccharin, from Example 2, (609 mg; 2.46 mmol max) was admixed with diethyl ether (5 ml), and thionyl chloride (3 ml; excess) was added. The resulting mixture was heated to effect complete solution, stirred at room temperature overnight, diluted with ether (20 ml) and filtered through a pad of celite topped with sand and eluted with ether. Removal of the solvent afforded 430 mg of crude chloromethyl derivative. A portion (225 mg) was removed for further reactions. The remainder (205 mg) was flash chromatographed on silica gel and eluted with 40% ether/pentane to provide 137 mg of 2-chloromethyl-4-chloro-saccharin, mp 135°–136° C. $^1$H nmr (300 MHz, $CDCl_3$): 7.925 (1H, dd, J=6.62, 2.26 Hz); 7.882 (1H, t, J=8.18 Hz); 7.846 (1H, dd, J=7.42, 2.36 Hz); 5.561 (2H, s). IR (KBr, $CM^1$): 3090 (w); 3050 (w); 1750 (s); 1575 (m). FDMS: m/e 265 ($M^+$).

EXAMPLE 4

The chloromethyl derivative prepared in Example 3 (225 mg; 0.85 mmol) and sodium 1-phenyl-5-mercapto-1H-tetrazole (200 mg; 1.01 mmol; 1.2 equiv.) were dissolved in acetone (5 ml) to give a tan solution. After about 10 minutes a precipitate was observed, and after stirring overnight at room temperature no 2-chloromethyl-4-chlorosaccharin was present by tlc analysis. The reaction mixture was poured into water and extracted with MDC (3×25 ml). The combined extracts were dried ($Na_2SO_4$), concentrated and the residue flash chromatographed on silica gel and eluted with 1: 1 ether:hexane. The major spot was collected to afford 122 mg of 4 -chloro-2-(1-phenyl-1H-tetrazol-5-ylthiotaethyl) saccharin as a white solid, mp 175°–177° C. $^1$H nmr (300 MHz, $CDCl_3$): 7.813 (3H, m); 7.515 (5H, s); 5.710 (2H, s). IR (Kbr, $cm^1$): 3080 (w); 1740 (s); 1590 (w). FDMS: m/e 407 ($M^+$); 230 ($M^+$-PMT); 178 (1%, PMT).

EXAMPLE 5

The chloromethyl derivative prepared as in Example 3, (337 mg crude; maximum 1.27 mmol) was dissolved (to the extent possible) in acetone (10 ml). Sodium 1-phenyl-5-mercapto-1H-tetrazole (304 mg; 1.52 mmol; 1.2 equiv.) was added, and the reaction mixture was stirred at room temperature for 3 days. The mixture was diluted with MDC (50 ml), washed with water (3×25 ml), dried ($Na_2SO_4$), concentrated and filtered through a pad of silica gel (1:1 ether:hexane elution). The material thus obtained was chromatographed on flash silica gel and eluted with 1:1 ether:hexane to afford 44 mg (8.5%) of 4-chloro-2-(4-phenyl-5-thioxotetrazolin-1-ylmethyl) saccharin mp 158°–162° C. $^1$H nmr (300 MHz, $CDCl_3$): 7.981 (1H, d, J=7.12 Hz); 7.95 (2H, m); 7.887 (1H, t, J=6.74 Hz); 7.864 (1H, d, J=7.32 Hz); 7.567 (3H, m); 6.392 (2H, s). IR (KBr, CM$^1$): 1745 (s); 1185 (s). FDMS: m/e 407 (M$^+$); 230 (M$^+$-PMT).

EXAMPLE 6

A mixture of 2-(chloromethyl) saccharin (0.98 g, 4.2 mmol), 1-(3-acetamidophenyl)-5-mercapto-1H-tetrazole (1 g, 4.2 mmol) and potassium bicarbonate (0.84 g, 8.4 mmol) in methyl ethyl ketone (50 ml) was heated at 50° C. under nitrogen overnight. The reaction mixture was cooled, poured into dilute HCl/ice water (300 ml.), and the water was decanted from the semi-solid which solidified on trituration with hot ethyl acetate. The resultant white solid was recrystallized from acetonitrile (MeCN) with charcoaling, to afford 0.82 g of 2-[1-(3-acetamidophenyl)-1H-tetrazol-5-ylthiomethyl]saccharin as small white needles, mp 195°–196° C. decomp. $^1$H nmr (90 MHz, CDCl$_3$):2.05 (3H, s); 5.65 (2H, s). FDMS: m/e 430 (M$^+$).

Theor C, 47.43; H, 3.28; N, 19.52;

Found C, 47.02; H, 3.27; N, 19.53.

EXAMPLE 7

A mixture of 2-(bromomethyl) saccharin (2.7 g, 9.8 mmol), 1-(3-heptanamidophenyl)-5-mercapto-1H-tetrazole (3 g, 9.8 mmol) and potassium carbonate (3.4 g., 24.5 mmol) was heated under reflux in methyl ethyl ketone (50 ml) under nitrogen for 1 hour. The mixture was cooled and poured into a sodium bicarbonate/ice solution. The water layer was decanted from the resultant white semi-solid. The semi-solid was washed with water, then dissolved in hot acetonitrile, the solution treated with activated charcoal and filtered. The filtrate was freed of solvent under vacuum, and the resultant solid was chromatographed (silica gel-95:5 CH$_2$Cl$_2$:acetone) to give a clear oil. The oil was crystallized from hot ethanol to afford 1.6 g of 2-[1-(3-heptanamidophenyl)-1H-tetrazol-5-ylthiomethyl]saccharin as a white solid, mp 146°–147.5° C. $^1$H nmr (90 MHz, CDCl$_3$): 5.65 (2H, s). FDMS: m/e 500 (M$^+$).

Theor C, 52.79; H, 4.83; N, 16.79;

Found C, 52.44; H, 4.75; N, 16.64.

EXAMPLE 8

A mixture of 2-(bromomethyl) saccharin (3 g, 10.8 mmol) and the sodium salt of 5-mercapto-1-methyl-1H-tetrazole (1.49 g, 10.8 mmol) was heated under reflux in methyl ethyl ketone (75 ml) for 2 hours. The reaction mixture was cooled, poured into dilute sodium bicarbonate/ice solution and extracted with MDC (2x's). The combined organic extracts were dried (Na$_2$SO$_4$) and freed of solvent under vacuum. The crude product was chromatographed (silica gel-95:5 CH$_2$Cl$_2$:ether), and the resultant oil was crystallized from hot isopropanol to afford 2.7 g (80%) of 2-(1-methyl-1H-tetrazol-5-ylthiomethyl)saccharin as a white solid, mp 106°–110° C. $^1$H nmr (90 MHz, CDCl$_3$):5.55 (2H, s). FDMS: m/e 311 (M$^+$).

Theor C, 38.58; H, 2.91; N, 22.49;

Found C, 38.53; H, 2.79; N, 22.60.

EXAMPLE 9

A mixture of 2-(chloromethyl) saccharin (3 g, 12.9 mmol), 1-cyclohexyl-5-mercapto-1H-tetrazole (2.37 g, 12.9 mmol) and potassium carbonate (4.45 g, 32.2 mmol) was heated under reflux in methyl ethyl ketone (50 ml) for 1 hour. The reaction mixture was cooled, poured into dilute sodium bicarbonate/ice solution and extracted twice with ethyl acetate. The combined organic extracts were washed with water, dried (Na$_2$SO$_4$) and freed of solvent under vacuum. Chromatography (silica gel; MDC) afforded 2 g of 2-(1-cyclohexyl-1H-tetrazol-5-ylthiomethyl) saccharin as a white foam that was crystallized from hot cyclohexane, mp 103°–105° C. $^1$H nmr (90 MHz, CDCl$_3$):5.65 (2H, s). FDMS: m/e 379 (M$^+$).

Theor C, 47.48; H, 4.52; N, 18.46;

Found C, 47.84; H, 4.61; N, 18.36.

EXAMPLE 10

A mixture of m-chloroperbenzoic acid (0.43 g, 9,.67 mmol) and 2-(1-phenyl-1H-tetrazol-5-ylthiomethyl) saccharin (1 g, 2.67 mmol) in MDC was stirred at room temperature for 24 hours. TLC (95:5 CH$_2$Cl$_2$: ether) revealed the presence of starting sulfide. Additional peracid (0.2 g) was added and the mixture stirred for an additional 2 days. The reaction mixture was washed with sodium bicarbonate solution, dried (Na$_2$SO$_4$) and freed of solvent under vacuum. Chromatography (silica gel-95:5 CH$_2$Cl$_2$:ether) afforded a foam that was crystallized from ether to afford 0.52 g of 2-(1-phenyl-1H-tetrazol-5-ylsulfinylmethyl) saccharin as a white solid, mp 161°–162° C. $^1$H nmr (90 MHz, CDCl$_3$):5.5–6.0 (2H, q). FDMS: m/e 196 (M$^+$-PMT), 389 (M$^+$).

Theor C, 46.27; H, 2.85; N, 17.98;

Found C, 46.00; H, 2.83; N, 17.76.

EXAMPLE 11

A mixture of 2-bromomethyl-5-nitrosaccharin (2 g, 6.2 mmol) and 1-phenyl-5-mercapto-1H-tetrazole, sodium salt in methyl ethyl ketone (40 ml)/DMF (10 ml) was heated under reflux for 2 hours. The reaction mixture was cooled and poured into a dilute sodium bicarbonate/ice solution. The resultant white solid, isolated by filtration, was washed with water and air dried. The compound was sonicated with 50:50 MDC:acetone and filtered to remove soluble impurities. The remaining solid was recrystallized from 2:1 acetonitrile: ethanol to afford 1.5 g of 5-nitro-2-(1-phenyl-1H-tetrazol-5-ylthiomethyl) saccharin as an off white solid, mp 189°–190° C. $^1$H nmr (90 MHz, DMSO-d$_6$):5.75 (2H, s). FDMS: m/e 418 (M$^+$).

Theor C, 43.06; H, 2.41; N, 20.09;

Found C, 42.29; H, 2.43; N, 20.13.

EXAMPLE 12

A mixture of m-chloroperbenzoic acid (2.2 g, 12.8 mmol) and 2-(phenylsulfinylmethyl) saccharin (3.75 g, 11.6 mmol) in MDC (50 ml) was stirred at room temperature for 2 hours. An additional spatula of peracid was added, and stirring was continued for an additional 1 hour. m-Chlorobenzoic acid was removed by filtration and the solid was washed with a small amount of MDC. The filtrate was washed with sodium bicarbonate solution, dried (Na$_2$SO$_4$) and freed of solvent under vacuum. The resultant solid was recrystallized from 50:50 ethanol:acetonitrile to afford 2-(phenylsulfonylmethyl)saccharin as a white solid, mp 169°–171° C. $^1$H nmr (90 MHz, DMSO-d$_6$, CDCl$_3$):5.15 (2H, s). FDMS: m/e 196 (M$^+$-PMT).

Theor C, 49.84; H, 3.29; N, 4.15;

Found C, 49.92; H, 3.24; N, 4.13.

EXAMPLE 13

A mixture of m-chloroperbenzoic acid (0.9 g, 5.37 mmol) and 2-(2-pyrimidylthiomethyl) saccharin prepared by procedures similar to those of Examples 9 and 11 (1.5 g, 4.8 mmol) in MDC (75 ml) was stirred overnight at room temperature. The reaction mixture was washed with sodium bicarbonate solution, dried ($Na_2SO_4$) and freed of solvent under vacuum. Part of this crude product (0.5 g) was saved for direct conversion to the sulfone; the remaining material was chromatographed (silica gel-95:5 $CH_2Cl_2$:acetone). Recrystallization from ethanol:acetonitrile afforded 0.95 g of 2-(2-pyrimidylsulfinylmethyl)saccharin as white crystals, mp 197°–198 ° C. decomp. $^1H$ nmr (90 MHz, $CDCl_3$, DMSO-$d_6$) :5.1–5.5 (2H, q) .

Theor C, 44.57; H, 2.81; N, 13.00;

Found C, 44.67; H, 2.84; N, 12.97.

EXAMPLE 14

A mixture of m-chloroperbenzoic acid (0.4 g, 2.3 mmol) and the sulfoxide prepared in Example 13 (0.75 g, 2.3 mmol) in MDC (50 ml) was stirred at room temperature with TLC (95:5 MDC:acetone) monitoring. After 2 hours, some of the starting sulfoxide still remained; an additional spatula of peracid was added and the reaction was stirred overnight. Methylene chloride (100 ml) was added and the mixture was washed with sodium bicarbonate solution. The organic layer was dried ($Na_2SO_4$) and the solvent was removed under vacuum. Recrystallization of the residue from acetonitrile:ethanol afforded 0.95 g of 2-(2,pyrimidylsulfonylmethyl) saccharin as a white solid, mp 225°–227° C. decomp. $^1H$ nmr (90 MHz, DMSO-$d_6$):5.78 (2H, s). FDMS: m/e 196 ($M^+$-PMT), 339 ($M^+$).

Theor C, 42.47; H, 2.67; N, 12.38;

Found C, 42.20; H, 2.62; N 12.46.

EXAMPLE 15

A mixture of 2-(chloromethyl) saccharin (3 g, 12.9 mmol) and sodium p-nitrophenoxide (2.55 g, 12.9 mmol) in THF (50 ml) was heated overnight at 50° C. and then refluxed for 45 minutes. The reaction mixture was cooled, poured into a dilute sodium bicarbonate/ice solution and extracted twice with ethyl acetate. The combined organic extracts were washed with sodium bicarbonate solution and water, dried ($Na_2SO_4$), and taken to dryness in vacuo. Chromatography (silica gel; MDC) afforded an oil that was crystallized from hot cyclohexane/ether. The resultant solid was recrystallized from ethanol to afford 0.92 g of 2-(4-nitrophenoxymethyl)-saccharin as white shiny platelets, mp 162°–164° C. $^1H$ nmr (90 MHz, $CDCl_3$, DMSO-$d_6$):5.95 (2H, s). FDMS m/e 334 ($M^+$).

Theor C, 50.30; H, 3.02; N, 8.38;

Found C, 50.06; H, 2.91; N, 8.28.

EXAMPLE 16

5-Nitro-2-(1-phenyl-1H-tetrazol-5-ylthiomethyl) saccharin (4 g, 9.56 mmol) (Example 11) was dissolved in THF (250 ml) and placed in a Parr shaker bottle. Two spatulas of 10% palladium-on-charcoal catalyst were added under nitrogen, and the mixture was shaken under hydrogen (55 psi) for 2.5 days. The reaction mixture was filtered through Celite diatomaceous earth and filtrate mixed with water and extracted with MDC. The organic layer was dried ($Na_2SO_4$), freed of solvent under vacuum, and the resultant yellow foam was sonicated with warm ethanol, cooled and filtered. The desired 5-aminosaccharin derivative, 0.5 g, was isolated as a cream colored solid. FDMS: m/e 388 ($M^+$).

A mixture of the above 5-aminosaccharin derivative (0.5 g, 1.29 mmol) and 3,3-diphenylpropanoyl chloride (0.315 g, 1.29 mmol) in acetonitrile (50 ml) was heated under reflux for 2.5 hours. TLC (95:5 methylene chloride:acetone) analysis revealed the presence of some starting amine. A small additional amount of acid chloride was added, refluxing was continued for an additional 1.5 hours and the reaction mixture cooled and poured into ice water (400 ml). After 30 minutes, the mixture was filtered, and the resultant tan colored solid was washed with water and air dried. Chromatography on silica gel (95:5 MDC:ether) produced a foam that was crystallized from hot ethanol to yield 0.68 g of 5-(3,3-diphenylpropionamido)-2-(1-phenyl-1H-tetrazol-5-ylthiomethyl) saccharin as a white solid, mp 92°–93° C. decomp. FDMS: m/e 596 ($M^+$). $^1H$ nmr (90 mHz, $CDCl_3$) :3.25 (1H, d); 4.8 (2H, t); 5.6 (2H, s); 6.9–8.2 (m, Ar). NMR also revealed approximately two ethanol molecules of crystallization: 1.25 (t); 3.7 (q). Comb. anal.:

Theor for $C_{30}H_{24}N_6O_4S_2+2C_2H_5OH$: C, 59.28; H, 5.27; N, 12.2;

Found: C, 58.09; H, 5.15; N, 12.09.

EXAMPLE 17

Methyl 2-chloro-2-phenylthioacetate was prepared as reported in the literature: I. Fleming and J. Iqbal, Tetra. Lett., 24, 327 (1983); M. Campbell, et al., Tetra. Lett., 21, 3305 (1980).

Saccharin (10 g, 54.6 mmol) was dissolved in ethanol (500 ml) with slight warming. Thallous ethoxide (13.6 g, 54.6 mmol) was added dropwise, and the resultant heterogeneous mixture was stirred at room temperature for 2 hours, then cooled, filtered and the solid washed with cold ethanol. The greyish white, crystalline solid was dried under vacuum in a desiccator to yield 19.4 g (92%) of the thallium salt of saccharin.

A mixture of the thallium salt of saccharin (1.78 g, 4.6 mmol) and methyl 2-chloro-2-phenylthioacetate (1 g, 4.6 mmol) in DMF (25 ml) was stirred at 60° C. for 7 hours. The mixture was cooled and poured into ice water (400 ml). After 30 minutes, the mixture was filtered, and the solid was washed with water and air-dried. Chromatography on silica (MDC) afforded a clear oil that was crystallized from hot ethanol to yield 0.87 g (51%) of white needles of methyl 2-phenylthio-2-(2-saccharinyl) acetate, mp 144°–146° C. $^1H$ nmr (90 MHz, $CDCl_3$): 3.8 (3H, s); 5.95 (1H, s); 7.2–8.15 (9H, m). FDMS: m/e 363 ($M^+$).

A solution of methyl 2-phenylthio-2-(2-saccharinyl) acetate (2 g, 5.5 mmol) and sulfuryl chloride (0.74 g, 5.5 mmol) in MDC (50 ml) was stirred at room temperature for 2 hours. Solvent was removed under vacuum, and the yellow oil was crystallized from warm ethanol to give 0.94 g of product. NMR revealed greater than 50% starting material. An additional amount of starting material (1 g, 2.75 mmol) was added to the crude product mixture and it was redissolved in methylene chloride. Sulfuryl chloride (0.5 ml) was again added and the mixture was stirred at room temperature for about 12 hours. Work up as above afforded 0.66 g of crude methyl 2-chloro-2-(2-saccharinyl) acetate that was used immediately in the next step.

A mixture of this chloride (0.66 g crude mixture) and 1-phenyl-5-mercapto-1H-tetrazole in the form of the sodium salt (0.44 g, 2.2 mmol) was heated under reflux in methyl ethyl ketone (25 ml) for 4 hours. After stirring at room temperature for 2 days, the reaction mixture was poured into ice water. The tan solid isolated by filtration was washed with water and air-dried. Chromatography on silica gel (MDC) yielded an off-white foam that was crystallized from ethanol to yield 0.36 g of methyl 2-(1phenyl-1H-tetrazol-5- ylthio)-2-(2-saccharinyl) acetate as a white crystalline solid, mp 160°–162° C. $^1$H nmr (90 MHz, CDCl$_3$):3.8 (3H, s) ; 7.05 (1H, s); 7.4–8.1 (9H, m). FDMS: m/e 431 (M$^+$).

Theor for C$_{17}$H$_{13}$N$_5$O$_5$S$_2$: C, 47.33; H, 3.04; N, 16.23; Found: C, 47.15; H, 3.09; N, 16.30.

EXAMPLE 18

To a suspension of 6.0 g (0.03 mol) of cuprous iodide in 100 ml of THF was added 25 ml of dimethyl sulfide, and the resulting yellow solution was cooled to –78° C. and treated dropwise with a solution of 23 ml (0.06 mol) of a 3.0M solution of phenyl magnesium bromide in diethyl ether. The resulting pale yellow-orange solution was stirred at –78° C. under nitrogen for one hour and then treated with 3.02 g (0.03 mol) of 2-cyclohexenone in 10 ml of THF. The resulting mixture was allowed to warm to 0° C. over a two hour period, recooled to –78 ° C., treated with 15 ml of hexamethylphosphoramide, stirred for thirty minutes, treated with 8.0 g (0.09 mol) of methyl cyanoformate and allowed to warm to ambient temperature overnight. The reaction mixture was poured into 100 ml of 2N hydrochloric acid, and the organic phase was separated and the aqueous phase back extracted with MDC. The combined organic extracts were taken to dryness in vacuo, and the residue triturated with saturated ammonium chloride, then with water, then with brine and taken to dryness once again to give 3.2 g of methyl 2-phenylcyclohexan-6-one carboxylate as an oil.

The latter (3.0 g, 0.013 mol), 4.8 g (0.039 mol) of benzyl mercaptan and 1.0 g of Amberlyst®-15 resin (Rohm and Haas) in chloroform was heated under reflux for twenty hours, the mixture treated with an additional 1.5 g of the resin and heated for an additional four hours. The mixture was then cooled to ambient temperature, filtered, the filtrate taken to dryness in vacuo, the residue triturated with hexane and the solid collected by filtration to give 0.85 g (19%) of a mixture of methyl 2-benzylthio-6-phenylcyclohex-2-ene carboxylate and methyl 2-benzylthio-6-phenylcyclohex-1-ene carboxylate, 0.6 g (0.0018 mol) of which was heated with 2.0 g of 2,3-dichloro-5,6-dicyanobenzoquinone in 25 ml of toluene with stirring under nitrogen for twenty-four hours. The mixture was filtered through a pad of silica gel, eluting with 2:1 MDC:hexane and the eluate taken to dryness to give 0.3 g (67%) of methyl 2-benzylthio-6-phenylbenzoate.

The latter 0.52 g (0.0016 mol) dissolved in 10 ml of MDC was diluted with 20 ml of acetic acid and 5 ml of water, the mixture cooled to –10° C., and chlorine gas was bubbled through the mixture until the exothermic reaction subsided. The mixture was then stirred for ten minutes and taken to dryness in vacuo to give 0.41 g (85%) of methyl 2-chlorosulfonyl-6-phenylbenzoate which was dissolved in 10 ml of THF and added to 25 ml of a solution of concentrated ammonium hydroxide while cooling in an ice/acetone bath. The reaction mixture was extracted with MDC, the organic phase discarded, and the aqueous layer acidified to pH 1 with concentrated hydrochloric acid and extracted with MDC. The organic extracts, on washing with brine, drying and evaporation to dryness, afforded 0.33 g (97%) of 4-phenylsaccharin.

Following a procedure similar to that described in Example 21, the latter (0.33 g, 0.0012 mol) was reacted with 0.3 g (0.0019 mol) of chloromethyl phenyl sulfide in 15 ml of toluene in the presence of 0.08 g (0.0025 mol) of tetrabutyl-ammonium bromide and the product, 2-phenylthiomethyl-4-phenylsaccharin (0.48 g, 100%), treated with sulfuryl chloride in MDC to give 0.36 g (95%) of 2-chloromethyl-4-phenyl-saccharin.

EXAMPLE 19

A solution of 2.2 g (0.0071 mol) of 2-(phenyl-chloromethyl)saccharin and 1.4 g (0.0071 mol) of the sodium salt of 1-phenyl-5-mercaptotetrazole in 30 ml of DMF was heated at 55° for three and one half hours, then stirred at ambient temperature for about sixteen hours and poured into ice water containing dilute sodium bicarbonate. The solid which separated was collected, washed with water, air dried and chromatographed on silica gel, eluting with 98:2 MDC: diethyl ether, to give 2 g (63%) of 2-(1-phenyl-1H-tetrazol-5-ylthiophenylmethyl) saccharin, mp 192°–193 ° C.

EXAMPLE 20

A solution of 4.53 g (0.022 mol) of the sodium salt of saccharin and 5 g (0.022 mol) of 1-phenyl-4-chloromethyl-tetrazolin-5-thione in 50 ml of DMF was heated at 130° for four hours, then cooled and poured into ice water. The solid which separated was collected, washed with water, dried and chromatographed on silica gel, eluting with MDC, to give 4.8 g (58%) of 2-(1-phenyl-5-thioxotetrazolin-4-ylmethyl) saccharin, mp 140°–142° C.

EXAMPLE 21

A mixture of 3.27 g (0.012 mol) of 4-bromosaccharin [Japanese Pat. Publcn. 58/79,034, published May 12, 1983; C. A. 100, 7773w (1984)], 1.63 g (0.015 mol) of potassium t-butoxide, 0.39 g (0.0012 mol) of tetrabutylammonium bromide and 3.0 ml (0.022 mol) of chloromethyl phenyl sulfide in 100 ml of toluene was heated under reflux under a nitrogen atmosphere for eight hours and then at ambient temperature for about sixteen hours. The reaction mixture was then cooled, diluted with ethyl acetate and the organic layer washed with bicarbonate, water and brine and then dried over magnesium sulfate and taken to dryness in vacuo. The residual solid was recrystallized from toluene-hexane to give 3.86 g (84%) of 4-bromo-2-phenylthiomethylsaccharin, mp 174.5°–178° C.

To a solution of the latter (3.27 g, 0.0085 mol) in 85 ml of MDC was added, dropwise with stirring, 1.02 ml (0.0127 mol) of sulfuryl chloride. The mixture was stirred at ambient temperature for an hour and a half, concentrated in vacuo and the residue triturated with hexane and filtered to give 2.61 g of crude product which was recrystallized from toluene-hexane to give 2.24 g (85%) of 2-chloromethyl-4-bromosaccharin, mp 157°–159° C.

EXAMPLE 22A

To a solution of 8.0 ml (0.053 mol) of tetramethyl-ethylenediamine (TMEDA) in 350 ml of THF at –70° C. was added 42 ml (0.055 mol) of a 1.3M solution of s-butyl lithium in hexane and the mixture was stirred for fifteen minutes. To the solution was added dropwise with stirring a solution of 10.36 g (0.050 mol) of 2-methoxy-N,N-diethylbenzamide in 150 ml of THF while maintaining the temperature at –60° C. or below and sulfur dioxide then bubbled into the reaction mixture, keeping the reaction temperature below –50° C. until the reaction mixture was acid to wet litmus paper. The mixture was then stirred at ambient temperature for two hours, diluted with 450 ml of hexane, and the solid material which had separated was collected, dissolved in 200 ml of water and the mixture treated with 65 g of sodium acetate, and 21.5 g (0.19 mol) of hydroxylamine-O-sulfonic acid was added in portions with stirring. The white solid which separated was collected and dried to give 7.04 g (49%) of 2-aminosulfonyl-6-methoxy-N,N-diethylbenzamide, mp 190°–194.5° C.

A mixture of the product (4.3 g, 0.015 mol) in 75 ml of dioxane and 25 ml of concentrated hydrochloric acid was heated on a steam bath for 70 hours, then cooled, concentrated in vacuo, diluted with water and ice and rendered strongly basic with concentrated sodium hydroxide. Extraction of the mixture with MDC and isolation of the product from the organic extracts afforded 1.29 g (40%) of 4-methoxysaccharin. In an alternative, and preferred, procedure, cyclization of 2-aminosulfonyl-6-methoxy-N,N-diethylbenzamide to 4-methoxy-saccharin in 65% yield was carried out in refluxing glacial acetic acid for six and a half hours.

Following a procedure similar to that described in Example 21 above, 1.14 g (0.0053 mol) of the latter was reacted with 1.31 ml (0.0097 mol) of chloromethyl phenyl sulfide in toluene in the presence of 0.72 g (0.0064 mol) of potassium t-butoxide and 174 mg (0.00054 mol) of tetrabutyl-ammonium bromide to give 1.23 g (69%) of 4-methoxy-2-phenyl-thiomethylsaccharin, mp 152.5°–154.5° C. (from ethyl acetate-hexane), 1.02 g (0.003 mol) of which was treated with 0.36 ml (0.0045 mol) of sulfuryl chloride in MDC to give 282 mg (36%) of 2-chloromethyl-4-methoxysaccharin, mp 169°–174° C.

EXAMPLE 22B

To a solution of 4.74 ml (0.031 mol) of tetramethylethylenediamine in 300 ml of THF (passed through alumina prior to use) was added 5.8 g (0.03 mol) of 2-ethyl-N,N-diethylbenzamide. The solution was cooled to –78° C. and treated with a solution of 34.9 ml (0.031 mol) of a 0.9M solution of s-butyl lithium in cyclohexane. When addition was complete, the mixture was stirred for twenty minutes and then treated with a solution of 3.2 ml (0.04 mol) of ethyl iodide while maintaining the temperature at –78 ° C. The temperature was then allowed to rise to ambient temperature and the mixture stirred for about sixteen hours and then poured into water. The resulting oil was separated and chromatographed on silica gel, eluting with 10% ethyl acetate/hexane to give 2.86 g (43%) of 2-sec.-butyl-N,N-diethylbenzamide as a yellow oil.

Following a procedure similar to that described in Example 22A above the latter (10.45 g, 0.045 mol), dissolved in 70 ml of THF, was added to a solution of 39.2 ml (0.047 mol) of a 1.2M solution of s-butyl lithium in cyclohexane and 7.1 ml (0.047 mol) of tetramethylethylenediamine in 250 ml of THF while maintaining the temperature at –78° C. When addition was complete the mixture was stirred for an additional one half hour at –78° C. and then treated with sulfur dioxide at –70° C. and then allowed to warm to room temperature. The mixture was taken to dryness in vacuo, and the residue was dissolved in water and added with stirring to a cold solution of 15.2 g (0.134 mol) of hydroxylaminesulfonic acid and 15.4 ml (0.134 mol) of 35% sodium hydroxide to give 10.1 g (72%) of 2-aminosulfonyl-6 -sec.-butyl-N,N-diethylbenzamide.

The latter (6.83 g, 0.22 mol) was dissolved in 100 ml of glacial acetic acid and the solution heated under reflux for thirteen hours and then taken to dryness. The residue was triturated with diethyl ether and collected by filtration to give 5.7 g (83%) of the diethylammonium salt of 4-sec.-butylsaccharin.

The latter (3.0 g, 0.0096 mol), on reaction with 1.13 ml (0.012 mol) of chloromethyl phenyl sulfide in toluene, afforded 3.47 g (100%) of 2-phenylthiomethyl-4-sec.-butylsaccharin.

Reaction of the latter (3.2 g, 0.0097 mol) with 2.3 ml (0.029 mol) of sulfuryl chloride in 20 ml of MDC afforded 2.4 g (87%) of 2-chloromethyl-4-sec.-butylsaccharin.

EXAMPLE 22C

To a solution of 9.3 ml (0.058 mol) of tetramethylethylenediamine in 340 ml of THF at –78° C was added 52 ml of a 1.1M solution (0.057 mol) of s-butyl lithium in THF. The solution was then treated with a solution of 11.37 g (0.052 mol) of 2-propyl-N,N-diethylbenzamide in 75 ml of THF at –78° C. and the solution stirred for fifteen minutes and then treated with a solution of 8.3 ml of (0.104 mol) of ethyl iodide in THF. The solution was stirred for an hour and a half at –78° C. and then quenched by the addition of saturated ammonium chloride added dropwise at –78° C. The mixture was then allowed to warm to ambient temperature, diluted with diethyl ether, washed first with dilute hydrochloric acid, then with water, then with saturated sodium bicarbonate, then with brine dried and taken to dryness to give 12.91 g of crude product which was chromatographed on silica gel, eluting with 10% ethyl acetate/hexane to give 3.23 g (25%) of 2-(3-pentyl)-N,N-diethylbenzamide as a yellow oil.

Following a procedure similar to that described in Example 22A above, the latter (3.05 g, 0.0115 mol) in THF was reacted with 10.5 ml (0.126 mol) of a 1.2M solution of s-butyl lithium in THF in the presence of 2.1 ml (0.014 mol) of tetramethylethylenediamine. The resulting lithium salt was then reacted first with sulfur dioxide and then with sodium hydroxylaminesulfonate to give 1.97 g (52%) of 2-aminosulfonyl-6-(3-pentyl)-N,N-diethylbenzamide as pale yellow crystalls, mp 118°–120° C. (soft 102°), 1.84 g (0.0056 mol) of which was cyclized in 22 ml of refluxing glacial acetic acid to give 1.28 g (70%) of the diethylammonium salt of 4-(3-pentyl) saccharin, mp 107.5°–109.5° C.

The latter (0.0037 mol), on reaction with 0.74 ml (0.0055 mol) of chloromethyl phenyl sulfide in the presence of 116 mg (0.0004 mol) of tetrabutylammonium bromide in 45 ml of toluene, afforded 1.93 g of 2-phenylthiomethyl-4-(3-pentyl)-saccharin as a pale yellow oil, 1.93 g (0.0037 mol) of which, on reaction with 0.59 ml (0.0073 mol) of sulfuryl chloride in 37 ml of MDC, afforded 1.2 g of 2-chloromethyl-4-(3-pentyl)-saccharin as a pale yellow oil.

EXAMPLES 22D–22N

Following a procedure similar to that described above in Example 22A, substituting for the 2-methoxy-N,N-diethylbenzamide used therein an appropriate 2-$R_3$-$R_4$-substituted-N,N-diethylbenzamide, the following 2-halomethyl-4-$R_3$-$R_4$-substituted saccharins listed in TABLE A were prepared via the corresponding 2-phenylthiomethylsaccharins. Wherever available, the melting point, recrystallization solvent and yield are given for each of the 2-unsubstituted saccharins, the 2-phenylthiomethylsaccharins and the 2-chloromethylsaccharins in columns headed "mp/Solv." and "Yield". In all instances, the intermediate 2-phenylthiomethylsaccharins were used directly in the subsequent step without further characterization or purification.

TABLE A

| Ex. | $R_3/R_4$ | Sacc. mp/Solv. | Sacc. Yield | 2-$C_6H_5SCH_2$-Sacc. mp/Solv. | 2-$C_6H_5SCH_2$-Sacc. Yield | 2-$ClCH_2$-Sacc. mp/Solv. | 2-$ClCH_2$-Sacc. Yield |
|---|---|---|---|---|---|---|---|
| 22D | H<br>7-Cl | 260–262 | 93 | — | 100 | 158.0–160.0<br>i-PrOH | 41 |
| 22E | $CH(CH_3)_2$<br>H | 177.0–178.0<br>MeOH | 88 | — | 100 | 96.0–98.0<br>i-PrOH-Cyc. hex. | 20 |
| 22F | $CH_3O$<br>5-$CH_3O$ | (a) | 64 | — | 100 | 190.0–192.0 | 76 |
| 22G | $COOCH_3$<br>H | (b)<br>EtOAc-hex. | 76 | — | 65 | 186.0–187.0 | |
| 22H | $C_2H_5O$<br>H | (a) | 96 | — | 95 | 139.0–140.0 | |
| 22I | $(CH_3)_2CHO$<br>H | | 87 | — | 75 | 142.5–143.5 | 94 |
| 22J | $CH_3O$<br>6-$CH_3O$ | (a) | 94 | — | 89 | | |
| 22K | $CH(CH_3)$—$(C_2H_5)$<br>H | | 83 | — | 100 | — | 87 |
| 22L | $C_2H_5$<br>5,7-$(CH_3O)_2$ | 240–243<br>i-PrOH | 67 | — | 52 | 163–158<br>hexane | 99 |
| 22M | $CH(C_2H_5)_2$<br>H | 107.5–109.5<br>Me t-Bu ether:hex. | 70 | — | 100 | oil | 100 |
| 22N | $C_6H_5$<br>H | (c) | | — | 100 | — | 100 |

(a) Isolated and used in the next step as the diethylammonium salt.
(b) The 2-unsubstituted-saccharin was prepared by cyclization of dimethyl 3-aminosulfonylphthalate in methanol in the presence of a molar equivalent of sodium methoxide. The phthalate ester was prepared by diazotization of dimethyl 3-aminophthalate, decomposition of the diazonium salt with sulfur dioxide in the presence of cupric chloride and reaction of the resulting dimethyl 2-chlorosulfonylphthalate with ammonia. (84% yield overall).
(c) See Example 21B for preparation of 2-unsubstituted-saccharin.

EXAMPLE 23

Following a procedure similar to that described in Example 1, reaction of 18.3 g (0.1 mol) of saccharin with 70 ml of 37% formalin in ethanol afforded 3.58 g (70%) of 2-hydroxymethylsaccharin, 25 g (0.117 mol) of which was reacted with 63.3 g (0.234 mol) of phosphorus tribromide in diethyl ether to give 29.8 g (92%) of 2-bromomethylsaccharin, mp 155°–157° C.

EXAMPLE 24

To a solution of 4 g (0.0175 mol) of 6-nitro-saccharin in 240 ml of ethanol was added 4.4 g (0.0175 mol) of thallium ethoxide, and the mixture was allowed to stand at room temperature for one hour, cooled for about 16 hours and the precipitated solid collected and dried to give 7.6 g (100%) of the thallium salt of 6-nitrosaccharin. The product was suspended in 50 ml of DMF and the mixture treated with 3.07 g (0.0194 mol) of chloromethyl phenyl sulfide, the mixture warmed at about 63° C. for five hours, allowed to stand at ambient temperature for about 16 hours, and then poured into ice water. The crude product, obtained by filtration, was stirred in MDC and filtered to remove thallium salts. The filtrate was freed of solvent, and the resultant pale yellow solid was sonicated with warm ethanol and once again collected and dried to give 4.6 g (75%) of 6-nitro-2-phenylthio-methylsaccharin, mp 161°–163° C. The latter, on reaction with sulfuryl chloride in MDC using the procedure described above in Example 17 afforded 3.7 g of 2-chloromethyl-6-nitrosaccharin.

EXAMPLE 25A

A solution of 49.8 g (0.199 mol) of 2-hydroxy-5-(1,1,3,3-tetramethylbutyl) benzoic acid in 200 ml of methanol was heated to 50° C. and then treated dropwise with about 80 g of sulfuric acid at a rate to maintain the reaction under reflux. The reaction mixture was heated under reflux for an additional 11 hours, then cooled and partitioned between water and ethyl acetate. The organic layer was washed with saturated sodium bicarbonate, then with brine, dried over sodium sulfate and taken to dryness to given 48.6 g (92%) of methyl 2-hydroxy-5-(1,1,3,3-tetramethylbutyl) benzoate.

The latter dissolved in 250 ml of DMF was treated first with 40.4 g (0.36 mol) of 1,4-diazabicyclo[2.2.2]octane followed by 33.4 g (0.27 mol) of dimethyl thiocarbamoyl chloride and 100 ml of DMF. The reaction mixture was heated at 45° C. for about eight hours, cooled, poured into ice/water and concentrated hydrochloric acid and then extracted with ethyl acetate. The combined organic extracts were washed with dilute hydrochloric acid, then with sodium bicarbonate and then with brine, dried and taken to dryness to give 48.2 g (76%) of methyl 2-(N,N-dimethylthiocarbamyloxy)-5-(1,1,3,3-tetramethylbutyl) benzoate which was heated at 220° C. for 15 hours, then cooled, dissolved in toluene and chromatographed on silica, eluting with 1:9 ethyl acetate:toluene, to give 3.6 g (14%) of methyl 2-N,N-dimethylcarbamylthio)-5-(1,1,3,3-tetramethylbutyl) benzoate.

A solution of the latter (0.025 mol) in 40 ml of MDC was treated, with stirring, with 80 ml of glacial acetic acid, followed by 16 ml of water. The reaction mixture was cooled to 0° C., and chlorine was bubbled through the reaction mixture for about five minutes while maintaining the temperature between 5° and 24° C. The reaction was stirred for an additional 30 minutes, concentrated in vacuo, and the remaining solution poured into ice water. Extraction of the mixture with ethyl acetate and isolation of the product from the combined organic extracts afforded 6.8 g (78%) of methyl 2-chlorosulfonyl-5-(1,1,3,3-tetramethylbutyl) benzoate.

The product (9.0 g, 0.026 mol) was dissolved in THF and added to 100 ml of concentrated ammonium hydroxide with cooling in an ice bath. The resulting solution was stirred for about 16 hours, then concentrated in vacuo and the concentrated solution acidified to pH 3 with concentrated hydrochloric acid. The mixture was stirred for several hours, and the separated solid collected, washed with water and dried to give 9.0 g of 5-(1,1,3,3-tetramethylbutyl)saccharin, mp 213°–215° C.

Following a procedure similar to that described in Example 17, 9.0 g (0.30 mol) of the product was reacted with thallium ethoxide in ethanol and the resulting thallium salt reacted with 3.33 g (0.021 mol) of chloromethyl phenyl sulfide in DMF to give 5.76 g (66%) of 2-phenylthiomethyl-5-(1,1,3,3-tetramethylbutyl)saccharin, 3.3 g (0.007 mol) of which was treated with 0.944 g of sulfuryl chloride in MDC to give 1 g (41%) of 2-chloromethyl-5-(1,1,3,3-tetramethylbutyl)-saccharin.

EXAMPLE 25B

Following a procedure similar to that described Example 25A above, 15.5 g (0.086 mol) of ethyl 2-hydroxy-6-methylbenzoate was reacted with 15.9 g (0.129 mol) of N,N-dimethylchlorothiocarbamate in the presence of 19.3 g (0.172 mol) of 1,4-diazabicyclo[2.2.2]octane in DMF to give 22.1 g (96%) of ethyl 2-N,N-dimethylthiocarbamyloxy)-6-methyl-benzoate which was heated at 220° C. for about 10 hours. The product was purified by chromatography on silica gel in MDC to give ethyl 2-(N,N-dimethylcarbamylthio)-6-methylbenzoate as a red-brown oil.

A solution of the latter (22.6 g, 0.0844 mol) in 170 ml of MDC was treated with 340 ml of glacial acetic acid and 68 ml of water while cooling in an ice/acetone bath, and chlorine was bubbled through the reaction mixture for 10–15 minutes. The reaction vessel was evacuated to remove excess chlorine and MDC and the mixture poured into water and partitioned between MDC and water. The oranic layer, on drying and evaporation to dryness, afforded 19 g of ethyl 2-chloro-sulfonyl-6-methylbenzoate, 5 g (0.019 mol) of which was reacted with concentrated ammonium hydroxide in THF to give 6.1 g (67%) of 4-methylsaccharin.

Following a procedure similar to that described in Example 17 above, the product (10.1 g, 0.0512 mol) was converted to the thallium salt by reaction with 12.8 g (0.0512 mol) of thallium ethoxide in ethanol and the thallium salt reacted with 6.7 g (0.0427 mol) of chloromethyl phenyl sulfide in DMF to give 6.85 g (50%) of 2-phenylthiomethyl-4-methylsaccharin.

Reaction of the latter (6.7 g, 0.021 mol) with sulfuryl chloride in MDC afforded 4.9 g (95%) of 2-chloromethyl-4-methylsaccharin.

EXAMPLE 26A

A mixture of 75 g (0.36 mol) of 3,3-dithiobispropionic acid, 102 ml of thionyl chloride and a catalytic amount of pyridine was stirred for about 24 hours and then evaporated to dryness in vacuo. The residue was treated with MDC and evaporated to dryness again to remove residual thionyl chloride and pyridine to give 87 g (98%) of the corresponding bis acid chloride, 44.8 g (0.18 mol) of which was dissolved in THF and added dropwise to a solution of 77.16 g (0.72 mol) of benzylamine in THF. The mixture was stirred for two hours at 40°–45° C., cooled and the precipitated solid collected, washed with water and dried to give 59 g (84%) of 3,3-dithiobispropionic acid N,N'-dibenzylcarboxamide, mp 162°–165° C.

Reaction of 7.0 g (0.018 mol) of the latter with 10.25 g (0.076 mol) of sulfuryl chloride in MDC gave a mixture of 2-benzyl-2H-isothiazol-3-one and 5-chloro-2-benzyl-2H-isothiazol- 3-one which were largely separated from one another by sonication in MDC (which solubilized most of the former). The insoluble material was collected by filtration and chromatographed on silica gel with MDC. There was thus obtained 5-chloro-2-benzyl-2H-isothiazol-3-one, mp 58°–68° C.

A solution of 10 g (0.044 mol) of the latter in MDC was cooled to 0° C. and the solution treated with 7.6 g (0.044 mol) of 3-chloroperbenzoic acid, the mixture stirred for 10 minutes and then treated with a second 7.6 g portion of the perbenzoic acid. The reaction mixture was filtered, the filter washed with MDC and the filtrate washed with saturated sodium bicarbonate, then with brine, dried over sodium sulfate and taken to dryness and the residue chromatographed in MDC on silica gel, the product being eluted with 50:50 hexane:MDC, to give 7.15 g (46%) of 5-chloro-2-benzyl-2H-isothiazol-3-one-1-oxide.

A solution of 1.1 g (0.0045 mol) of the latter in 8 ml of benzene was treated with 0.55 g (0.0051 mol) of 2-methoxyfuran and the solution heated in a pressure bottle at 70° C. for 1½ hours and then cooled and the solid collected, washed with benzene and dried to give 2-benzyl-7-hydroxy-4-methoxybenzisothiazol-3-one-1-oxide, mp 235°–237° C.

A mixture of the product (1.85 g, 0.006 mol), 2.48 g (0.018 mol) of potassium carbonate and 1.70 g (0.012 mol) of methyl iodide in acetone was heated under reflux for 1½ hours and then cooled and poured into water. The solid which separated was collected by filtration, washed with water and dried to give 1.70 g (89%) of 2-benzyl-4,7-dimethoxy-benzissothiazol-3-one-1-oxide, 1.13 g (0.0035 mol) of which was oxidized with 1.20 g (0.007 mol) of 3-chloroperbenzoic acid in MDC using the procedure described above to give 1.03 g (88%) of 2-benzyl-4,7-dimethoxysaccharin.

A mixture of 2.07 g (0.0062 mol) of the product, 1.37 g (0.02 mol) of ammonium formate and 1.5 g of 10% palladium-on-charcoal catalyst in 80 ml of methanol was heated under reflux for one hour, then cooled and filtered, and the filtrate taken to dryness to give 0.92 g (57%) of the ammonium salt of 4,7-dimethoxysaccharin.

A solution of 1.11 g (0.0042 mol) of the ammonium salt was dissolved in DMF, 0.67 g (0.0042 mol) of chloromethyl phenyl sulfide was added, and the solution heated under reflux for eight hours and then cooled and poured into ice water. The solid which separated was collected, washed with water and dried to give 0.50 g (33%) of 2-phenylthiomethyl-4,7-dimethoxysaccharin.

Reaction of the latter (0.5 g, 0.0013 mol) with sulfuryl chloride in MDC using the procedure described above in Example 17 afforded 0.22 g (58%) of 2-chloromethyl-4,7-dimethoxysaccharin.

EXAMPLES 26B AND 26C

Following a procedure similar to that described in Example 26A, other 2-chloromethylsaccharin derivatives were prepared as follows:

EXAMPLE 26B

Reaction of 5.8 g (0.024 mol) of 5-chloro-2-benzyl-2H-isothiazol-3-one with 3.76 g (0.0335 mol) of 2-ethoxyfuran afforded 3.05 g (40%) of 2-benzyl-4-ethoxy-7- hydroxybenzisothiazol-3-one-1-oxide, 5.7 g of which was reacted with 3.6 g (0.0197 mol) of 2-[2-methoxyethoxy] ethyl bromide in the presence of 4.95 g (0.0358 mol) of potassium carbonate in 125 ml of methyl ethyl ketone and 25 ml of DMF to give 7.0 g (93%) of 2-benzyl-4-ethoxy-7-[2-(2-methoxyethoxy)ethoxy]benzisothiazol-3-one-1-oxide, which was oxidized as before with 3-chloroperbenzoic acid in MDC to give 2-benzyl-4-ethoxy-7-[2-(2-methoxyethoxy) ethoxy]saccharin. Debenzylation of 6.6 g (0.015 mol) of the latter with 3.34 g (0.053 mol) of ammonium formate in the presence of 6.4 g of 10% palladium-on-charcoal catalyst in methanol afforded the ammonium salt of 4-ethoxy-7-[2-(2-methoxyethoxy) ethoxy]saccharin, which was reacted with 2.38 g (0.015 mol) of chloromethyl phenyl sulfide in 100 ml of DMF to give 1.46 g (21%) of 2-phenylthiomethyl-4-ethoxy-7-[2-(2-methoxyethoxy)ethoxy]saccharin, mp 73°–75° C. (from isopropanol). Treatment of 1.4 g (0.0029 mol) of the product with 0.4 g (0.0029 mol) of sulfuryl chloride in MDC afforded 1.16 g (100%) of 2-chloromethyl-4-ethoxy-7-[2-(2-methoxyethoxy) ethoxy]saccharin.

EXAMPLE 26C

Reaction of 3.03 g (0.01 mol) of 2-benzyl-7-hydroxy-4-methoxybenzisothiazol-3-one-1-oxide (Example 26A) with 2.01 g (0.011 mol) of 2-(2-methoxyethoxy) ethyl bromide in methyl ethyl ketone in the presence of 2 g (0.015 mol) of potassium carbonate afforded 2.58 g (64%) of 2-benzyl-4-methoxy-7-[2-(2-methoxyethoxy) ethoxy]benzisothiazol-3-one-1-oxide, which, on oxidation with 1.1 g (0.0063 mol) of 3-chloroperbenzoic acid in MDC, gave 2-benzyl-4-methoxy-7-[2-(2-methoxyethoxy)-ethoxy]saccharin. Debenzylation of 0.25 g (0.0006 mol) of the product with 0.13 g (0.0021 mol) of ammonium formate in methanol in the presence of 0.25 g of 10% palladium-on-charcoal gave 0.21 g (100%) of the ammonium salt of 4-methoxy-7-[2-(2-methoxyethoxy)ethoxy]saccharin. Reaction of 1.4 g (0.004 mol) of the ammonium salt with 0.63 g (0.004 mol) of chloromethyl phenyl sulfide in DMF afforded 2-phenylthio-methyl-4 -methoxy-7-[2-(2-methoxyethoxy) ethoxy]saccharin, which, on reaction with sulfuryl chloride in MDC, afforded 0.53 g (35%) of 2-chloromethyl-4-methoxy-7-[2-(2-methoxyethoxy) ethoxy]saccharin.

EXAMPLE 27

A solution of 1.89 g (0.011 mol) of diethylamino sulfur trifluoride (DAST) in 20 ml of MDC was added to a suspension of 2.13 g (0.01 mol) of 2-hydroxymethylsaccharin in 25 ml of MDC while maintaining the reaction mixture at –78° C.

The reaction mixture was stirred at –78° C. for one hour, the temperature was then allowed to slowly rise to ambient temperature and the mixture stirred for 16 hours and then poured into ice-water. The organic layer was separated and washed with water, dried over magnesium sulfate and taken to dryness to give 2.2 g of product which was recrystallized from ethyl acetate to give 1.6 g (74%) of 2-fluoromethylsaccharin, mp 96°–98° C.

EXAMPLE 28A

To a solution of 0.5 g (0.0025 mol) of 4-methylsaccharin in THF cooled to –78° C. by a dry ice/acetone bath was added, dropwise with stirring, a solution of 5.2 ml of a 1.3M solution of s-butyl lithium in THF. The mixture was stirred an additional hour at –78° C. and then treated with 0.16 ml (0.025 mol) of methyl iodide over a 1½ hour period. The mixture was stirred for an hour and 45 minutes, quenched in 25 ml of 1N hydrochloric acid, the reaction mixture rendered basic, the aqueous mixture extracted with chloroform and then acidified and extracted with ethyl acetate. The combined organic extracts were washed with 10% sodium thiosulfate, then with brine, dried over sodium sulfate and taken to dryness to give a product, whose PMR spectrum indicated a mixture consisting of 74% of 4-ethylsaccharin and 21% of 4,7-dimethylsaccharin.

Following a procedure similar to that described in Example 17 above, the crude material (0.47 g, 0.022 mol) was reacted with 0.24 ml (0.0028 mol) of chloromethyl phenyl sulfide in toluene in the presence of tetrabutylammonium bromide, and the product chromatographed on silica gel, eluting with MDC, 5 ml fractions being collected. The first 420 ml of eluate were discarded. The next 20 fractions, on evaporation, afforded 0.07 g of material, predominantly the 4,7-dimethylsaccharin, which was set aside. The next 25 fractions afforded 0.37 g of 2-phenylthiomethyl-4-ethylsaccharin, which was reacted with sulfuryl chloride in MDC to give 0.19 g (66%) of 2-chloromethyl-4-ethylsaccharin.

EXAMPLE 28B

Following a procedure similar to that described in Example 28A 10 g (0.051 mol) of 4-methylsaccharin was reacted with 86 ml (0.10 mol) of a 1.18M solution of s-butyl lithium in THF and the resulting solution treated with 4.5 ml (0.050 mol) of ethyl iodide to give 10.15 g (89%) of 4-propylsaccharin, which on reaction with 5.32 ml (0.056 mol) of chloromethyl phenyl sulfide in toluene in the presence of tetrabutylammonium bromide afforded a 65% yield of 2-phenyl-thiomethyl-4-propylsaccharin as an oil, 1.8 g (0.0052 mol) of which, on reaction with 1.25 ml (0.016 mol) of sulfuryl chloride in MDC afforded 0.94 g (66%) of 2-chloromethyl-4-propylsaccharin.

EXAMPLE 29

The 0.07 g sample of material obtained in the early fractions from the chromatographic separation described above in Example 28A was reacted with 0.05 ml of sulfuryl chloride in MDC and the product recrystallized from cyclohexane-ethyl acetate to give 20 mg (51%) of 2-chloromethyl-4,7-dimethylsaccharin, mp 107°–108° C.

EXAMPLE 30A–30BK

Following a procedure similar to that described in Example 4 above, substituting for the 2-chloromethyl-4-chlorosaccharin and the sodium 1-phenyltetrazole salt used therein, molar equivalent amounts of a respective appropriate 2-halomethyl-4-$R_3$-$R_4$-substituted saccharin and an appropriate $L_nR_1$ moiety, the following compounds of formula I in TABLE B below were prepared. The identities of the halogen moiety in the 2-halomethylsaccharin and the base used to catalyze the reaction, i.e., either the sodium or thallium salt of the $L_nR_1$ reactant or the added basic catalyst, i.e., potassium carbonate, triethylamine (TEA), ethyldiisopropylamine (EDIPA) or sodium methoxide, are given in the column headed "X/Base". The reaction solvent used (DMF, THF, MDC, MEK or acetone) is given in the column headed "Sol.", and the melting point (mp) and the solvent used for recrystallization are given in the column headed "mp/From". In TABLE B, and in the other tables which follow, various heterocyclic or other groups, $R_1$, are abbreviated as follows:

| | |
|---|---|
| tet. | tetrazolyl |
| triaz. | triazolyl |
| Mor. | morpholinyl |
| thiadiaz. | thiadiazolyl |
| imidaz. | imidazolyl |
| benzthiaz. | benzothiazolyl |
| benzoxaz. | benzoxazolyl |

TABLE B

| Ex. | R₁/R₂ | R₃/R₄ | n/L | X/Base | Solv. | mp/From | Yield |
|---|---|---|---|---|---|---|---|
| 30A | 1-C₆H₅-5-tet. | H | 1 | Cl | DMF | 168–170 | 67 |
|  | H | 5-(CH₃)₃CCH₂C(CH₃)₂ | S | Na Salt |  | EtOH |  |
| 30B | 4-Mor.SO₂C₆H₄ | H | 1 | Br | THF | Foams-no mp |  |
|  | H | H | O | TEA |  |  |  |
| 30C | 1-(3-NH₂C₆H₄)-5-tet. | H | 1 | Br | DMF | 187–189 | 66 |
|  | H | H | S | TEA |  | EtOH—CH₃CN |  |
| 30D | 1-(4-HOOCC₆H₄)-5-tet. | H | 1 | Cl | MDC | 201–202 | 14 |
|  | H | H | S | TEA |  | i-PrOH—CH₃CN |  |
| 30E | 1-[3,5-(MeOCC)₂—C₆H₃]-5-tet. | H | 1 | Cl | MEK/DMF | 126–129 | 42 |
|  | H | H | S | K₂CO₃ |  | EtOH—CH₃CN |  |
| 30F | 2-pyrimidinyl | H | 1 | Br | MEK | 170–172 | 40 |
|  | H | H | S | K₂CO₃ |  | EtOH—CH₃CN |  |
| 30G | 6-(1-oxophen-alenyl) | H | 1 | Br | DMF | 233–234 | 15 |
|  | H | H | O | TlOEt |  |  |  |
| 30H | 1-C₆H₅-5-tet. | CH₃ | 1 | Cl | Acet. | 162–164 | 89 |
|  | H | H | S | Na Salt |  | MDC |  |
| 30I | 1-C₆H₅-2-(1,3,4-triaz.) | H | 1 | Br | DMF |  |  |
|  | H | H | S | TlOEt |  |  |  |
| 30J | 1-(4-Mor.CH₂—CH₂)-5-tet. | C₂H₅ | 1 | Cl | MDC | oil |  |
|  | H | H | S | TEA |  |  |  |
| 30K | 1-(4-Mor.CH₂—CH₂)-5-tet. | H | 1 | Br | MDC | oil |  |
|  | H | H | S | TEA |  |  |  |
| 30L | 1-C₆H₅-5-tet. | C₂H₅O | 1 | Cl | MEK | 94–96 | 74 |
|  | H | 7-CH₃(OCH₂CH₂)₂O | S | Na Salt |  |  |  |
| 30M | 1-C₆H₅-5-tet. | CH₃O | 1 | Cl | MEK | 104–106 |  |
|  | H | 7-CH₃(OCH₂CH₂)₂O | S | Na Salt |  |  |  |
| 30N | 3-pyrido-[2,1-c]-s-triaz. | H | 1 | Br | DMF | 198–200 | 66 |
|  | H | H | S | TEA |  | EtOH—CH₃CN |  |
| 30-O | 4-(3-HOOCC₆H₄)-5-thioxo-1-tet. | H | 0 | Br | MDC | Dec. 110 |  |
|  | H | H | — | TEA |  | i-PrOH |  |
| 30P | 5-(CyclohexNH)-2-(1,3,4-thiadiaz.) | H | 1 | Br | DMF | 188.5–190.5 | 61 |
|  | H | H | S | TEA |  | EtOH |  |
| 30Q | 1-(3-pyridyl)-5-tet. | H | 1 | Br | DMF | 149.0–150.0 | 53 |
|  | H | H | S | TEA |  | EtOH—CH₃CN |  |
| 30R | 4-(3-pyridyl)-5-thioxo-1-tet. | H | 0 | Br | DMF | 108.0–110.0 | 8 |
|  | H | H | — | NaH |  | EtOAc |  |
| 30S | 4-(3-CH₃CONH—C₆H₄)-5-triaz. | CH₃ | 1 | Cl | DMF | 225–227 | 42 |
|  | H | H | S | K₂CO₃ |  | CH₃CN |  |
| 30T | 1-C₆H₅-5-tet. | CH₃O | 1 | Cl | DMF/MEK | 192–193 |  |
|  | H | 7-CH₃O | S | Na Salt |  |  |  |
| 30U | 1-C₆H₅-5-tet. | CH₃O | 1 | Cl | DMF | 164–165 | 73 |
|  | H | H | S | Na Salt |  | EtOH—CH₃CN |  |
| 30V | 1-C₆H₅-5-tet. | Br | 1 | Cl | DMF | 185.5–188.0 | 69 |
|  | H | H | S | Na Salt |  | EtOH—CH₃CN |  |
| 30W | 2-Me-5-thioxo-1-tet. | H | 0 | Br | CH₃OH | 133.5–135.0 | 15 |
|  | H | H | — | NaOMe |  |  |  |
| 30X | 2-Me-5-tet. | H | 1 | Br | CH₃OH | 182.0–183.0 | 17 |
|  | H | H | S | NaOMe |  | EtOAc-hex |  |
| 30Y | 1-(3-pyridyl)-5-tet. | H | 1 | Cl | DMF | 138.5–140.5 | 39 |
|  | H | H | S | TEA |  | EtOH |  |
| 30Z | 4-(3-pyridyl)-5-thioxo-1-tet. | (CH₃)₂CH | 0 | Cl | DMF | 157.0–159 | 11 |
|  | H | H | — | TEA |  | EtOH |  |
| 30AA | 1-C₆H₅-5-tet. | (C₂H₅)₂CH | 1 | Cl | DMF | 88.0–90.0 | 52 |
|  | H | H | S | Na Salt |  | Et₂O-hex |  |
| 30AB | 5-Me-2-(1,3,4-thiadiaz. | H | 1 | Br | DMF | 114–116 | 75 |
|  | H | H | S | TEA |  | i-PrOH |  |
| 30AC | 1-Me-2-(1,3,4-triaz.) | H | 1 | Br | DMF | 187–189 | 28 |
|  | H | H | S | TEA |  | EtOH |  |
| 30AD | 2-MeS-5-thioxo-4-(1,3,4-thiadiaz.) | H | 0 | Br | DMF | 132–134 | 68 |
|  | H | H | — | TEA |  | EtOAc-hex |  |
| 30AE | 1-C₆H₅5-tet. | C₂H₅ | 1 | Cl | DMF | 180.0–182.0 | 43 |
|  | H | H | S | Na Salt |  | EtOac—CHCl₃ |  |
| 30AF | 4-C₆H₅-2-(1,3,5-thiadiaz.) | H | 1 | Br | DMF | 117.0–119.0 | 33 |
|  | H | H | S | TEA |  | i-PrOH |  |

TABLE B-continued

| Ex. | R₁/R₂ | R₃/R₄ | n/L | X/Base | Solv. | mp/From | Yield |
|---|---|---|---|---|---|---|---|
| 30AG | 1-C$_6$H$_5$-5-tet. | H | 1 | Cl | DMF | 166.0–168.0 | 30 |
|  | H | 7-Cl | S | Na Salt |  | CH$_3$CN |  |
| 30AH | 5-HS-2-(1,3,4-thiadiaz.) | H | 1 | Br | EtOH | 201.0–203.0 | 32 |
|  | H | H | S | NaOMe |  | EtOH |  |
| 30AI | 1-C$_6$H$_5$-5-tet. | CH$_3$O | 1 | Cl | DMF | 158.0–160.0 |  |
|  | H | 5-CH$_3$O | S | Na Salt |  | EtOH |  |
| 30AJ | 4-C$_6$H$_5$-5-thioxo-1-tet. | (CH$_3$)$_2$CH | 0 | Cl | DMF | 178.0–179.5 | 16 |
|  | H | H | — | Na Salt |  | EtOH |  |
| 30AK | 1-C$_6$H$_5$-5-tet. | (CH$_3$)$_2$CH | 1 | Cl | DMF | 140.0–141.0 |  |
|  | H | H | S | Na Salt |  | EtOH |  |
| 30AL | 1-C$_6$H$_5$-5-tet. | n-C$_3$H$_7$ | 1 | Cl | DMF | 109.0–111.0 | 24 |
|  | H | H | S | Na Salt |  | EtOH—CH$_3$CN |  |
| 30AM | 5-CH$_3$-2-(1,3,-4-thiadiaz.) | (CH$_3$)$_2$CH | 1 | Cl | DMF | 72–74 | 74 |
|  | H | H | S | TEA |  |  |  |
| 30AN | 1-CH$_3$-5-tet. | (CH$_3$)$_2$CH | 1 | Cl | DMF | 137.0–139.0 | 51 |
|  | H | H | S | TEA |  | EtOH—H$_2$O |  |
| 30AO | 1-C$_6$H$_5$-5-tet. | CH$_3$CHC$_2$H$_5$ | 1 | Cl | DMF | 120.0–122.0 | 52 |
|  | H | H | S | Na Salt |  | EtOAc-hex |  |
| 30AP | 1-EtO$_2$CCH$_2$-5-tet. | H | 1 | Br | DMF | 142.0–143.0 | 29 |
|  | H | H | S | TEA |  | MDC-hex |  |
| 30AQ | 1-(HOCH$_2$CH$_2$)-5-tet. | H | 1 | Br | MDC | 148.0–150.0 | 88 |
|  | H | H | S | EDIPA |  |  |  |
| 30AR | 1-C$_6$H$_5$-4-COO—CH$_3$-2-imidaz. | H | 1 | Br | MDC | 138.0–139.5 | 76 |
|  | H | H | S | EDIPA |  |  |  |
| 30AS | 1-Me$_2$NCOCH$_2$-5-tet. | H | 1 | Br | MDC | 178.5–179.5 | 70 |
|  | H | H | S | EDIPA |  |  |  |
| 30AT | 1-C$_6$H$_5$-5-tet. | C$_2$H$_5$O | 1 | Cl | DMF | 139.5–140.5 | 62 |
|  | H | H | S | Na Salt |  |  |  |
| 30AU | 1-C$_6$H$_5$-5-tet. | (CH$_3$)$_2$CHO | 1 | Cl | DMF | 124.5–125.5 | 94 |
|  | H | H | S | Na Salt |  |  |  |
| 30AV | 1-Me$_2$NCOCH$_2$-5-tet. | C$_2$H$_5$ | 1 | Cl | MDC | 146.5–148 | 80 |
|  | H | H | S | EDIPA |  |  |  |
| 30AW | 1-Me$_2$NCOCH$_2$-5-tet. | (CH$_3$)$_2$CH | 1 | Cl | MDC | 180.0–181.5 | 73 |
|  | H | H | S | EDIPA |  |  |  |
| 30AX | 1-Me$_2$NCOCH$_2$-5-tet. | C$_2$H$_5$O | 1 | Cl | MDC | 146.0–147.0 | 72 |
|  | H | H | S | TEA |  |  |  |
| 30AY | 1-C$_6$H$_5$-5-tet. | CH$_3$O | 1 | Cl | DMF |  |  |
|  | H | 6-CH$_3$O | S | Na Salt |  |  |  |
| 30AZ | 5-NH$_2$-2-(1,3,-4-thiadiaz.) | H | 1 | Br | EtOH | 164.0–165.0 | 46 |
|  | H | H | S | NaOMe |  | CH$_3$CN |  |
| 30BA | 1-oxo-6-phen-alenyl | (CH$_3$)$_2$CH | 1 | Cl | DMF | 224.0–226.0 | 51 |
|  | H | H | O | Tl Salt |  | EtOAc |  |
| 30BB | 2,6-Cl$_2$C$_6$H$_4$ | H | 1 | Br | DMF | 175.0–177.0 | 70 |
|  | H | H | O | Tl Sal |  |  |  |
| 30BC | 1-C$_6$H$_5$-5-tet. | C$_6$H$_5$ | 1 | Cl DMF | 170.0–172.0 | 87 |  |
|  | H | H | S | Na Salt |  |  |  |
| 30BD | 6-NO$_2$-2-benzthiaz. | H | 1 | Br | MEK | 185–186 |  |
|  | H | H | S | K$_2$CO$_3$ |  | CH$_3$CN |  |
| 30BE | 6-NO$_2$-2-benzoxaz. | H | 1 | Br | DMF | 161–163 | 28 |
|  | H | H | S | Tl Salt |  | CH$_3$CN |  |
| 30BF | 2-phthalimidyl | H | 0 | Br | DMF |  | 33 |
|  | H | H | — | K Salt |  | EtOH—CH$_3$CN |  |
| 30BG | 1-(4-Mor.CH$_2$—CH$_2$)-5-tet. | H | 1 | Br | MDC | 110–113 | 74 |
|  | H | H | S | TEA |  | EtOH |  |
| 30BH | 4-C$_6$H$_5$-5-oxo-1-tet. | H | 0 | Br | MEK | 153–155 | 74 |
|  | H | H | — | K$_2$CO$_3$ |  | EtOH |  |
| 30BI | 1-(4-Mor.CH$_2$—CH$_2$)-5-tet. | (CH$_2$)$_2$CH | 1 | Cl | MDC |  | 85 |
|  | H | H | S | TEA |  |  |  |
| 30BJ | 2-pyrimidinyl | H | 1 | Br | MEK | 170–172 | 40 |
|  | H | H | S | K$_2$CO$_3$ |  | EtOH—CH$_3$CN |  |
| 30BK | 1-C$_6$H$_5$-5-tet. | C$_2$H$_5$ | 1 | Cl | DMF | 162–164 | 74 |
|  | H | 5,6-(CH$_3$O)$_2$ | S | Na Salt |  | EtOH—H$_2$O |  |

EXAMPLE 31A–31C

Following a procedure similar to that described above in Example 17, substituting for the saccharin and the methyl 2-chloro-2-phenylthioacetate used therein molar equivalent amounts of a respective appropriate 4-R$_3$—R$_4$-substituted saccharin and an appropriate Cl—CHR$_2$—S—R$_1$ moiety, the following compounds of formula 1, shown in TABLE C, were similarly prepared where in each instance, n is 1 and L is —S—. In each case, the thallium salt of the saccharin derivative was used, and the reactions were carried out in DMF.

TABLE C

| Ex. | R₁/R₂ | R₃/R₄ | mp/From | Yield |
|---|---|---|---|---|
| 31A | C$_6$H$_5$ | H | 144–146 | 51 |
|  | COOMe | H | EtOH |  |

TABLE C-continued

| Ex. | R₁/R₂ | R₃/R₄ | mp/From | Yield |
|---|---|---|---|---|
| 31B | 1-C₆H₅-5-tet. C₆H₅S | H H | 130–132 EtOH | 44 |
| 31C | 1-C₆H₅-5-tet. H | H 6-NO₂ | 177–179 EtOH/CH₃CN | 43 |

EXAMPLE 32A

A solution of 0.28 g (0.00067 mol) of 2-(2,6-dichlorophenylthiomethyl)saccharin in 5 ml of MDC was treated with about 0.3 g (0.0017 mol) of 3-chloroperbenzoic acid with stirring, and the mixture was stirred for about 16 hours and quenched with aqueous 10% sodium bisulfite solution. The reaction mixture was diluted with MDC, the layers separated and the organic layer washed sequentially with water, saturated sodium bicarbonate, and saturated ammonium chloride, dried over sodium sulfate and evaporated to dryness in vacuo and the residue chromatographed on silica gel with 10:1 MDC:diethyl ether. There was thus obtained 0.1 g (10%) of 2-(2,6-dichlorophenylsulfonylmethyl)saccharin, mp 201.0°–203.0° C.

EXAMPLE 32B

Following a procedure similar to that described in Example 32A, 0.75 g (0.0023 mol) of 2-(2-pyrimidinylsulfinylmethyl)saccharin was oxidized with 0.4 g (0.0023 mol) of 3-chloroperbenzoic acid in 50 ml of MDC and the product recrystallized from 75:25 acetonitrile:ethanol to give 2-(2-pyrimidinylsulfonylmethyl)saccharin, mp 225°–227° C.

EXAMPLE 33A

To a solution of 0.345 g (0.001 mol) of 2-(5-mercapto-1,3,4-thiadiazol-2-ylthiomethyl)saccharin and 0.46 ml (0.003 mol) of triethylamine in 2 ml of DMF was added 0.37 g (0.002 mol) of 4-(2-chloroethyl)morpholine hydrochloride. The reaction mixture was stirred at ambient temperature for about 24 hours, quenched by pouring into water and extracted with ethyl acetate. The organic layer was washed with water, then with brine and taken to dryness to give a yellow oil which was taken into chloroform and chromatographed on silica gel, eluting with ethyl acetate. There was thus obtained 0.225 g (49%) of 2-(5-[2-(4-morpholinyl)ethylthio]-1,3,4-thiadiazol-2-ylthiomethyl)saccharin, mp 129°–131° C.

EXAMPLE 33B

Following a procedure similar to that described in Example 33A above, 1.72 g (0.005 mol) of 2-(5-mercapto-1,3,4-thiadiazol-2-ylthiomethyl)saccharin was reacted with 1.44 g (0.01 mol) of 2-dimethylaminoethyl chloride hydrochloride in 10 ml of DMF in the presence of 1.72 g (0.017 mol) of triethylamine to give 1.2 g (58%) of 2-(5-[2-(N,N-dimethylamino)ethylthio]-1,3,4-thiadiazol-2-ylthiomethyl)saccharin, mp 90.5°–91.5° C. (from ethyl acetate).

EXAMPLE 33C

Following a procedure similar to that described above in Example 33A, 0.69 g (0.002 mol) of 2-(5-mercapto-1,3,4-thiadiazol-2-ylthiomethyl)saccharin was reacted with 0.74 g (0.004 mol) of 1-(2-chloroethyl)piperidine hydrochloride in 4 ml of DMF in the presence of 0.4 g of triethylamine to give 0.55 g (60%) of 2-(5-[2-(1-piperidinyl)ethylthio]-1,3,4-thiadiazol-2-ylthiomethyl)saccharin, mp 100.0°–101.0° C. (from ethyl acetate).

EXAMPLE 33D

Following a procedure similar to that described in Example 33A, 2-(5-mercapto-1,3,4-thiadiazol-2-ylthiomethyl)saccharin is reacted with 2-chloroethyldiethylamine hydrochloride in DMF in the presence of triethylamine to give 2-(5-[2-(diethylamino)ethylthio]-1,3,4-thiadiazol-2-ylthiomethyl)saccharin, mp 93.0°–94.5° C. (from cyclohexane:ethyl acetate).

EXAMPLE 33E

Following a procedure similar to that described in Example 33A, 1.72 g (0.005 mol) of 2-(5-mercapto-1,3,4-thiadiazol-2-ylthiomethyl)saccharin was reacted with 1.84 g (0.01 mol) of 1-(2-chloroethyl)piperidine hydrochloride in 10 ml of DMF in the presence of 2.4 ml of triethylamine to give 1.08 g (47%) of 2-(5-[2-(1-piperidinyl)ethylthio]-2-thioxo-1,3,4-thiadiazolin-3-ylmethyl)saccharin, mp 89.0°–92.0° C., in which the 1,3,4-thiadiazol-2-ylthiomethyl group underwent rearrangement during the reaction.

EXAMPLE 34

To a solution of 0.44 g (0.0013 mol) of 2-[1-(2-hydroxyethyl)-1H-tetrazol-5-ylthiomethyl]saccharin in 10 ml of acetone was added chromic acid prepared from dilute sulfuric acid and sodium dichromate dihydrate (Jones' reagent) while maintaining the reaction mixture at 0° C. until a persistent orange-brown color remained in the solution. The mixture was stirred for 1 hour at 0° C., then at ambient temperature for about 6 hours, diluted with water and extracted with ethyl acetate. The combined organic extracts were washed with water, then with brine, dried and evaporated to dryness, and the residue chromatographed on silica gel, eluting with 5–15% methanol-MDC, to give 0.29 g (63%) of 2-[1-(2-carboxymethyl)-1H-tetrazol-5-ylthiomethyl]saccharin, mp 173°–175° C.

EXAMPLE 35

A solution of 1 g (0.0026 mol) of 2-[1-(3-aminophenyl)-1H-tetrazol-5-ylthiomethyl]saccharin and 0.26 g (0.0026 mol) of succinic anhydride in 50 ml of dioxane was stirred at ambient temperature for two hours, heated under reflux for six hours, stirred at ambient temperature for two days, then heated to reflux again and additional small amounts of succinic anhydride added over a period of a few hours until TLC analysis indicated the absence of starting material in the reaction mixture. The reaction was cooled, poured into dilute hydrochloric acid and ice water, and the solid which separated was collected, dried and recrystallized from 50:50 ethanol:acetonitrile to give 0.5 g (39%) of 2-[1-(3-succinoylaminophenyl)-1H-tetrazol-5-ylthiomethyl]saccharin, mp 197°–199° C.

EXAMPLE 36

5-Nitro-2-(1-phenyl-1H-tetrazol-5-ylthiomethyl)saccharin (1 g, 0.0024 mol) was reduced over 3 spatulas of Rainey nickel (washed with THF prior to use) in 150 ml of THF under 50 psi hydrogen pressure. When reduction was complete (in about 5 hours) the reaction mixture was filtered, the filter pad washed with THF, and the filtrate evaporated to dryness to give a pale yellow, cloudy oil which was taken into hot ethanol and filtered. On cooling, the product separated and was collected to give 0.4 g (43%) of 5-amino-2-(1-phenyl-1H-tetrazol-5-ylthiomethyl)saccharin as yellow crystals.

EXAMPLE 37

A suspension of 0.4 g of 5-amino-2-(1-phenyl-1H-tetrazol-5-ylthiomethyl)saccharin in 25 ml of acetonitrile was treated with 0.08 g (0.001 mol) of acetyl chloride, the mixture was heated under reflux for 30 minutes, treated with an additional drop of acetyl chloride and refluxing continued for another 30 minutes. Evaporation of the mixture to dryness afforded a white foam which was chromatographed on silica gel with 95:5 MDC:ethyl acetate to give 200 mg (43%) of 5-acetylamino-2-(1-phenyl-1H-tetrazol-5-ylthiomethyl)saccharin.

EXAMPLE 38

A solution of 5 g (0.025 mol) of the sodium salt of 1-phenyl-5-mercaptotetrazole in 50 ml of methyl ethyl ketone was added dropwise with stirring to a warm solution of 3-chloro-1-iodopropane in 300 ml of MEK. The mixture was stirred at 40° C. for six hours, allowed to stand at ambient temperature for about two days and the reaction mixture taken to dryness in vacuo. The residue was dissolved in MDC, the solution washed with water and the aqueous washings back-extracted with MDC. The combined organic extracts were dried and taken to dryness to give a yellow oil which was chromatographed on silica gel, eluting with MDC. There was thus obtained 3.6 g (57%) of 1-phenyl-5-(3-chloropropylthio)-1H-tetrazole as a pale yellow oil. (In another run, the same material was obtained as a white crystalline solid, mp 33°–34° C.)

The product (3.5 g, 0.014 mol) was dissolved in 100 ml of MEK, 1.7 g (0.014 mol) of the sodium salt of thiophenol was added, the mixture warmed at 40° C. for three hours, poured into potassium bicarbonate solution and the mixture extracted with MDC. The combined organic extracts, on drying and evaporation to dryness, afforded a pale yellow oil which was chromatographed on silica gel with MDC to give 3.85 g (86%) of 1-phenyl-5-[3-(phenylthio)propylthio]-1H-tetrazole. (In another run this same material was obtained as white crystals, mp 57°–59° C.)

A solution of 3.8 g (0.012 mol) of the product in 100 ml of carbon tetrachloride was treated with 1.5 g (0.012 mol) of N-chlorosuccinimide, the mixture allowed to stand at ambient temperature for one hour, then filtered and the filtrate evaporated to dryness to give 4.3 g of 1-phenyl-5-[3-chloro-3-(phenylthio)propylthio]-1H-tetrazole.

The product (0.012 mol) and 4.58 g (0.12 mol) of the thallium salt of saccharin dissolved in 75 ml of DMF was heated at 50° C. for three hours, allowed to stand at ambient temperature for two hours, filtered and the filter pad washed with DMF. The combined filtrate was poured into water, the mixture extracted with MDC, and the combined organic extracts were washed with brine and concentrated to dryness to give a pale yellow oil which was chromatographed on silica gel with MDC to give 2.45 g (41%) of 2-[1-phenylthio-3-(1-phenyl-1H-tetrazol-5-ylthio)propyl] saccharin.

The product (1 g, 0.002 mol) was dissolved in MDC and oxidized with 0.34 g (0.002 mol) of 3-chloroperbenzoic acid according to the procedure described in Example 32A above. There was thus obtained 0.8 g (76%) of 2-[1-phenylsulfinyl-3-(1-phenyl-1H-tetrazol-5-ylthio)propyl] saccharin.

The product (1.6 g, 0.003 mol) was heated in 130 ml of diethylene glycol dimethyl ether at 120° C. for 45 minutes and the mixture cooled and poured into water. The solid which separated was collected, dried and dissolved in MDC and the solution chromatographed on silica gel in MDC. There was thus obtained 1.2 g of trans-2-[3-(1-phenyl-1H-tetrazol-5-ylthio)-1-propenyl]saccharin, mp 191°–193° C.

EXAMPLE 39

Other 2-unsubstituted saccharins of formula II useful as intermediates for the preparation of the compounds of formula I can be prepared as follows.

Reaction of 3-trifluoromethylbenzoic acid with thionyl chloride affords 3-trifluoromethylbenzoyl chloride, which, on reaction with diethylamine, affords 3-trifluoromethyl-N, N-diethylbenzamide. Following a procedure similar to that described in Example 22A, reaction of the latter with s-butyl lithium and reaction of the resulting lithium salt with sulfur dioxide followed by sodium hydroxylaminesulfonate affords 3-trifluoromethyl-2-aminosulfonyl-N,N-diethylbenzamide, which, on heating in glacial acetic acid, affords 7-trifluoromethyl saccharin.

Similarly, reaction of 4-cyclohexylbenzoic acid with thionyl chloride affords 4-cyclohexylbenzoyl chloride, which, on reaction with diethylamine, affords 4-cyclohexyl-N,N-diethylbenzamide. Following a procedure similar to that described in Example 22A, reaction of the latter with s-butyl lithium and reaction of the resulting lithium salt with sulfur dioxide followed by sodium hydroxylaminesulfonate affords 4-cyclohexyl-2-aminosulfonyl-N,N-diethylbenzamide, which, on heating in glacial acetic acid, affords 6-cyclohexylsaccharin.

Reaction of 6-aminosaccharin with methanesulfonyl chloride or trifluoromethylsulfonyl chloride in MDC in the presence of pyridine affords, respectively, 6-methylsulfonylaminosaccharin or 6-trifluoromethylsulfonylaminosaccharin.

Diazotization of 6-aminosaccharin with nitrous acid in an acid medium and decomposition of the resulting diazonium salt in the presence of cupric cyanide or cupric chloride and sulfur dioxide, or cupric chloride and an alkali metal salt of methyl mercaptan or trifluoromethyl mercaptan affords, respectively, 6-cyanosaccharin, 6-chlorosulfonylsaccharin, 6-methylthiosaccharin or 6-trifluoromethylthiosaccharin. Reaction of the 6-chlorosulfonylsaccharin in situ with ammonia or methanesulfonylamide affords, respectively, 6-aminosulfonylsaccharin and 6-methanesulfonylaminosulfonylsaccharin. Oxidation of 6-methylthiosaccharin and 6-trifluoromethylthiosaccharin with two molar equivalents of 3-chloroperbenzoic acid affords 6-methylsulfonylsaccharin and 6-trifluoromethylsulfonylsaccharin, respectively.

Hydrolysis of 6-cyanosaccharin by heating with aqueous sodium hydroxide affords saccharin-6-carboxylic acid. Reaction of 6-cyanosaccharin by heating with a catalytic amount of sulfuric acid in ethanol solution affords ethyl saccharin-6-carboxylate, which, on reduction with lithium borohydride, affords 6-hydroxymethylsaccharin. Oxidation of the latter with pyridine:chromium trioxide (2:1) complex (Collins reagent) in MDC affords 6-formylsaccharin, which, on reductive amination with ammonia and sodium cyanoborohydride, affords 6-aminomethylsaccharin.

Reaction of each of the 2-unsubstituted saccharins so-prepared with chloromethyl phenyl sulfide in the presence of potassium t-butoxide and tetrabutylammonium bromide, and reaction of the resulting 2-phenylthiomethylsaccharins with sulfuryl chloride in MDC affords the $R_4$-2-unsubstituted saccharins of formula I listed in TABLE D where, in each instance, m and n are 0, $R_1$ is Cl and $R_2$ and $R_3$ are both hydrogen.

TABLE D

| Example | $R_4$ |
|---|---|
| 39A | 7-$CF_3$ |
| 39B | 6-cyclohexyl |
| 39C | 6-$CH_3SO_2NH$ |
| 39D | 6-$CF_3SO_2NH$ |
| 39E | 6-CN |
| 39F | 6-$NH_2SO_2$ |
| 39G | 6-$CH_3SO_2NHSO_2$ |
| 39H | 6-$CH_3SO_2$ |
| 39I | 6-$CF_3SO_2$ |
| 39J | 6-HOOC |
| 39K | 6-$HOCH_2$ |
| 39L | 6-OHC |
| 39M | 6-$NH_2CH_2$ |

EXAMPLE 40

Following a procedure similar to that described in Example 4 above, substituting for the 2-chloromethyl-4-chlorosaccharin and the sodium 1-phenyltetrazole salt used therein molar equivalent amounts of a respective appropriate 2-chloromethyl-$R_4$-saccharin described in TABLE D above and an appropriate $L_nR_1$ moiety, the following compounds listed in TABLE E, where $R_3$ in each instance, unless noted otherwise, is hydrogen, are prepared.

TABLE E

| Example | n | L | $R_1$ | $R_4$ |
|---|---|---|---|---|
| 40A | 1 | S | 1-$C_6H_5$-5-tet. | 7-$CF_3$ |
| 40B | 1 | S | 1-$C_6H_5$-2-(1,3,4-triaz.) | 6-cyclohexyl |
| 40C | 1 | S | 1-(4-Mor.$CH_2CH_2$)-5-tet. | 6-$CH_3SO_2NH$ |
| 40D | 1 | S | 3-(pyridyl)-5-tet. | 6-$CF_3SO_2NH$ |
| 40E | 0 | — | 4-(3-pyridyl)-5-thioxo-1-tet. | 6-CN |
| 40F | 0 | — | 2-Me-5-thioxo-1-tet. | 6-$NH_2SO_2$ |
| 40G | 1 | S | 2-Me-5-tet. | 6-$CH_3SO_2NHSO_2$ |
| 40H | 1 | S | 5-Me-2-(1,3,4-thiadiaz.) | 6-$CH_3SO_2$ |
| 40I | 1 | S | 1-Me-2-(1,3,4-triaz.) | 6-$CF_3SO_2$ |
| 40J | 1 | S | 4-$C_6H_5$-2-(1,3,5-thiadiaz.) | 6-HOOC |
| 40K | 1 | S | 5-HS-2-(1,3,4-thiadiaz.) | 6-$HOCH_2$ |
| 40L | 0 | 1 | 4-$C_6H_5$-5-thioxo-1-tet. | 6-OHC |
| 40M | 1 | S | 5-$CH_3$-2-(1,3,4-thiadiaz.) | 6-$NH_2CH_2$ |
| 40N | 1 | S | 1-$C_6H_5$-5-tet | 5-$CH_3O$ (a) |

(a) $R_3$ is isopropyl. Prepared by reaction of N,N-diethyl-carbamyl chloride with the lithium salt of 2-bromo-5-methoxy-isopropylbenzene; reaction of the resulting (79%) N,N-diethyl-2-isopropyl-4-methoxybenzamide with s-butyl lithium followed by sulfur dioxide and sodium hydroxylamine sulfonate; heating the resulting (56%) N,N-diethyl-2-aminosulfonyl-4-methoxy-6-isopropylbenzamide in glacial acetic acid; reaction of the resulting (100%) diethylammonium salt of 4-isopropyl-6- methoxysaccharin with chloromethyl phenyl sulfide; reaction of the resulting (88%) 2-phenylthiomethyl-4-isopropyl-6-methoxy saccharin with sulfuryl chloride, and reaction of the resulting (88%) 2-chloromethyl-4-isopropyl-6-methoxysaccharin with the sodium salt of 1-phenyl-5-mercaptotetrazole.

BIOLOGICAL TEST RESULTS

Measurement of the inhibition constant, $K_i$, of a HLE-inhibitor complex has been described for "truly reversible inhibition constants" usually concerning competitive inhibitors. [Cha, Biochem. Pharmacol., 24, 2177–2185 (1975)]. The compounds of the present invention, however, do not form truly reversible inhibitor complexes but are consumed by the enzyme to some extent. Thus, instead of measuring a $K_i$, a $K_i^*$ is calculated which is defined as the ratio of the $k_{off}/k_{on}$, the rate of reactivation of the enzyme to the rate of inactivation of the enzyme. The values of $k_{off}$ and $k_{on}$ are measured and $K_i^*$ is then calculated.

The rate of inactivation, $k_{on}$, of enzymatic activity was determined for the compounds tested by measuring the enzyme activity of an aliquot of the respective enzyme as a function of time after addition of the test compound. By plotting the log of the enzyme activity against time, an observed rate of inactivation, $k_{obs}$, is obtained which can be represented as $k_{obs}=\ln 2/t_{1/2}$ where $t_{1/2}$ is the time required for the enzyme activity to drop by 50%. The rate of inactivation is then equal to $$k_{on} = \frac{k_{obs}}{[I]}$$

where [I] is the concentration of the inhibiting compound.

The reactivation constant, $k_{off}$, is similarly determined and the inhibition constant, $K_i^*$, is then calculated as $$K_i^* = k_{off}/k_{on}$$

The values obtained for $k_{on}$ and $K_i^*$ for specific substituted saccharin derivatives are shown in TABLE F, the compounds being identified by the Example numbers above where their preparations are described.

TABLE F

| | Elastase | | α-Chymotrypsin | |
|---|---|---|---|---|
| Example | $10^{-3} \times k_{on}$ ($M^{-1}$ $sec^{-1}$) | $K_i^*$ (nM) | $10^{-3} \times k_{on}$ ($M^{-1}$ $sec^{-1}$) | $K_i^*$ (nM) |
| 1 | 0.63 | 102 | 1.2 | 917 |
| 2 | 4.9 | 45 | 2.9 | 51 |
| 3 | 450 | 0.5 | 5.8 | 26 |
| 4 | 20 | 12 | | |
| 5 | 44 | 6 | 6.0 | 25 |
| 6 | 5.5 | 15 | 3.7 | 300 |
| 7 | 5.2 | 15 | | |
| 8 | 1.0 | 81 | 2.1 | 523 |
| 9 | 2.5 | 32 | | |
| 10 | 7.0 | 11 | 7.0 | 157 |
| 11 | 4.6 | | | |
| 12 | 0.97 | 82 | 1.1 | 1000 |
| 13 | 0.3 | 285 | 2.6 | 423 |
| 14 | 0.6 | 138 | 2.8 | 392 |
| 15 | 3.2 | 69 | | |
| 16 | | 2,600 | | |
| 17 | 2.9 | 270 | | |
| 18 | 1.0 | 100 | 0.21 | 620 |
| 19 | | 8,500 | | |
| 21 | 950 | 0.5 | | |
| 22A | 12.4 | 6.0 | | |
| 22B | 2.4 | 90 | | |
| 22C | 105 | 0.4 | | |
| 22D | 75.8 | 1.3 | | |
| 22E | 4.7 | 91 | | |
| 22F | 20 | 6.5 | | |
| 22G | 3.0 | 50 | | |
| 22H | 25 | 1.2 | | |
| 23A | 30 | 9 | | |
| 23B | 50 | 4.4 | | |
| 27 | 7.5 | 13 | | |
| 28 | 50.7 | 2.5 | | |
| 29 | 1.1 | 120 | | |
| 30A | | 10,500 | | |
| 30C | 2.5 | 17 | | |
| 30D | 0.8 | 85 | | |
| 30E | 7.3 | 12.7 | | |
| 30F | | >>85,000 | | |
| 30G | 9.3 | 7.7 | | |
| 30H | 3.2 | | | |
| 30I | 0.45 | 650 | | |

TABLE F-continued

| | Elastase | | α-Chymotrypsin | |
|---|---|---|---|---|
| Example | $10^{-3} \times k_{on}$ ($M^{-1} sec^{-1}$) | $K_i^*$ (nM) | $10^{-3} \times k_{on}$ ($M^{-1} sec^{-1}$) | $K_i^*$ (nM) |
| 30J | 14.0 | 10 | | |
| 30L | 6.5 | 7.6 | | |
| 30M | 1.0 | 10 | | |
| 30N | 0.25 | 220 | | |
| 30-O | 0.03 | 2,000 | | |
| 30Q | 1.38 | 70.4 | | |
| 30R | 2.3 | 36 | | |
| 30S | 1.81 | 40.4 | | |
| 30T | 1.1 | 14.5 | | |
| 30U | 5.6 | 13.6 | | |
| 30V | 24 | 15 | | |
| 30W | 1.5 | 80 | | |
| 30X | 0.55 | 143 | | |
| 30Z | 70 | 0.5 | | |
| 30AB | 2.8 | 23 | | |
| 30AC | 0.19 | 246 | | |
| 30AD | 7.0 | 11.6 | | |
| 30AE | 63.2 | 2.0 | | |
| 30AF | 4.2 | 12.5 | | |
| 30AG | | >1,000 | | |
| 30AH | 1.1 | 60 | | |
| 30AI | 53.8 | 2 | | |
| 30AJ | 1.8 | 15.5 | | |
| 30AK | 94 | 0.3 | | |
| 30AL | 100 | 0.7 | | |
| 30AM | 12.3 | 4.5 | | |
| 30AN | 19 | 30 | | |
| 30AP | 1.3 | 51 | | |
| 30AQ | 0.9 | 260 | | |
| 30AR | 0.3 | 153 | | |
| 30AS | 1.7 | 40 | | |
| 30AT | 45.3 | 3 | | |
| 30AU | 8.9 | 17.5 | | |
| 30AV | 7.6 | 15 | | |
| 30AW | 30 | 1 | | |
| 30AX | 7.5 | 16 | | |
| 30AY | 49 | 0.6 | | |
| 30BA | 42 | 0.8 | | |
| 30BB | | >500 | | |
| 30BC | 5.8 | 80 | | |
| 30BD | 11.7 | 8 | | |
| 30BE | 7.4 | 250 | | |
| 30BF | 0.02 | 40,000 | | |
| 30BG | 1.7 | 50 | | |
| 30BH | | >10,000 | | |
| 30BI | 39 | 0.5 | | |
| 31C | 3.4 | 300 | | |
| 32A | 0.6 | 145 | | |
| 33 | 3.6 | 12 | | |
| 33B | 4.0 | 18 | | |
| 33C | 0.2 | 350 | | |
| 34 | 0.4 | 256 | | |
| 35 | 3.6 | 22 | | |
| 37 | | >90,000 | | |
| 38 | 43 | 2 | | |

In the compound of formula I as described at pages 9–11 above $R_1$ is in addition to those moieties described at pages 9–10 above:

phenyl substituted by 1-(4-lower-alkylpiperazin-1-yl)carbonyl, 4-morpholinylsulfonyl, formyl, lower-alkoxycarbonyl, 4-thiamorpholinylsulfonyl or the S-dioxide thereof, hydroxy-lower-alkyl, halo-lower-alkyl, 4-morpholinyl-lower-alkylaminocarbonyl, 4-morpholinyl-lower-alkoxycarbonyl, 1-(4-lower-alkylpiperazin-1-yl)sulfonyl, 4-morpholinyl-lower-alkoxy, di-lower-alkylamino-lower-alkylaminosulfonyl or an N-lower-alkyl derivative thereof, halomethyl, lower-alkyl-sulfonyl, phenyl, 4,5-dihydrooxazol-2-yl, lower-alkyltetrazol-5-yl, 4-morpholinylcarbonyl, nitrophenylazo, carboxyl or di-lower-alkylphosphonyl, or heterocyclyl selected from pyridazin-3-yl, 4-pyron-3-yl, quinolin-8-yl, 1,3,4-oxadiazol-2-yl, coumarin-7-yl, saccharin-6-yl, imidazol-2-yl, 1,3,4-triazol-2-yl, thiazol-2-yl, 2-thioxo-2,3-dihydro-1,3,4-oxadiazol-3-yl, 1,2,5-thiadiazol-3-yl, 2-thioxo-2,3-dihydro-1,3,4-thiadiazol3-yl, 2-thioxo-2,3-dihydro-1,3,4-thiadiazol-5-yl, 1,2,3-triazol-2-yl, 1,2,4-triazin-5-yl, 5-oxo-6-hydroxy-4,5-dihydro-1,2,4-triazin-3-yl, isoxazol-5-yl, isoxazol-3-yl, 5-oxo-1,2,4-oxadiazol-4-yl, pyridyl, 1,1,3-trioxo-tetrahydro-1,2,5-thiadiazol-2-yl, 6,7-dihydro-1H-1,2,4-triazolo[3,4-b][1,3]thiazin-3-yl, 4,5-dihydro-5-oxo-1,2,4-oxadiazol-4-yl, 2,5-dioxopyrrolidin-1-yl, 3-indolyl, oxazol-2-yl, thiazol-4-yl, 2,3-dihydro-2-oxo-5-phenyl-1,3,4-thiadiazol-3-yl and 2,3-dihydro-2-oxo-5-phenyl-1,3,4-oxadiazol-3-yl, or heterocyclyl as defined at page 9 or 93 above substituted on any available nitrogen atom by phenyl substituted by carboxy-lower-alkanoylamino, or heterocyclyl as defined at page 9 or 93 above substituted on any available carbon atom by di-lower-alkylamino-lower-alkyl, 4-morpholinyl-lower-alkylamino, cyano, 1-piperidinyl-lower-alkyl, hydroxy-lower-alkyl, phenylsulfonyl, toluenesulfonyl, halo, tri-lower-alkylsilyl, carboxy or alkali metal salt thereof, furyl, trifluoromethyl, 2-benzothiazolyl, lower-alkylsulfonyl, aminocarbonyl, benzyl, 4-morpholinyl, pyridinyl, lower-alkoxy, pyrazinyl, lower-alkoxycarbonyl-lower-alkyl, di-lower-alkylaminosulfonyl, 4-morpholinylcarbonyl, lower alkanoyl, benzyloxy, hydroxy, phenyl substituted by trifluoromethyl, lower-alkoxy-poly-lower-alkoxy, methylenedioxy or lower alkoxycarbonyl or benzoyl or benzoyl substituted by lower-alkoxy or halo, or, when L is —O— and n is 1, cycloheptatrienon-2-yl or, when L is —S— and n is 1, cyano or lower-alkoxythiocarbonyl or, when L is —SO$_2$— and n is 1, lower-alkyl or trifluoromethyl; and In the compound of formula I as described at pages 9–11 above $R_3$ is also di-lower-alkylamino and $R_4$ is hydrogen or from one to three substituents selected from those substituents described at pages 10–11 above and from carboxy-lower-alkoxy, lower-alkoxycarbonyl-lower-alkoxy and di-lower-alkylaminocarbonyloxy.

A compound of formula I wherein n is 0 and $R_1$ is 1,2,3-triazol-1-yl is prepared by condensation of the corresponding compound of formula I wherein $R_1$ is halo with an alkali metal azide and then cycloaddition of the resulting azide with the corresponding substituted or unsubstituted acetylene. The preferred alkali metal azide is sodium azide. The condensation is carried out with or without heating or cooling, preferably at room temperature, in an inert solvent, for example benzene, toluene or dimethylformamide, optionally using a crown ether, for example 18-crown-6 ether. The cycloaddition is preferably carried out in the same inert solvent with heating.

In addition to those particularly preferred compounds of formula I described at lines 8–15 of page 14 above also particularly preferred are compounds of formula I wherein m is 0, $R_2$ is hydrogen, $R_3$ is hydrogen, halo, primary or secondary lower-alkyl or lower-alkoxy, $R_4$ is hydrogen, hydroxy, lower-alkoxy, lower-alkoxy-lower-alkoxy, lower-alkoxy-poly-lower-alkyleneoxy, carboxy-lower-alkoxy or lower-alkoxycarbonyl-lower-alkoxy and:

n is 1, L is —O— and $R_1$ is phenyl substituted by halo, 1-(4-lower-alkylpiperazin-1-yl)carbonyl, 4-morpholinylsulfonyl, 4-thiamorpholinylsulfonyl or the S-dioxide thereof, 4-morpholinyl-lower-alkylaminocarbonyl, 4-morpholinyl-lower-alkoxycarbonyl, 1-(4-lower-alkylpiperazin-1-yl)sulfonyl, di-loweralkylamino-lower-alkylaminosulfonyl and/or 4-morpholinylcarbonyl or 1,2,5-thiadiazol-3-yl or 1,2,5-thiadiazol-3-yl substituted by 4-morpholinyl or isoxazolyl substituted by lower-alkoxycarbonyl; or n is 1, L is —S— and $R_1$ is 1,3,4-oxadiazol-2-yl substituted on any available carbon atom by furyl, benzyl, pyridinyl, pyrazinyl or phenyl; or n is 0 and $R_1$ is 1,2,3-triazol-1-yl or 1,2,3-triazol-2-yl substituted on any available carbon atom by cyano or lower-alkylsulfonyl.

EXAMPLES 41A–L

Further examples of compounds of formula I wherein m is 0 and $R_2$, $R_3$ and $R_4$ are each hydrogen were prepared from 2-(chloromethyl)saccharin (or, if noted, 2-(bromomethyl)saccharin) and in each example the corresponding $R_1$-$L_n$-H except as noted and are described in TABLE G.

TABLE G

| Example | $R_1$-$L_n$ | M.p. (°C.) From | Yield (%) Method |
|---|---|---|---|
| 41A | {5-[2-(1-piperidinyl)ethylthio]-1,3,4-thiadiazol-2-yl}thio | 100–101 EtOAc | 60 A |
| 41B | {5-[2-(diethylamino)ethyl]-1,3,4-thiadiazol-2-yl}thio | 93–94.5 $C_6H_{12}$/EtOAc | 44 B |
| 41C | {5-[2-(4-morpholinyl)ethylamino]-1,3,4-thiadiazol-2-yl}thio | 159–161 EtOAc | 57 B |
| 41D | 4,5-dicyanoimidazol-1-yl | 143–146 $CHCl_3$ | 50 D |
| 41E | trifluoromethylsulfonyl | 134–137 | 25 E |
| 41F | 2-formyl-4-nitrophenoxy | 168–171 EtOH/MeCN | I or J |
| 41G | 2-hydroxymethyl-4-nitrophenoxy | 150–152 | 92 G |
| 41H | 2-chloromethyl-4-nitrophenoxy | 148–(slow) | 30.6 H |
| 41I | (5,7-dichloroquinolin-8-yl)oxy | 220.5–222.5 EtOH/MeCN | 46 I |
| 41J | 4-chloromethyl-2-nitrophenoxy | 131–133 EtOH | 32 J |
| 41K | 4-(4-nitrophenylazo)phenoxy | 217–219 | 63 J |
| 41L | 2,4-dichloro-3-(4-methyl-1-piperazinylcarbonyl)phenoxy | >190* $Et_2O$ | 32 L |

Notes to TABLE G
A: By alkylation with 1-(2-chloroethyl)piperidine in dimethylformamide at room temperature of 2-[(5-mercapto-1,3,4-thiadiazol-2-yl)thiomethyl]saccharint prepared in turn by condensation of 2-(bromomethyl)saccharin and 1,3,4-thiadiazol-2,5-dithiol with sodium methoxide in ethanol at reflux in 38% yield (m.p. 204–206.5° C. from 1,2-dichloroethane, 38% yield).
B: From 2-(bromomethyl)saccharin with ethanol as solvent and sodium methoxide as base.
D: From 2-(bromomethyl) saccharin and tetrahydrofuran as solvent.
E: By oxidation of the corresponding sulfide.
G: By reduction of the compound of Example 41F.
H: By displacement of hydroxy in the compound of Example 41G by chloro.
I: With acetonitrile as solvent and methyltriazabicyclodecene as base.
J: With dimethylformamide as solvent and thallium ethoxide as base.
L: With methyl ethyl ketone as solvent and potassium carbonate as base.
*Hydrochloride salt.

EXAMPLES 42A–BU

Further examples of compounds of formula I wherein m is 0 except Example 42B wherein m is 1, $R_2$ and $R_4$ are each hydrogen and $R_3$ is isopropyl were prepared from 2-chloromethyl-4-isopropylsaccharin (Example 22E above) (or, if noted, 2-bromomethyl-4-isopropylsaccharin) and in each example the corresponding $R_1$-$L_n$-H except as noted and are described in TABLE H.

TABLE H

| Example | $R_1$-$L_n$ | M.p. (°C.) From | Yield (%) Method |
|---|---|---|---|
| 42A | (5-cyclohexylamino-1,3,4-thiadiazol-2-yl)thio | 202–205 EtOH | 51 A |
| 42B | (2-phenyltetrazol-5-yl)thio (m = 1) | 95–97 EtOH | 39.5 B |
| 42C | methylsulfonyl | 148.5–150.5 EtOH | 40.3 C |
| 42D | 1,1,3-trioxotetrahydro-1,2,5-thiadiazol-2-yl | Foam | 53 D |
| 42E | (2-methyl-4-pyron-3-yl)oxy | 136.5–138 EtOAc/$C_6H_6$ | 48 E |
| 42F | 4-[(4-methylpiperazin-1-yl)carbonyl]phenoxy | 160–165* $Et_2O$ | 60 F |
| 42G | (6-hydroxymethyl-4-pyron-3-yl)oxy | 144–145 EtOAc/$C_6H_{14}$ | 38 A |
| 42H | {5-[2-(4-morpholinyl)ethylthio]-1,3,4-thiadiazol-2-yl}thio | 53–93* iPrOH/$Et_2O$ | 87 H |
| 42I | 2,4-dichloro-6-(4-morpholinylsulfonyl)phenoxy | 153–155 EtOH | 53 I |
| 42J | 2-chloro-4-(4-morpholinylsulfonyl)phenoxy | 194–196 EtOH | 54 J |
| 42K | {5-[2-(1-piperidinyl)ethylthio]-1,3,4-thiadiazol-2-yl}thio | oil | 50% K |
| 42L | {5-[2-(diethylamino)ethyl]-1,3,4-thiadiazol-2-yl}thio | oil | 38 L |
| 42M | {5-[2-(dimethylamino)ethylthio]-1,3,4-thiadiazol-2-yl}thio | 124–125.5* iPrOH | 62 M |
| 42N | {5-[2-(4-morpholinyl)ethyl]-1,3,4-thiadiazol-2-yl}thio | 142–143* iPrOH | 71% L |
| 42O | {5-[2-(1-piperidinyl)ethyl]-1,3,4-thiadiazol-2-yl}thio | 149–150* EtOH | 61 O |
| 42P | (4,5-dichloropyridazin-3-yl)oxy | 183–186 $Et_2O$ | 40 E |
| 42Q | 4,5-di(methoxycarbonyl)-1,2,3-triazin-1-yl | 153–154 EtOAc/$C_6H_{14}$ | 30 Q |
| 42R | 2-methoxycarbonyl-5-methoxyphenoxy | 104–105 | 30 J |
| 42S | 2-fluoro-4-(4-morpholinylsulfonyl)phenoxy | 165–167 EtOH | 68.7 J |
| 42T | 2-chloro-4-(1,1-dioxo-4-thiamorpholinylsulfonyl)phenoxy | Not sharp EtOH | 29.6 T |
| 42U | 5-phenylsulfonyl-1,2,3-triazol-1-yl | 163.5–168 EtOAc | 32 Q |
| 42V | 4-trimethylsilyl-5-phenylsulfonyl-1,2,3-triazol-1-yl | 200.5–201.5 EtOAc | 22 Q |
| 42W | 4-methoxycarbonyl-1,2,3-triazol-1-yl | 192–193 EtOAc | 66 Q |
| 42X | (2-ethyl-4-pyron-3-yl)oxy | 93–98 | 85 X |
| 42Y | 5-methoxycarbonyl-1,2,3-triazol-1-yl | 150.5–151.5 EtOAc | 23 Q |
| 42Z | 4-ethoxycarbonyl-5-phenyl-1,2,3-triazol-1-yl | 177.5–179 EtOAc | 37 Q |
| 42AA | 4-phenyl-5-ethoxycarbonyl-1,2,3-triazol-1-yl | 117–119 EtOAc/$C_6H_{12}$ | 56 Q |
| 42AB | 2,6-difluoro-4-(4-morpholinylsulfonyl)phenoxy | 185–187 EtOH | 40 J |
| 42AC | 4,6-difluoro-2-(4-morpholinylsulfonyl)phenoxy | 176–178 EtOH | 38.6 J |
| 42AD | 4,5-difluoro-2-(4-morpholinylsulfonyl)phenoxy | 140.5–142.5 EtOH | 58.6 J |
| 42AE | (3-phenylcoumarin-7-yl)oxy | 145–147 EtOAc/$C_6H_{12}$ | 63 E |
| 42AF | (4-phenylcoumarin-7-yl)oxy | 219–221 MeCN | 53 E |
| 42AG | 4-fluoro-2-(4-morpholinylsulfonyl)phenoxy | 169–171 EtOH | 27.4 J |
| 42AH | 2,5-difluoro-4-(4-morpholinylsulfonyl)phenoxy | 158–160 EtOH | 44 J |
| 42AI | 3-[2-(4-morpholinyl)ethylaminocarbonyl]phenoxy | Foam* | 10 F |
| 42AJ | pentafluorophenoxy | 90–92 $C_6H_{14}$ | 10 F |
| 42AK | 2,4-dichloro-3-[2-(4-morpholinyl)ethoxycarbonyl]phenoxy | Foam* | 30 F |

TABLE H-continued

| Example | R₁-Lₙ | M.p. (°C.) From | Yield (%) Method |
|---|---|---|---|
| 42AL | (5-phenyl-1,3,4-oxadiazol-2-yl)thio | 132–134.5 EtOH | 60 AL |
| 42AM | 4-carboxy-1,2,3-triazol-1-yl | 182.5–183.5 MeCN | 21 Q |
| 42AN | 4-phenyl-5-(4-methylphenylsulfonyl)-1,2,3-triazol-1-yl | 173–174.5 EtOAc | 32 Q |
| 42AO | 4-(4-methylphenylsulfonyl)-5-phenyl-1,2,3-triazol-1-yl | 179–181.5 EtOAc | 40 Q |
| 42AP | (6-chloro-4-trifluoromethylcoumarin-7-yl)oxy | 169–170 EtOH | 29 X |
| 42AQ | (4-methylcoumarin-7-yl)oxy | 178–179.5 iPrOH | 18 E |
| 42AR | 3-[(4-methylpiperazin-1-yl)sulfonyl]phenoxy | >150* Et2O | 34 F |
| 42AS | 3-[2-(4-morpholinyl)ethoxy]phenoxy | 102–105* Et₂O | 35 F |
| 42AT | 3-{2-[(dimethylamino)ethyl]methylaminosulfonyl}phenoxy | 115–118* Et₂O | 60 F |
| 42AU | [3-(benzothiazol-2-yl)coumarin-7-yl]oxy | 239–240 MeCN | 30 E |
| 42AV | (saccharin-6-yl)oxy | 90–110 | 11 AV |
| 42AW | 4-phenylsulfonyl-1,2,3-triazin-1-yl | 219.5–220.5 EtOAc | 87 Q |
| 42AX | ethoxythiocarbonylthio | oil | 57 AX |
| 42AY | 2-fluoro-4-(4-morpholinylsulfonyl)phenylthio | 149–151 EtOH | 83.7 J |
| 42AZ | 4-ethylsulfonyl-5-isopropyl-1,2,3-triazin-1-yl | 137–139 EtOAc/C₆H₁₂ | 20 Q |
| 42BA | 4-isopropyl-5-ethylsulfonyl-1,2,3-triazin-1-yl | 150–152 EtOAc/C₆H₁₂ | 6–11 Q |
| 42BB | 2-fluoro-4-(4-morpholinylsulfonyl)phenylsulfinyl | 198–201 | 42.5 BB |
| 42BC | 2-fluoro-4-(4-morpholinylsulfonyl)phenylsulfonyl | 219–221 EtOH | 87.5 BC |
| 42BD | 4,5-di(aminocarbonyl)-1,2,3-triazin-1-yl | 261–262 MeCN | 68 Q |
| 42BE | 4,5-dicarboxy-1,2,3-triazin-1-yl (monosodium salt) | 211–215 THF | 15 Q |
| 42BF | 4,5-dicarboxy-1,2,3-triazin-1-yl | | Q, BF |
| 42BG | [4-(4-morpholinyl)-1,2,5-thiadiazol-3-yl]oxy | 132–134 EtOH | 50 J |
| 42BH | 4-methylsulfonylphenoxy | 147–150 | 79 J |
| 42BI | [4-(ethoxycarbonylmethyl)thiazol-2-yl]thio | 96–97 CCl₄/C₆H₁₂ | 20 BI |
| 42BJ | 4-trimethylsilyl-5-dimethylaminosulfonyl-1,2,3-triazol-1-yl | 196–198 MeCN | 91 Q |
| 42BK | 4-(1,1-dimethyl)ethyl-5-dimethylaminosulfonyl-1,2,3-triazol-1-yl | 207–209 EtOAC/C₆H₁₂ | 7 Q |
| 42BL | 4-dimethylaminosulfonyl-5-(1,1-dimethyl)ethyl-1,2,3-triazol-1-yl | 201–202 EtOAC/C₆H₁₂ | 3 Q |
| 42BM | 4-trimethylsilyl-1,2,3-triazol-1-yl | oil | 81 Q |
| 42BN | 2,6-dichlorophenoxy | 146–148 Et₂O/C₆H₁₄ | 70 F |
| 42BO | 2,4,6-trichlorophenoxy | 140–142 t-BuOMe | 28 BO |
| 42BP | 2,4-dichloro-3-(4-methyl-1-piperazinylcarbonyl)phenoxy | >175* Et₂O | 75 F |
| 42BQ | 2,4-dichloro-3-carboxyphenoxy | 194–196 C₆H₁₄/CH₂C₁₂ | 57 BQ |
| 42BR | 3-[2-(4-morpholinyl)ethoxycarbonyl]phenoxy | >115* Et₂O | 51 F |
| 42BS | 2,4-dichloro-3-[2-(4-morpholinyl)ethylaminocarbonyl]phenoxy | 149–152* Et₂O | 30 F |
| 42BT | 4-(4-morpholinylsulfonyl)phenoxy | glass | BT |
| 42BU | 4-trimethylsilyl-5-methoxycarbonyl-1,2,3-triazol-1-yl | 122.5–123.5 EtOAc/C6H12 | 68 Q |

Notes to TABLE H

A: With dimethylformamide as solvent and triethylamine as base.

B: In three steps by, first, condensation of the thallium salt of 4-isopropylsaccharin formed from 4-isopropylsaccharin and thallium ethoxide with 1-phenyl-5-(3-chloro-3-phenylthio-propyl)tetrazole in dimethylformamide in 77% yield, second, oxidation of the resulting 2-[3-(1-phenyltetrazol-5-yl)-1-(phenylthio)propyl]-4-isopropylsaccharin with m-chloro-perbenzoic acid in 87% yield and, third, thermal elimination of the resulting 2-[3-(1-phenyltetrazol-5-yl)-1-(phenylthio)propyl]-4-isopropylsaccharin in 59% yield.

C: In two steps, first, condensation of 2-(chloromethyl)-4-isopropylsaccharin with sodium methylthiolate and, second, oxidation of the resulting 2-(methylthio)-4-isopropylsaccharin.

D: With toluene as solvent, 1,1,3-trioxotetrahydro-1,2,5-thiadiazole and tetrabutylammonium bromide.

E: With dimethylformamide as solvent and sodium hydride as base.

F: With methyl ethyl ketone as solvent and potassium carbonate as base. *Hydrochloride salt.

H: In two steps, first, condensation of 2-(chloromethyl)-4-isopropylsaccharin with 1,3,4-thiadiazol-2,5-dithiol monopotassium salt in methanol in 83% yield and, second, condensation of the resulting 2-[(5-mercapto1,3,4-thiadiazol-2-yl)thiomethyl]-4-isopropylsaccharin with 4-(2-chloroethyl)morpholine hydrochloride in dimethylformamide as solvent and triethylamine as base in 87% yield. *Hydrochlcride salt.

I: With dichloromethane as solvent and diazabicycloundecene as base.

J: With acetonitrile as solvent and methyltriazabicyclodecene as base.

K: By alkylation of 2-[(5-mercapto-1,3,4-thiadiazol-2-yl)thiomethyl]-4-isopropylsaccharin (Example 42H) with 1-(2-chloroethyl)piperidine hydrochloride in dimethylformamide as solvent and triethylamine as base.

L: With ethanol as solvent and sodium methoxide as base.

M: By alkylation of 2-[(5-mercapto-1,3,4-thiadiazol-2-yl)thiomethyl]-4-isopropylsaccharin (Example 42H) with (2-chloroethyl)dimethylamine hydrochloride in dimethylformamide as solvent and triethylamine as base. *Maleate salt.

N: With ethanol as solvent and sodium methoxide as base. *Maleate salt.

O: With ethanol as solvent and triethylamine as base. *Maleate salt.

Q: In two steps, first, condensation of 2-(chloromethyl)-4-isopropylsaccharin with sodium azide and a catalytic amount of 18-crown-6 ether in benzene or benzene-tetrahydrofuran or benzene-dimethylformamide at room temperature and, second, cycloaddition of the resulting 2-(azidomethyl)-4-isopropylsaccharin with the corresponding acetylene, in this example dimethyl aceylenedicarboxylate, in the same solvent with or without heating.

T: In two steps, first, condensation of 2-(chloromethyl)-4-isopropylsaccharin and 2-chloro-4-(4-thiamorpholinyl)phenol with acetonitrile as solvent and methyltriazabicyclodecene as base in 74.7% yield and, second, oxidation of the resulting 2-[2-chloro-4-(4-thiamorpholinyl)phenoxymethyl]-4-isopropylsaccharin with m-chloroperbenzoic acid in 38.5% yield.

X: With dimethylformamide as solvent and cesium carbonate as base.

AV: In two steps, first, condensation of 2-(chloromethyl)-4-isopropylsaccharin and 2-benzyl-6-hydroxysaccharin with methyl ethyl ketone as solvent and potassium carbonate as base in 43% yield and, second, debenzylation by catalytic hydrogenation over palladium on carbon in methanol containing ammonium formate in 26% yield.

AX: With methyl ethyl ketone as solvent and potassium O-ethyldithiocarbonate.

BB: By oxidation of the compound of Example 42AY with one molar equivalent of m-chloroperbenzoic acid.

BC: By oxidation of the compound of Example 42BB with one molar equivalent of m-chloroperbenzoic acid.

BF: Obtained impure.

BI: With acetonitrile as solvent and sodium hydride as base.

BO: With dimethylformamide as solvent and potassium carbonate as base.

BQ: In two steps, first, condensation of 2-(chloromethyl)-4-isopropylsaccharin and benzyl 2,6-dichloro-3-hydroxybenzoate with dimethylformamide as solvent and sodium hydride as base and, second, debenzylation by catalytic hydrogenation over palladium on carbon in methanol containing acetic acid.

BT: With tetrahydrofuran as solvent and triethylamine as base.

EXAMPLES 43A–BY

Preparation of 2-Chloromethyl-4-isopropyl-6-methoxysaccharin

To a solution of 300 mL of N,N,N',N'-tetramethylethylenediamine (TMEDA, 1.99 moles) in 4 L of anhydrous ether was added 1550 mL of sec-BuLi (1.3M) and the mixture was cooled to −70° C. under a nitrogen atmosphere. A solution of 454.2 g of 2-isopropyl-4-methoxy-N,N-diethylbenzamide (1.82 moles) in 300 mL of anhydrous ether was added dropwise over 30 minutes. The temperature was maintained at or below −60° C. during the addition. After the addition the mixture was stirred at −70° C. for one hour, allowed to warm to −50° C., held at −50° C. for 30 minutes, then cooled back to −70° C. By cannulation tube a solution of 200 g of $SO_2$ in 200 mL of dry ether precooled to −40° C. was added under positive nitrogen pressure over a 20-minute period. The temperature of the reaction mixture during the addition was maintained below −40° C. A white powdery precipitate of aryllithium sulphinate separated out almost immediately. After the addition the cooling bath was removed and the mixture was stirred at ambient temperature for two hours, then cooled to −5° C. With continued stirring 190 mL of sulfuryl chloride (2.36 moles) was added dropwise over a 15-minute period while maintaining the temperature below 10° C. After further stirring for 30 minutes at 0°–5° C., a white insoluble precipitate was filtered off and washed with 2 L of anhydrous ether. Removal of the solvent at atmospheric pressure afforded the resulting sulfonyl chloride (a crude dark oil) was dissolved in 1.4 L of THF. The solution was cooled to −10° C., and 540 mL of concentrated aqueous ammonia (28%) was added in portions over 15 minutes. The temperature was kept at 15° C. or below throughout the addition. After stirring for 15 minutes at ambient temperature the THF and excess ammonia were removed under vacuum to give a dark oil, which was diluted with 6.0 L of water and acidified with 3N HCl to pH 1. The resulting light yellow solid was collected by filtration, washed with 800 mL of water, dried at 60° C. under vacuum for 18 hours and recrystallized from a mixture of 800 mL of ethyl acetate and 3 L of hexane to give 429 g (72%) of 2-aminosulfonyl-6-isopropyl-4-methoxy-N,N-diethylbenzamide, mp 122°–125° C.

A solution of 429.6 g of the diethylbenzamide (1.31 mole) in 1.5 L of acetic acid was refluxed for 20 hours, then cooled to room temperature. The solvent was removed under vacuum. The oily residue was dissolved in 6 L of water and the pH was adjusted to 1 with 6N HCl. The crude product was collected by filtration, washed with 2 L of water, dried at 60° C. under vacuum for 18 hours and recrystallized from ethyl acetate/hexane to give 303 g (91%) 4-isopropyl-6-methoxysaccharin, mp 188°.

To a suspension of 24 g of paraformaldehyde (0.8 mole) and 86.4 g of chlorotrimethylsilane (1.6 moles) in 200 mL of 1,2-dichloroethane was added 0.8 ml anhydrous tin(IV) chloride and the resulting solution stirred on a steam bath for one hour. 4-Isopropyl-6-methoxysaccharin (51.4 g, 0.2 mole) was added to the clear solution and the mixture was refluxed for 18 hours, cooled to room temperature and poured into water. The organic layer was separated, washed with 50 mL of 2N sodium hydroxide solution, dried over anhydrous magnesium sulfate and concentrated under vacuum. The residue was purified by crystallization from ethyl acetate/hexane to give 57 g (87%) of 2-chloromethyl-4-isopropyl-6-methoxysaccharin, mp 151°.

Examples 43A–CA of compounds of formula I wherein m is 0 except Example 43F wherein m is 1, $R_2$ is hydrogen, $R_3$ is isopropyl and $R_4$ is 6-methoxy were prepared from 2-chloromethyl-4-isopropyl-6-methoxysaccharin and in each example the corresponding $R_1$-$L_n$-H except as noted and are described in TABLE I.

TABLE I

| Example | $R_1$-$L_n$ | M.p. (°C.) From | Yield (%) Method |
|---|---|---|---|
| 43A | (1-phenyltetrazol-5-yl)thio | Foam | 83 A |
| 43B | [2-(4-morpholinylethyl)tetrazol-5-yl]thio | 144–145 | 71 B |
| 43C | 4-phenyl-5-thioxotetrazolin-1-yl | 188.5–189.5 | 69 C |
| 43D | 4-phenylsulfonyl-5-trimethyl-silyl-1,2,3-triazol-1-yl | 175–177 $C_6H_{12}/C_6H_6$ | 32 D |
| 43E | [5-(2-furyl)-1,3,4-oxadiazol-2-yl]thio | 125–127 EtOH | 70 E |
| 43F | (1-phenyltetrazol-5-yl)thio (m = 1) | 160–161.5 EtOH | F |
| 43G | (5-phenyl-1,3,4-oxadiazol-2-yl)thio | 136–137.5 EtOH | 53 E |
| 43H | [1-(3-succinoylaminophenyl)-tetrazol-5-yl]thio | 122–125 EtOH | 78.6 B |
| 43I | 2-benzoyl-4,5-dibromoimidazol-1-yl | 177–180 MeCN/EtOH | 32 I |
| 43J | (5-benzyl-1,3,4-oxadiazol-2-yl)-thio | 121–123 EtOH | 76 E |
| 43K | (5-hydroxy-6-methyl-6,7-dihydro-1H-1,2,4-triazolo[3,4-b][1,3]-thiazin-3-yl)thio | * | 51 K |
| 43L | [2-(3-pyridyl)-1,3,4-oxadiazol-5-yl]thio | 139–141 EtOH | 77.6 K |
| 43M | (3-ethoxy-4-methyl-1,2,4-triazol-5-yl)thio | 167–168 | 70 K |
| 43N | [5-(4-trifluoromethylphenyl)-1,3,4-oxadiazol-2-yl]thio | 201.5–203 EtOH | 72.7 K |
| 43O | [5-(4-methoxyphenyl)-1,3,4-oxadiazol-2-yl]thio | 138–139 EtOH | 85.1 K |
| 43P | [5-(4-pyridyl)-1,3,4-oxadiazol-2-yl]thio | 184–185 EtOH | 45.4 K |
| 43Q | [5-(4-biphenylyl)-1,3,4-oxadiazol-2-yl]thio | 153–155 EtOH | 78.9 K |
| 43R | [5-(2-pyrazinyl)-1,3,4-oxadiazol-2-yl]thio | 153–154 EtOH/MeCN | 54.5 K |
| 43T | [5-(2-pyridyl)-1,3,4-thiadiazol-2-yl]thio | 148–149 EtOH | 71.7 K |
| 43U | 2-thioxo-2,3-dihydro-1,3,4-oxadiazol-3-yl | 250–251 MeCN | 36 K |
| 43V | [5-(3-furyl)-1,3,4-oxadiazol-2-yl]thio | 109–111 EtOH | K |
| 43W | (4-methyl-5-ethoxycarbonyl-thiazol-2-yl)thio | 131–132 EtOH | K |
| 43X | 2-thioxo-2,3-dihydro-5-(2-pyridyl)-1,3,4-thiadiazol-3-yl | 275–276 K | |
| 43Y | (4-phenylthiazol-2-yl)thio | 121–122 EtOH | 63.0 K |
| 43Z | (4,5-dimethylthiazol-2-yl)thio | Noncrystalline | 53.6 K |
| 43AA | 2,3-dihydro-2-oxo-5-phenyl-1,3,4-thiadiazol-3-yl | 204–205 MeCN | 73 K |
| 43AB | [4-(4-morpholinyl)-1,2,5-thiadiazol-3-yl]thio | 124.5–125.5 EtOH | 48 K |
| 43AC | [5-(2-pyridyl)-1,3,4-oxadiazol-2-yl]thio | 161–163 EtOH/MeCN | 64.4 K |
| 43AD | (3-phenyl-2-thioxo-2,3-dihydro-1,3,4-thiadiazol-5-yl)thio | 112–114 EtOH | 73.6 AD |
| 43AE | 2,3-dihydro-2-oxo-5-phenyl-1,3,4-oxadiazol-3-yl | 190–191 | 61 K |
| 43AF | 4-(4-morpholinylsulfonyl)-3-trifluoromethylphenoxy | 201–203 EtOH | 58 K |
| 43AG | 2,5-difluoro-4-(4-morpholinyl-sulfonyl)phenoxy | 171–172 | 46 K |
| 43AH | 2,6-dichloro-4-(4,5-dihydro-oxazol-2-yl)phenoxy | 176–178 $Et_2O$ | 50 AH |
| 43AI | 4,5-dicyano-1,2,3-triazol-1-yl | 163.5–165 $CCl_4$ | I |
| 43AJ | 2,6-dichloro-4-(2-methyltetrazol-5-yl)phenoxy | 190–192 EtOH | 76 AH |
| 43AK | 4,5-dicyano-1,2,3-triazol-2-yl | 185–187 $C_6H_6$ | I |
| 43AL | 4,5-di(t-butylsulfonyl)-1,2,3-triazol-1-yl | 207.5–209 EtOAc | 87 D |

TABLE I-continued

| Example | R₁-Lₙ | M.p. (°C.) From | Yield (%) Method |
|---|---|---|---|
| 43AM | 3,5-difluoro-4-(4-morpholinyl-carbonyl)phenoxy | 146–149 | 70 K |
| 43AN | 3,5-difluorophenoxy | 127–129 | 79 K |
| 43AO | 4,5-di(1-piperidinylcarbonyl)-1,2,3-triazol-1-yl | 240–242 | 8 I |
| 43AP | 4,5-di(trifluoromethyl)-1,2,3-triazol-1-yl | 200.5–202.5 C₆H₆ | 71 D |
| 43AQ | 4,5-di-(1-piperidinylcarbonyl)-1,2,3-triazol-2-yl | 225–226 EtOAc | 64 I |
| 43AR | 3,5-difluoro-4-(4-morpholinyl-sulfonyl)phenoxy | Glass | 50 K |
| 43AS | 2-methylthio-5-methyl-6-oxo-1,2-dihydro-1,2,4-triazin-1-yl | 200–202 | 41 K |
| 43AT | [5-(3,5-dimethoxyphenyl)-1,3,4-oxadiazol-2-yl]thio | 144–145 EtOH | 75 K |
| 43AU | [5-(4,5-dimethoxyphenyl)-1,3,4-oxadiazol-2-yl]thio | 65–80 EtOH | 35.7 K |
| 43AV | cyanothio | 102–104 EtOH | 44.4 |
| 43AW | (4-methyl-5-oxo-6-hydroxy-4,5-dihydro-1,2,4-triazin-3-yl)thio | EtOAc | 39 AW |
| 43AX | 2,6-dichloro-4-ethoxycarbonyl-phenoxy | oil | K |
| 43AY | (cycloheptatrienon-2-yl)oxy | 148–149 | 47 AH |
| 43AZ | [5-(4-pentyloxyphenyl)-1,3,4-oxadiazol-2-yl]thio | 113–114 EtOH | 65.5 K |
| 43BA | (4-ethoxycarbonylisoxazol-5-yl)oxy | 158–160 EtOH | 14 K |
| 43BB | (2,5-dioxopyrrolidin-1-yl)oxy | 227–228 C₇H₁₆ | 54 BB |
| 43BC | 2-methyl-4,5-di(hydroxymethyl)-3-pyridyloxy | 167–168 Et₂O | 10 K |
| 43BD | 2,4-dichloro-3-[2-(4-morpholinyl)-ethoxycarbonyl]phenoxy | >130* Et₂O | 43 E |
| 43BE | 5-phenylsulfonyl-1,2,3-triazol-1-yl | 164–165 EtOAc | 25 D |
| 43BF | 2-diethylphosphonylphenoxy | 104–106 | 27 BF |
| 43BG | 2,6-difluoro-4-(4-morpholinyl-sulfonyl)phenoxy | 172–174 | 27 K |
| 43BH | 2,5-difluoro-4-(4-methyl-1-piperazinylsulfonyl)phenoxy | 201–203 | 37 BH |
| 43BI | 2,6-difluoro-4-(4-methyl-1-piperazinylsulfonyl)phenoxy | 201–203 | 8 BH |
| 43BJ | 3-benzyloxy-4,5-dihydro-5-oxo-1,2,4-oxadiazol-4-yl | 155.5–157 | 70 AH |
| 43BK | 1,2,5-thiadiazol-3-yl | 107–109 EtOH | 39.5 K |
| 43BL | {5-[4-[2-(2-methoxyethoxy)-ethoxy]phenyl]-1,3,4-oxadiazol-2-yl}thio | 106–108 | 79.7 K |
| 43BM | [5-(3,4-methylenedioxyphenyl)-1,3,4-oxadiazol-2-yl]thio | 162–163 EtOH/MeCN | K |
| 43BN | [5-(2,5-dimethoxyphenyl)-1,3,4-oxadiazol-2-yl]thio | 124–126 EtOH | 71 K |
| 43BO | (5-methoxycarbonylisoxazol-3-yl)oxy | 131–132 EtOH | K |
| 43BP | (1-methyl-2-ethoxycarbonylindol-3-yl)oxy | 150–152 | 38.9 AH |
| 43BQ | [5-(2-methoxyphenyl)-1,3,4-oxadiazol-2-yl]thio | oil | K |
| 43BR | (5-phenyloxazol-2-yl)thio | 128–129 EtOH | K |
| 43BS | 2-(4-methoxybenzoyl)indol-1-yl | 177–178 | 58 I |
| 43BT | 2-methyl-3-(2,6-dichlorobenzoyl)-indol-1-yl | 268–270 EtOAc | 86 I |
| 43BU | (2-phenyl-5-methylthiazol-4-yl)oxy | 157–158 EtOH | 51 K |
| 43BV | (2-methyl-5-phenylthiazol-4-yl)oxy | 102–103.5 EtOH | 11 K |
| 43BW | [1-(3-pyridyl)tetrazol-5-yl]thio | 134–136 EtOH | 63.6 K |
| 43BX | 2,3,5-trifluoro-4-(4-morpholinyl-sulfonyl)phenoxy | 170–171.5 EtOH | 49.3 K |
| 43BY | [1-(2,5-dimethoxyphenyl)tetrazol-5-yl]thio | 142–143 EtOH | 15.8 K |

Notes to TABLE I
A: With dimethylformamide as solvent and 1-phenyl-tetrazole-5-thiol sodium salt.
B: With dichloromethane as solvent and triethylamine as base.
C: With dimethylformamide as solvent and sodium methoxide as base.
D: In two steps, first, condensation of 2-(chloromethyl)-4-isopropyl-6-methoxysaccharin with sodium azide and a catalytic amount of 18-crown-6 ether in benzene or toluene at room temperature and, second, cycloaddition of the resulting 2-(azidomethyl)-4-isopropylsaccharin with the corresponding acetylene, in this example phenylsulfonyltrimethylsilyl-acetylene, in the same solvent with or without heating.
E: With methyl ethyl ketone as solvent and potassium carbonate as base.
*Hydrochloride salt.
F: In three steps by, first, condensation of the thallium salt of 4-isopropyl-6-methoxysaccharin formed from 4-isopropyl-6-methoxysaccharin and thallium ethoxide with 1-phenyl-5-(3-chloro-3-phenylthio-propyl)tetrazole in dimethylformamide in 57% yield, second, oxidation of the resulting 2-[3-(1-phenyltetrazol-5-yl)-1-(phenylthio)propyl]-4-isopropyl-6-methoxysaccharin with m-chloro-perbenzoic acid in 60.5% yield and, third, thermal elimination of the resulting 2-[3-(1-phenyltetrazol-5-yl)-1-(phenylthio)propyl]-4-isopropyl-6-methoxysaccharin in 75% yield.
I: With dimethylformamide as solvent and sodium hydride as base.
K: With acetonitrile as solvent and methyltriazabicyclo-decene as base.
*Mixture (1:1) of geometric isomers.
AD: With methyl ethyl ketone as solvent and 3-phenyl-2-thioxo-2,3-dihydro-1,3,4-thiadiazol-5-thiol potassium salt.
AH: With dimethylformamide as solvent and potassium carbonate as base.
AV: With acetone as solvent and potassium thiocyanate.
AW: With dimethylformamide as solvent and diisopropylethylamine as base.
BB: With acetonitrile as solvent and diisopropylethylamine as base.
BF: With tetrahydrofuran as solvent and potassium t-butoxide as base.
BH: With acetonitrile-dimethylformamide as solvent and methyltriazabicyclodecene as base.

EXAMPLE 44

A solution of 2-chloromethyl-4-ethyl-5,7-dimethoxysaccharin (Example 22L, 0.4 g) and 1-phenyltetrazol-5-thiol sodium salt (0.28 g) in dimethylformamide (3 mL) was heated at 110° C. for two hours, then poured into water. Recrystallization of the resulting solid from ethanol-water afforded 2-(1-phenyltetrazol-5-yl) thiomethyl-4-ethyl-5,7-dimethoxysaccharin, 0.44 g, 74% yield, mp 162°–164° C.

EXAMPLE 45

A. A solution of 5-chloro-2-benzyl-2H-isothiazol-3-one-1-oxide (Example 26A, 1.50 g) and 1-methoxy-3-trimethylsilyloxybutadiene (d=0.885, 1.30 mL) was heated in a pressure tube at 65° C. overnight. More 1-methoxy-3-trimethylsilyloxybutadiene (0.74 mL) was added and the solution was again heated in a pressure tube at 65° C. overnight then stripped of volatiles. Dichloromethane was added, the mixture was stripped of volatiles, and the addition and stripping were repeated, finally under high vacuum. Dichloromethane was added to the golden amber oil, which solidified after several hours affording 2-benzyl-6-hydroxy-1,2-benzisothiazol-(1H)-3-one-1-oxide (1.16 g, 68% yield).

B. A solution of 2-benzyl-6-hydroxy-1,2-benzisothiazol-(1H)-3-one-1-oxide (3.75 g) in methanol (75–100 mL) was added dropwise to a solution of o-monoperphthalic acid magnesium salt (8.14 g) in water (70–100 mL) at room temperature. Methanol was (200–250 mL) added to dissolve the resulting precipitate, and the solution was stirred overnight at room temperature. An equal volume of water was added, and the mixture was extracted with dichloromethane. The dichloromethane extract was washed with water and saturated aqueous sodium chloride solution, dried over sodium sulfate and stripped of dichloromethane. A solution of the resulting solid (4.17 g) in dichloromethane was washed with water and saturated aqueous sodium chloride solution, dried over sodium sulfate and stripped of dichloromethane, affording 2-benzyl-6-hydroxysaccharin (3.87 g, 98% yield).

C. A mixture of 2-benzyl-6-hydroxysaccharin (0.86 g), 2-bromoethyl 2-methoxyethyl ether (d=1.347, 0.45 mL), potassium carbonate (1.24 g), methyl ethyl ketone (50 mL) and dimethylformamide (2 mL) was heated under reflux for five hours, then poured into ice-water (500 mL). The resulting solid was collected, washed with water and dried affording 2-benzyl-6-[2-(2-methoxyethoxy)ethoxy]saccharin (0.92 g, 78% yield, mp 86°–88° C.).

D. A mixture of 2-benzyl-6-[2-(2-methoxyethoxy)-ethoxy]saccharin (2.05 g), methanol (75–100 mL), ammonium formate (1.10 g) and palladium on carbon (10%, 1.0 g) was heated under reflux for 40 minutes, allowed to cool and filtered. The filtrate was stripped of volatiles affording 6-[2-(2-methoxyethoxy)-ethoxy]saccharin ammonium salt, a mixture of which with chloromethyl phenyl sulfide (0.79 g) and dimethylformamide was heated for eight hours at 100° C., stirred overnight at room temperature, and poured into ice-water (600 mL). The resulting mixture was extracted with dichloromethane. The dichloromethane extract was washed with water and saturated aqueous sodium chloride solution, dried over sodium sulfate and stripped of dichloromethane. Column chromatography of the residue (1.70 g) on silica gel using dichloromethane-acetone (98:2) as eluant and again using dichloromethane-acetone (99:1) as eluant afforded 2-phenylthiomethyl-6-[2-(2-methoxyethoxy)-ethoxy]saccharin (0.96 g, 45% yield).

E. Sulfuryl chloride (0.34 g) was added dropwise with stirring to a solution of 2-phenylthiomethyl-6-[2-(2-methoxyethoxy)ethoxy]saccharin (0.96 g) in dichloromethane. Stirring was continued at room temperature for three hours and the solution was stripped of volatiles. Dichloromethane was added and the solution was stripped again. Hexane was added to the residue and the mixture was stirred at room temperature overnight. The resulting white solid was collected and dried affording 2-chloromethyl-6-[2-(2-methoxyethoxy)-ethoxy]saccharin (0.69 g, 89% yield, mp 113°–115° C.).

F. By a method similar to that of Example 44 condensation of 2-chloromethyl-6-[2-(2-methoxyethoxy)-ethoxy] saccharin (34 g.) and 1-phenyltetrazol-5-thiol sodium salt (0.19 g) in methyl ethyl ketone at 60° C. and purification of the product (470 mg) by column chromatography on silica gel first with dichloromethane and then with dichloromethane-acetone (up to 97:3) as eluant afforded 2-(1-phenyltetrazol- 5-yl)thiomethyl-6-[2-(2-methoxyethoxy)ethoxy]saccharin as an oil (390 g, 82% yield).

EXAMPLE 46

A solution of 2-(5-phenyl-1-tetrazolyl)thiomethyl-4-ethylsaccharin (Example 30AE, 0.020 g) and 1-phenyltetrazol-5-thiol sodium salt (0.0026 g) in dimethylformamide (1 mL) was heated at 100° C. for three days, then poured into water. Recrystallization of the resulting solid from ethanol-water afforded 2-(4-phenyl-5-thioxo-1-tetrazolyl)methyl-4-ethylsaccharin, 0.012 g, 60% yield, mp 127°–129° C.

EXAMPLE 47

A. By the method of Example 22A 3,4-dimethoxy-2-propyl-N,N-dimethylbenzamide (9.2 g) was aminosulfonylated with sulfur dioxide and hydroxylamine-O-sulfonic acid (5.6 g) to give 2-aminosulfonyl-4,5-dimethoxy-6-propyl-N,N-dimethylbenzamide (7.4 g, 63% yield), which was cyclized in quantititive yield to 4-propyl-5,6-dimethoxysaccharin, phenylthiomethylation of which with chloromethyl phenyl sulfide (1.42 mL) gave 2-phenylthiomethyl-4-propyl-5,6-dimethoxy-saccharin (4.07 g), reaction of part (3.59 g) of which with sulfuryl chloride (2.12 mL) gave 2-chloromethyl-4-propyl-5,6-dimethoxysaccharin, 2.84 g, 97% yield.

B. By the method of Example 44 condensation of 2-chloromethyl-4-propyl-5,6-dimethoxysaccharin (0.6 g) and 1-phenyltetrazol-5-thiol sodium salt (0.36 g) in dimethylformamide (5 mL) and purification of the product by column chromatography on silica gel using ethyl acetate-hexane (3:7) as eluant followed by trituration with hexane afforded 2-(1-phenyltetrazol-5-yl)thiomethyl-4-propyl-5,6-dimethoxysaccharin, 0.65 g, 76% yield, mp 145°–146° C.

EXAMPLE 48

A. By the method of Example 22A 2-aminosulfonyl-4,5-dimethoxy-6-isopropyl-N,N-dimethylbenzamide (10.75 g) was prepared and cyclized to 4-isopropyl-5,6-dimethoxysaccharin (mp 186°–188° C. from ether-hexane), phenylthiomethylation of part (5 g) of which with chloromethyl phenyl sulfide (2.48 mL) gave 2-phenylthiomethyl-4-isopropyl-5,6-dimethoxysaccharin (4.07 g), reaction of which with sulfuryl chloride (three molar equivalents) gave 2-chloromethyl-4-isopropyl-5,6-dimethoxysaccharin, 85% yield, mp 117°–119° C. from ethyl acetate-hexane.

B. By the method of Example 44 condensation of 2-chloromethyl-4-isopropyl-5,6-dimethoxysaccharin (1.46 g) and 1-phenyltetrazol-5-thiol sodium salt (0.92 g) in dimethylformamide (5 mL) and recrystallization of the product from ethanol-water afforded 2-(1-phenyltetrazol-5-yl)thiomethyl-4-isopropyl-5,6-dimethoxy-saccharin, 1.05 g, 51% yield, mp 69°–71° C.

EXAMPLE 49

A. Ethanethiol (43.9 g) was added with stirring to a suspension of aluminum chloride (62.74 g) in chloroform (500 mL) at 0° C. To the resulting solution was added a solution of 4-isopropyl-6-methoxysaccharin (20.0 g) in chloroform (550 mL) during 30 minutes. The resulting solution was warmed to and maintained at 60° C. for 3–4 hours, then poured into ice-water acidified with hydrochloric acid. The resulting solid was collected by filtration, washed with water and dried affording 4-isopropyl-6-hydroxysaccharin, 18.4 g., 97% yield.

B. By the method of Example 21 phenylthiomethylation of 4-isopropyl-6-hydroxysaccharin (0.004 mole) with chloromethyl phenyl sulfide (0.61 mL) gave 2-phenylthiomethyl-4-isopropyl-6-hydroxy-saccharin (0.32 g, 21% yield), reaction of which with sulfuryl chloride (0.73 g) gave 2-chloromethyl-4-isopropyl-6-hydroxysaccharin, 84% yield, mp 149°–150° C.

C. By the method of Example 44 condensation of 2-chloromethyl-4-isopropyl-6-hydroxysaccharin (0.3 g) and 1-phenyltetrazol-5-thiol sodium salt (0.23 g) in dimethylformamide (10 mL) and flash chromatography of the resulting product on silica gel using hexane-ethyl acetate (7:3) as eluant afforded 2-(1-phenyl-tetrazol-1-yl)thiomethyl-4- isopropyl-6-hydroxy-saccharin, 0.3 g, 67% yield, mp 188.5°–189.5° C.

EXAMPLE 50

A. A solution of 5-chloro-2-benzyl-2H-isothiazol-3-one-1-oxide (Example 26A, 5.8 g) and 2-ethoxyfuran (3.76 g) in benzene (40 mL) was heated to 50° C. More benzene (30 mL) was added to the solidified reaction mixture, which was then heated under reflux for 15 minutes, then at 70° C. for 45 minutes, then chilled overnight in the refrigerator. The resulting pale yellow solid was collected, washed with cold benzene and dried affording 2-benzyl-4-ethoxy-7-hydroxy-1,2-benzisothiazol-(1H)-3-one-1-oxide, 3.05 g, 40% yield.

B. m-Chloroperbenzoic acid (8.6 g) was added with stirring to solution of 2-benzyl-4-ethoxy-7-hydroxy-1,2-benzisothiazol-(1H)-3-one-1-oxide (7.9 g) in dichloromethane (about 500 mL) and methanol (31 mL). Stirring was continued for several hours, more m-chloroperbenzoic acid (8.6 g) was added and stirring was continued for several days. Dichloromethane was added. The solution was washed with water. The solid which separated when the solution was washed again with water was collected (2.33 g, mp 196°–199° C.). More solid separated when the dichloromethane layer was washed with saturated aqueous sodium chloride solution and was collected (4.10 g, mp 196°–199° C.). Both solids were determined to be 2-benzyl-4-ethoxy-7-hydroxysaccharin.

C. A mixture of 2-benzyl-4-ethoxy-7-hydroxysaccharin (1.0 g), allyl bromide (0.36 g), potassium carbonate (0.62 g) and methyl ethyl ketone (about 20 mL) was heated at 80° C. for one hour. More allyl bromide (0.36 g) was added and heating at 80° C. was continued for one and one-half hours. The mixture was cooled and poured into ice-water (500 mL). The solid was collected affording 2-benzyl-4-ethoxy-7-allyloxysaccharin, 1.08 g, 96% yield, mp 148°–149° C.

D. A mixture of 2-benzyl-4-ethoxy-7-allyloxysaccharin (0.25 g) and triglyme was heated at 200° C. for 20 minutes, examined for extent of reaction by thin layer chromatography, heated at 200° C. for 20 minutes more, stirred overnight and poured into ice-water. The resulting tacky, brown solid was dissolved in dichloromethane. The dichloromethane solution was washed with saturated aqueous sodium chloride solution, dried over sodium sulfate and stripped of dichloromethane. Column chromatography of the residue (0.29 g) on silica using dichloromethane and dichloromethane-acetone (up to 99:1) as eluants afforded 2-benzyl-4-ethoxy-6-allyl-7-hydroxysaccharin (90 mg, 36% yield) whose mass spectrogram showed a molecular ion at mass 373.

E. A mixture of 2-benzyl-4-ethoxy-6-allyl-7-hydroxysaccharin (2.45 g), potassium carbonate (2.76 g) and methyl iodide (1.84 g) in acetone was heated at 50° C. with stirring for two hours, then poured with stirring into ice-water (500 mL). The resulting gooey precipitate crystallized overnight affording 2-benzyl-4-ethoxy-6-allyl-7-methoxysaccharin, 2.35 g, 92% yield, mp 92°–94° C.

F. By the method of part D of Example 45 2-benzyl-4-ethoxy-6-allyl-7-methoxysaccharin (2.35 g) was simultaneously debenzylated and hydrogenated with ammonium formate (1.51 g) and palladium on carbon (10%, 1.25 g) in methanol (70–100 mL) affording 4-ethoxy-6-propyl-7-methoxysaccharin ammonium salt (1.94 g), phenylthiomethylation of which with chloromethyl phenyl sulfide (0.95 g) in dimethylformamide and purification of the product (a yellow oil, 2.67 g) by column chromatography on silica gel using dichloromethane-hexane (80:20) as eluant afforded 2-phenylthiomethyl-4-ethoxy-6-propyl-7-methoxysaccharin, 0.85 g, 34% yield.

G. By the method of part E of Example 45 2-phenylthiomethyl-4-ethoxy-6-propyl-7-methoxysaccharin (0.85 g) was reacted with sulfuryl chloride (0.30 g) in dichloromethane and purified with hexane affording 2-chloromethyl-4-ethoxy-6-propyl-7-methoxysaccharin, 0.62 g, 89% yield, mp 131°–133° C.

H. By the method of part F of Example 45 condensation of 2-chloromethyl-4-ethoxy-6-propyl-7-methoxysaccharin (0.62 g) and 1-phenyltetrazol-5-thiol sodium salt (0.36 g initially and a small amount more after 3.5 hours reaction time, total reaction time 8 hours) and isolation of the oily product by extraction with dichloromethane and purification thereof first by column chromatography on silica gel using dichloromethane as eluant and then by crystallization of the resulting oil (0.62 g., 71% yield) from ethanol gave 2-(1-phenyltetrazol-5-yl)thiomethyl-4-ethoxy-6-propyl-7-methoxysaccharin, mp 110°–111° C.

EXAMPLE 51

A. s-Butyllithium (0.87M in cyclohexane, 20.4 mL) was added dropwise during one hour with stirring at –78° C. to a solution of 4-ethyl-5,7-dimethoxysaccharin (Example 22L, 2.2 g) in tetrahydrofuran (100 mL). After continued stirring at –78° C. for one hour methyl iodide (1.5 mL) was added. Stirring was continued at –78° C. for 15 minutes, the temperature was allowed to rise to room temperature, and the mixture was quenched in water. Aqueous sodium hydroxide (0.5%, 200 mL) was added. The mixture was washed with ethyl acetate (200 mL), acidified with concentrated hydrochloric acid and extracted with ethyl acetate (200 mL). The ethyl acetate extract was washed with aqueous sodium thiosulfate (10%, 50 mL) and saturated aqueous sodium chloride (50 mL), dried over sodium sulfate and stripped of ethyl acetate affording 4-ethyl-5,7-dimethoxy-6-methylsaccharin (0.73 g, 32% yield).

B. By the method of Example 21 phenylthiomethylation of 4-ethyl-5,7-dimethoxy-6-methylsaccharin (0.65 g) with chloromethyl phenyl sulfide (0.24 mL) gave 2-phenylthiomethyl-4-ethyl-5,7-dimethoxy-6-methylsaccharin, reaction of which with sulfuryl chloride gave 2-chloromethyl-4-ethyl-5,7-dimethoxy-6-methylsaccharin, 0.16 g, 22% yield.

C. By the method of Example 44 condensation of 2-chloromethyl-4-ethyl-5,7-dimethoxy-6-methylsaccharin (0.17 g) and 1-phenyltetrazol-5-thiol sodium salt (0.084 g) in dimethylformamide (4 mL) and purification of the product by flash column chromatography on silica gel using hexane-ethyl acetate (75:25) as eluant afforded 2-(1-phenyltetrazol-5-yl)thiomethyl-4-ethyl-5,7-dimethoxy-6-methylsaccharin, 0.15 g, 76% yield, mp 44°–46° C.

EXAMPLE 52

A. A mixture of 2-benzyl-4-ethoxy-7-hydroxysaccharin (part B of Example 50, 0.5 g), t-butyl bromoacetate (0.3 g, 0.25 mL), potassium carbonate (0.30 g) and methyl ethyl ketone (about 10 mL) was heated at 70°–80° C. for about one hour, let cool and poured into ice-water (400 mL). The mixture was stirred overnight and the solid was collected affording 2-benzyl-4-ethoxy-7-(t-butoxycarbonylmethoxy) saccharin, 0.58 g, 86% yield.

B. By the method of part D of Example 45 in two successive preparations 2-benzyl-4-ethoxy-7-(t-butoxycarbonylmethoxy) saccharin (0.5 g, 6.5 g) was debenzylated with ammonium formate (0.25 g, 3.66 g) and palladium on carbon (10%, 0.25 g, 2 g) in methanol affording 4-ethoxy-7-(t-butoxycarbonylmethoxy)saccharin ammonium salt (0.44 g, 5.63 g), phenylthiomethylation of which with chloromethyl phenyl sulfide (0.2 g, 2.38 g) in dimethylformamide and purification of the combined products (0.46 g, 6.42 g) by column chromatography on silica gel using dichloromethane and dichloromethane-acetone (98:2) as eluants afforded 2-phenylthiomethyl-4-ethoxy-7-(t-butoxycarbonylmethoxy)saccharin, 1.92 g, 40% yield.

C. By the method of part E of Example 45 2-phenylthiomethyl-4-ethoxy-7-(t-butoxycarbonylmethoxy) saccharin (1.92 g) was reacted with sulfuryl chloride (0.54 g) in dichloromethane at about 5° C. and purified with hexane affording 2-chloromethyl-4-ethoxy-7-(t-butoxycarbonylmethoxy)saccharin, 1.54 g, 95% yield, mp 117°–119° C.

D. By the method of part F of Example 45 condensation of 2-chloromethyl-4-ethoxy-7-(t-butoxycarbonylmethoxy) saccharin (1.42 g) and 1-phenyltetrazol-5-thiol sodium salt (0.70 g initially and a small amount more after 6 hours reaction time, total reaction time 8 hours) and isolation of the product (1.20 g) by extraction with dichloromethane and purification of part (0.42 g) thereof by column chromatography on silica gel using dichloromethane-acetone (up to 98:2) as eluant afforded 2-(1-phenyltetrazol-5-yl) thiomethyl-4-ethoxy-7-(t-butoxycarbonylmethoxy) saccharin, 300 mg, 71% yield, mp 110°–112° C.

EXAMPLE 53

A solution of 2-(1-phenyltetrazol-5-yl)thiomethyl-4-ethoxy-7-(t-butoxycarbonylmethoxy)saccharin (Example 52, 0.47 g) in trifluoroacetic acid (5–10 mL) and dichloromethane (5–10 mL) was stirred at room temperature for two hours, then stripped of volatiles, then stripped three times more from dichloromethane, then stripped once more from acetone. A solution of the residual oil in acetone (1 mL) was added to ice-water (100 mL) containing concentrated hydrochloric acid (1 mL). The resulting solid was collected, washed with water and dried (0.34 g). A solution thereof in dichloromethane was eluted through silica gel in a 15-mL sintered glass funnel with chloroform-methanol (95:5) affording 2-(1-phenyltetrazol-5-yl)thiomethyl-4-ethoxy-7-carboxymethoxysaccharin, 70 mg, 17% yield, mp 187°–189° C.

EXAMPLE 54

A. Bromination of 1,2-dimethoxy-4-isopropylbenzene (31 g) with N-bromosuccinimide on Kieselgel in tetrachloridemethane by the method of Hisatoshi et al. (Bulletin of the Chemical Society of Japan, vol. 32, pp. 591–593, 1989) gave 5-bromo-1,2-dimethoxy-4-isopropylbenzene, lithiation of which with n-butyllithium in ether gave 5-lithio-1,2-dimethoxy-4-isopropylbenzene, diethylaminocarbonylation of which in the same solvent gave 2-isopropyl-4,5-dimethoxy-N,N-diethylbenzamide (15.2 g) as a viscous oil.

B. By the method of Example 43 aminosulfonylation of this 2-isopropyl-4,5-dimethoxy-N,N-diethylbenzamide with s-butyllithium, sulfur dioxide, sulfuryl chloride and concentrated ammonia gave 2-isopropyl-4,5-dimethoxy-6-aminosulfonyl-N,N-diethylbenzamide (4.5 g, mp 181°–182° C.), cyclization of which in acetic acid gave 4-isopropyl-6,7-dimethoxysaccharin, 2.86 g, mp 210°–212° C.

C. Diisopropylethylamine (0.5 mL) was added to a solution of 4-isopropyl-6,7-dimethoxysaccharin (0.5 g) in dimethylformamide (3 mL). After 15 minutes chloromethyl phenyl sulfide (0.35 g) was added. The mixture was heated at 80° C. for 16 hours, diluted with ethyl acetate, washed with aqueous sodium carbonate solution, hydrochloric acid (3N) and saturated aqueous sodium chloride solution, dried over sodium sulfate, and stripped of solvents. Purification of the residue by flash chromatography on silica gel using dichloromethane as eluant gave 2-phenylthiomethyl-4-isopropyl-6,7-dimethoxysaccharin (0.35 g), chlorination of which with sulfuryl chloride (0.1 mL) in dichloromethane (3 mL) and purification of the product by trituration with hexane gave 2-chloremethyl-4-isopropyl-6,7-dimethoxysaccharin, 0.3 g.

D. By a method similar to that of Example 44 condensation of 2-chloromethyl-4-isopropyl-6,7-dimethoxysaccharin (0.095 g) and 1-phenyltetrazol-5-thiol sodium salt (0.120 g) in acetonitrile (2 mL) and purification of the product by crystallization from ethanol afforded 2-(1-phenyltetrazol-5-yl)thiomethyl-4-isopropyl-6,7-dimethoxy-6-methylsaccharin, 0.099 g, 70% yield, mp 169°–171° C.

EXAMPLE 55

A. By the methods of parts D and E of Example 45 debenzylation of 2-benzyl-4-ethoxy-7-hydroxysaccharin (part B of Example 50) with ammonium formate and palladium on carbon in methanol gave 4-ethoxy-7-hydroxysaccharin ammonium salt, phenylthiomethylation of which with chloromethyl phenyl sulfide in dimethylformamide gave 2-phenylthiomethyl-4-ethoxy-7-hydroxysaccharin, reaction of which with sulfuryl chloride in dichloromethane gave 2-chloromethyl-4-ethoxy-7-hydroxysaccharin.

B. By the method of part F of Example 45 condensation of 2-chloromethyl-4-ethoxy-7-hydroxysaccharin (1.95 g) and 1-phenyltetrazol-5-thiol sodium salt (1.5 g, reaction time about 8 hours) and purification of part of the product (2.5 g., 88% yield) from ethanol gave 2-(1-phenyltetrazol-5-yl)thiomethyl-4-ethoxy-7-hydroxysaccharin, mp 178°–180° C.

EXAMPLE 56

A mixture of 2-(1-phenyltetrazol-5-yl)thiomethyl-4-ethoxy-7-hydroxysaccharin (Example 55, 0.5 g), dimethylcarbamyl chloride (0.14 mL, 0.16 g), diazabicyclooctane (0.27 g) and N,N-dimethylacetamide (20 mL) was heated at 80° C. for 4–5 hours, cooled and poured with stirring into ice-water (400 mL). Column chromatography of the resulting solid on silica gel by elution with dichloromethane and dichloromethane-acetone (up to 98:2) gave first 2-(4-phenyl-5-thioxo-1-tetrazolyl)methyl-4-ethoxy-7-dimethylaminocarbonylsaccharin (mp 172°–173° C. after recrystallization from ethanol) and then 2-(1-phenyltetrazol-5-yl)thiomethyl-4-ethoxy-7-dimethylaminocarbonyloxysaccharin (mp 145°–146° C. after sonication in ether).

EXAMPLE 57

2-(1-phenyltetrazol-5-yl)thiomethyl-4-isopropyl-5,6-dimethoxy-saccharin (0.48 g) was added with stirring at 0° C. to a solution of aluminum chloride (0.4 g) and ethanethiol (0.15 mL) in chloroform (3 mL). The temperature was allowed to rise to and remain at room temperature for 18 hours. The reaction mixture was passed through silica gel with ethyl acetate-hexane (2:3) as eluant affording as a colorless oil 2-(1-phenyltetrazol-5-yl)thiomethyl-4-isopropyl-5-hydroxy-6-methoxy-saccharin, 0.3 g, 77% yield, whose structure was proven by proton and carbon-13 magnetic resonance, mass spectrometric and nuclear Overhauser enhancement analyses. The latter analysis showed 19% enhancement of the methoxy protons signal and 10% enhancement of the C-7 proton signal.

BIOLOGICAL TEST RESULTS

In the test of elastase inhibition using human leukocyte elastase described above at pages 89–90 the compounds of formula I of Examples 41–57 showed $K_i^*$ values in the range from 0.024 nM (Example 43AL) to 1000 nM (Example 42D, for example).

ADDITIONAL BACKGROUND OF THE INVENTION

Additional Information Disclosure Statement

Dunlap et al. PCT Application WO 90/13549 published Nov. 15, 1990 describes saccharin derivatives useful as proteolytic enzyme inhibitors having the structural formula:

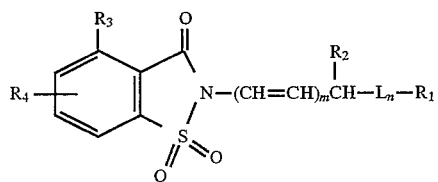

wherein:

L is —O—, —S—, —SO— or —SO$_2$—;

m and n are each independently 0 or 1;

R$_1$ is halogen, lower-alkanoyl, 1-oxo-phenalenyl, phenyl (or phenyl substituted by halogen, lower-alkyl, lower-alkoxy, nitro, amino, lower-alkylamino or di-lower-alkyl-amino) or heterocyclyl selected from 1H-(5-tetrazolyl), 5-oxo-1-tetrazolyl, 5-thioxo-1-tetrazolyl (when R$_2$ as defined hereinbelow is other than phenylthio), pyrimidinyl, 2-benzoxazolyl, 2-benzothiazolyl, 2-phthalimidyl, 2-(1,3,4-thiadiazolyl), 5-(1,2,4-thiadiazolyl), 5-thioxo-3-(1,2,4-thiadiazolyl), 4-(5-oxo-1,3,4-thiadiazolyl), 4-5-thioxo-1,3,4-thiadiazolyl), 3-(1,2,4-triazolyl), 4-(1,2,4-triazolyl), (1,2,3-triazolyl), 2 -imidazolyl or 3-(1,2,4-triazolo[4,3-a]-pyridinyl), or such heterocyclyl groups substituted on any available nitrogen atom by lower-alkyl, hydroxy-lower-alkyl, cycloalkyl, 2-, 3- or 4-pyridinyl, carboxy-lower-alkyl, lower-alkoxy-carbonyl-lower-alkyl, aminocarbonyl-lower-alkyl, lower-alkylaminocarbonyl-lower-alkyl, di-lower-alkylamino-carbonyl-lower-alkyl, amino-lower-alkyl, lower-alkylamino-lower-alkyl, di-lower-alkylamino-lower-alkyl, 4-morpholinyl-lower-alkyl, 1-piperidinyl-lower-alkyl, 1-pyrrolidinyl-lower-alkyl or phenyl (or phenyl substituted by amino, lower-alkyl-amino, di-lower-alkylamino, lower-alkanamido, N-lower-alkyl-lower-alkanamido, carboxy-lower-alkanamido, carboxy, carbo-lower-alkoxy, lower-alkoxy or halogen), or such heterocyclyl groups substituted on any available carbon atom by nitro, lower-alkyl, amino, lower-alkylamino, di-lower-alkylamino, cycloalkylamino, mercapto, lower-alkylthio, amino-lower-alkylthio, lower-alkylamino-lower-alkylthio, di-lower-alkyl-amino-lower-alkylthio, 4-morpholinyl-lower-alkylthio, 1-piperidinyl-lower-alkylthio, 1-pyrrolidinyl-lower-alkylthio, carbo-lower-alkoxy or phenyl (or phenyl substituted by amino, lower-alkylamino, di-lower-alkylamino, lower-alkanamido, N-lower-alkyl-lower-alkanamido, lower-alkyl, lower-alkoxy or halogen);

R$_2$ is hydrogen, carbo-lower-alkoxy, phenyl or phenylthio;

R$_3$ is hydrogen, halogen, primary or secondary lower-alkyl, lower-alkoxy, carbo-lower-alkoxy, phenyl, fluoro-lower-alkyl, lower-alkenyl or cyano;

R$_4$ is hydrogen or from one to two substituents selected from halogen, cyano, nitro, amino, lower-alkanamido, phenyl-lower-alkanamido, diphenyl-lower-alkanamido, lower-alkylsulfonylamino, polyfluoro-lower-alkylsulfonylamino, aminosulfonyl, lower-alkyl, polyhalo-lower-alkyl, cycloalkyl, polyhalo-lower-alkoxy, hydroxy, lower-alkoxy, carboxy, hydroxymethyl, formyl, aminomethyl, lower-alkylsulfonyl, polyhalo-lower-alkylsulfonyl, lower-alkylsulfonyl-aminosulfonyl and lower-alkoxypoly-lower-alkyleneoxy; and wherein the —CHR$_2$— group is always appended either to a hetero atom of the L moiety as defined above or it is appended to a hetero atom of the R$_1$ moiety, with the provisos that (i) when m and n are 0 and R$_2$, R$_3$ and R$_4$ are all hydrogen, R$_1$ cannot be halogen; (ii) when m is 0, n is 1, L is —S— and R$_2$, R$_3$ and R$_4$ are each hydrogen, R$_1$ cannot be 1-phenyl-1H-(5-tetrazolyl); (iii) when m is 0, n is 1, L is —O— or —S— and R$_2$, R$_3$ and R$_4$ are all hydrogen, R$_1$ cannot be lower-alkanoyl; (iv) when m is 0, n is 1, L is —O—, —S— or —SO—, and R$_2$, R$_3$ and R$_4$ are all hydrogen, or when m is 0, n is 1, L is —S—, R$_2$ and R$_4$ are hydrogen and R$_3$ is halogen, or when m is 0, n is 1, L is —SO— or —SO$_2$—, R$_2$ is carbo-lower-alkoxy and R$_3$ and R$_4$ are both hydrogen, R$_1$ cannot be phenyl or substituted phenyl.

In the following claims "corresponding" means that a variable of the structural formula of claim 1 (formula I above) which is repeated in another formula has the same meaning in the other formula as it has in the formula of claim 1 unless otherwise stated and that "substituted phenyl" and "substituted heterocyclyl" mean phenyl and heterocyclyl substituted as defined in claim 1.

We claim:

1. A compound of the formula

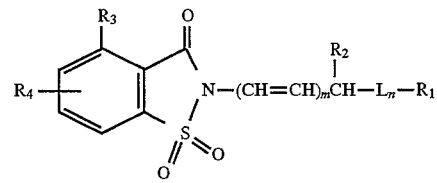

wherein m and n are each independently 0 or 1;

L is —S—

R$_1$ is 1-(3-acetamidophenyl)tetrazol-5-yl, 1-(3-heptanamidophenyl)tetrazol-5-yl, 1-methyltetrazol-5-yl, 1-cyclohexyltetrazol-5-yl, 1-(3-aminophenyl)tetrazol-5-yl, 1-(4-carboxyphenyl)tetrazol-5-yl, 1-(3,5-dimethoxycarbonylphenyl)tetrazol-5-yl, 1-[2-(4-morpholinyl)ethyl]-tetrazol-5-yl, 1-(3-pyridyl)tetrazol-5-yl, 2-methyltetrazol-5-yl, 1-ethoxycarbonylmethyltetrazol-5-yl,
1-(2-hydroxyethyl)tetrazol-5-yl,
1-dimethylaminocarbonylmethyltetrazol-5-yl,
1-carboxymethyltetrazol-5-yl,
1-(3-succinoylaminophenyl)tetrazol-5-yl, or
1-(2,5-dimethoxyphenyl)tetrazol-5-yl;

R₂ is hydrogen, lower-alkoxycarbonyl, phenyl or phenylthio;

R₃ is hydrogen, chloro, methyl, ethyl, isopropyl or ethoxy; and

R₄ is hydrogen, amino, acetylamino or methoxy.

2. A compound of the formula

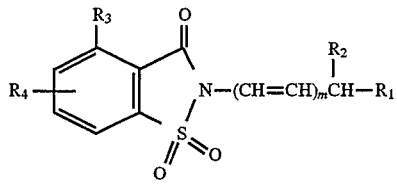

wherein m is 0

R₁ is 5-oxo-1-tetrazolinyl or 5-thioxo-1-tetrazolinyl or substituted 5-oxo-1-tetrazolinyl or 5-thioxo-1-tetrazolinyl;

R₂ is hydrogen;

R₃ is hydrogen or lower-alkyl; and

R₄ is hydrogen or lower-alkoxy.

3. A compound of the formula

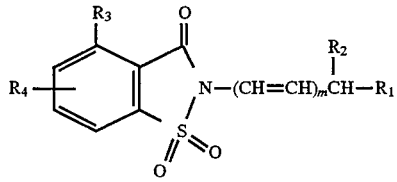

wherein m is 0;

R₁ is
 4-(4-carboxyphenyl)-5-thioxotetrazolin-1-yl,
 4-(3-pyridyl)-5-thioxotetrazolin-1-yl,
 2-methyl-5-thioxotetrazolin-1-yl or
 4-phenyl-5-thioxotetrazolin-1-yl;

R₂ is hydrogen, lower-alkoxycarbonyl, phenyl or phenylthio;

R₃ is hydrogen or chloro; and

R₄ is hydrogen or 6-methoxy.

4. A compound of the formula

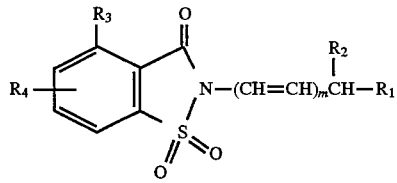

wherein m is 0;

R₁ is 1H-(5-tetrazolyl), 5-oxo-1-tetrazolinyl or, when R₂ as defined below is other than phenylthio, 5-thioxo-1-tetrazolindyl, R₂ is methoxycarbonyl, phenyl or phenylthio;

R₃ is hydrogen; and

R₄ is hydrogen.

5. A compound of the formula

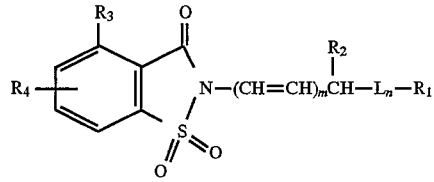

wherein

L is —S— m is 1;

n is 1;

R₁ is 1H-(5-tetrazolyl), 5-oxo-1-tetrazolinyl or, when R₂ as defined below is other than phenylthio, 5-thioxo-1-tetrazolindyl, R₂ is hydrogen;

R₃ is hydrogen or isopropyl; and

R₄ is hydrogen or methoxy.

6. A pharmaceutical composition which comprises a pharmaceutical carrier and a compound having the formula

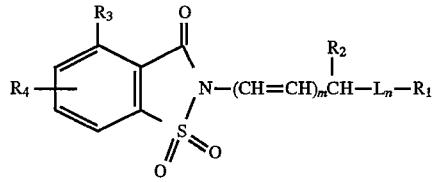

wherein

L is —S—;

m and n are each independently 0 or 1;

R₁ is 1H-(5-tetrazolyl), 5-oxo-1-tetrazolinyl or, when R₂ as defined below is other than phenylthio, 5-thioxo-1-tetrazolindyl, or said 1H-(5-tetrazolyl), 5-oxo-1-tetrazolinyl or 5-thioxo-1-tetrazolinyl substituted on any nitrogen atom by lower-alkyl, hydroxy-lower-alkyl, cycloalkyl, 2-, 3- or 4-pyridinyl, carboxy-lower-alkyl, lower-alkoxycarbonyl-lower-alkyl, aminocarbonyl-lower-alkyl, lower-alkylaminocarbonyl-lower-alkyl, di-lower-alkylamino-carbonyl-lower-alkyl, amino-lower-alkyl, lower-alkylamino-lower-alkyl, di-lower-alkyl-amino-lower-alkyl, 4-morpholinyl-lower-alkyl, 1-piperidinyl-lower-alkyl, 1-pyrrolidinyl-lower-alkyl, phenyl or phenyl substituted by amino, lower-alkyl-amino, di-lower-alkylamino, lower-alkanamido, N-lower-alkyl-lower-alkanamido, carboxy-lower-alkanamido, carboxy, lower-alkoxycarbonyl, lower-alkoxy, halo or carboxy-lower-alkanoylamino;

R₂ is hydrogen, lower-alkoxycarbonyl, phenyl or phenylthio;

R₃ is hydrogen, halo, primary or secondary lower-alkyl, lower-alkoxy, lower-alkoxycarbonyl, phenyl, fluoro-lower-alkyl, lower-alkenyl, cyano or di-lower-alkylamino; and R₄ is hydrogen or from one to three substituents selected from halo, cyano, nitro, amino, lower-alkanamido, phenyl-lower-alkanamido, diphenyl-loweralkanamido, lower-alkylsulfonylamino, polyfluoro-lower-alkylsulfonylamino, aminosulfonyl, lower-alkyl, polyhalo-lower-alkyl, cycloalkyl, polyhalo-lower-alkoxy, hydroxy, lower-alkoxy, carboxy, hydroxymethyl, formyl, aminomethyl, lower-alkylsulfonyl, polyhalo-lower-alkylsulfonyl, lower-alkylsulfonyl-aminosulfonyl, lower-alkoxy-lower-alkoxy, lower-alkoxy-poly-lower-alkyleneoxy, carboxy-lower-alkoxy, lower-alkoxycarbonyl-lower-alkoxy or di-lower-alkylaminocarbonyloxy;

and wherein the —$CHR_2$— group is always appended either through the L moiety as defined above to a carbon atom of $R_1$ when n is 1 or directly to a ring nitrogen atom of the $R_1$ moiety, when n is 0, with the proviso that when m is 0, n is 1, and $R_2$, $R_3$ and $R_4$ are each hydrogen, $R_1$ cannot be 1-phenyl-1H-(5-tetrazolyl).

7. The pharmaceutical composition according to claim 6 wherein n is 1 and $R_1$ is 1-phenyltetrazol-5-yl.

8. The pharmaceutical composition according to claim 7 wherein m is 0, $R_2$ is hydrogen, $R_3$ is hydrogen, chloro, bromo, methyl, ethyl, propyl, isopropyl, sec.-butyl, methoxy, ethoxy, isopropoxy or phenyl and $R_4$ is hydrogen, 7-chloro, 5-nitro, 6-nitro, 5-amino, 5-acetylamino, 5-(3,3-diphenylpropionamido), 5-(1,1,3,3-tetramethylbutyl), 6-hydroxy, 7-hydroxy, 5-methoxy, 6-methoxy, 7-methoxy, 5,6-dimethoxy, 5,7-dimethoxy, 6,7-dimethoxy, 6-[2-(2-methoxyethoxy)ethoxy], 7-[2-(2-methoxyethoxy)ethoxy], 7-carboxymethoxy, 7-(t-butoxycarbonyl)methoxy, 7-dimethylaminocarbonyloxy, 6-propyl-7-methoxy, 5,7-dimethoxy-6-methyl or 5-hydroxy-6-methoxy.

* * * * *